(12) United States Patent
Bluvshtein et al.

(10) Patent No.: US 10,149,933 B2
(45) Date of Patent: Dec. 11, 2018

(54) COIL PARAMETERS AND CONTROL

(71) Applicant: Minnetronix, Inc., Saint Paul, MN (US)

(72) Inventors: Vlad Bluvshtein, Plymouth, MN (US); Lori Lucke, Rosemount, MN (US)

(73) Assignee: Minnetronix, Inc., Saint Paul, MN (US)

(*) Notice: Subject to any disclaimer, the term of this patent is extended or adjusted under 35 U.S.C. 154(b) by 481 days.

(21) Appl. No.: 14/808,398

(22) Filed: Jul. 24, 2015

(65) Prior Publication Data

US 2016/0022889 A1 Jan. 28, 2016

Related U.S. Application Data

(60) Provisional application No. 62/029,333, filed on Jul. 25, 2014, provisional application No. 62/147,402, filed on Apr. 14, 2015.

(51) Int. Cl.
*A61N 1/362* (2006.01)
*A61M 1/12* (2006.01)
(Continued)

(52) U.S. Cl.
CPC .......... *A61M 1/122* (2014.02); *A61M 1/1032* (2014.02); *A61M 1/1086* (2013.01);
(Continued)

(58) Field of Classification Search
CPC ........ A61M 1/12; A61M 1/101; A61M 1/122; A61M 1/127; A61M 1/1032;
(Continued)

(56) References Cited

U.S. PATENT DOCUMENTS 3,195,540 A 7/1965 Waller
3,566,876 A 3/1971 Stoft et al.
(Continued)

FOREIGN PATENT DOCUMENTS

DE 102015112097 A1 1/2016
FR 2587221 3/1987
(Continued)

OTHER PUBLICATIONS

Andia et al., "Closed Loop Wireless Power Transmission for Implantable Medical Devices," IEEE, 2011, pp. 404-407.
(Continued)

*Primary Examiner* — Mallika D Fairchild
(74) *Attorney, Agent, or Firm* — Dorsey & Whitney LLP

(57) ABSTRACT

Present embodiments are directed to measuring and calculating parameters to control and monitor a power transfer in an implanted medical device. The medical device may be implanted in a subject and typically includes an artificial heart or ventricle assist device. The system measures parameters and uses the parameters to calculate a coupling coefficient for coils that transfer power between an external primary and an implanted secondary. The system uses the calculated coupling coefficient to estimate heat flux being generated in the system. Based on the level heat flux detected, the system may issue alerts to warn the subject or control actions to mitigate the effects of the heat flux.

17 Claims, 51 Drawing Sheets

(51) Int. Cl.
  *G01K 7/36* (2006.01)
  *G01K 7/42* (2006.01)
  *G01K 13/00* (2006.01)
  *G01K 17/00* (2006.01)
  *A61M 1/10* (2006.01)

(52) U.S. Cl.
  CPC .............. *A61M 1/127* (2013.01); *G01K 7/36* (2013.01); *G01K 7/42* (2013.01); *G01K 13/002* (2013.01); *G01K 17/00* (2013.01); *A61M 1/101* (2013.01); *A61M 1/1036* (2014.02); *A61M 1/1039* (2014.02); *A61M 1/1081* (2013.01); *A61M 1/12* (2013.01); *A61M 2205/3368* (2013.01); *A61M 2205/8243* (2013.01)

(58) Field of Classification Search
  CPC .............. A61M 1/1036; A61M 1/1039; A61M 1/1081; A61M 1/1086; A61M 2205/3368; A61M 2205/8243; G01K 7/36; G01K 7/42; G01K 17/00; G01K 13/0002
  See application file for complete search history.

(56) References Cited

U.S. PATENT DOCUMENTS

| | | |
|---|---|---|
| 3,756,246 A | 9/1973 | Thaler et al. |
| 3,760,332 A | 9/1973 | Berkovits et al. |
| 3,806,807 A | 4/1974 | Nakamura |
| 3,943,535 A | 3/1976 | Schulman |
| 4,143,661 A | 3/1979 | LaForge et al. |
| 4,164,946 A | 8/1979 | Langer |
| 4,221,543 A | 9/1980 | Cosentino et al. |
| 4,233,546 A | 11/1980 | Berthiaume |
| 4,237,895 A | 12/1980 | Johnson |
| 4,263,642 A | 4/1981 | Simmons et al. |
| 4,361,153 A | 11/1982 | Slocum et al. |
| 4,417,349 A | 11/1983 | Hills et al. |
| 4,439,806 A | 3/1984 | Brajder |
| 4,441,210 A | 4/1984 | Hochmair et al. |
| 4,446,513 A | 5/1984 | Clenet |
| 4,453,537 A | 6/1984 | Spitzer |
| 4,469,104 A | 9/1984 | Peers-Trevarton |
| 4,494,545 A | 1/1985 | Slocum et al. |
| 4,532,932 A | 8/1985 | Batty, Jr. |
| 4,561,443 A | 12/1985 | Hogrefe et al. |
| 4,625,730 A | 12/1986 | Fountain et al. |
| 4,665,896 A | 5/1987 | LaForge et al. |
| 4,691,270 A | 9/1987 | Pruitt |
| 4,706,689 A | 11/1987 | Man |
| 4,768,512 A | 9/1988 | Imran |
| 4,774,950 A | 10/1988 | Cohen |
| 4,848,346 A | 7/1989 | Crawford |
| 4,855,888 A | 8/1989 | Henze et al. |
| 4,898,173 A | 2/1990 | Daglow et al. |
| 4,924,171 A | 5/1990 | Baba et al. |
| 4,925,443 A | 5/1990 | Heilman et al. |
| 4,933,798 A | 6/1990 | Widmayer et al. |
| 4,941,652 A | 6/1990 | Nagano et al. |
| 4,941,201 A | 7/1990 | Davis |
| 4,947,844 A | 8/1990 | McDermott |
| 4,953,068 A | 8/1990 | Henze |
| 4,964,027 A | 10/1990 | Cook et al. |
| 4,979,506 A | 12/1990 | Silvian |
| 5,012,807 A | 5/1991 | Stutz, Jr. |
| 5,076,270 A | 12/1991 | Stutz, Jr. |
| 5,132,888 A | 7/1992 | Lo et al. |
| 5,132,889 A | 7/1992 | Hitchcock et al. |
| 5,157,593 A | 10/1992 | Jain |
| 5,158,097 A | 10/1992 | Christlieb |
| 5,205,810 A | 4/1993 | Guiraudon et al. |
| 5,279,292 A | 1/1994 | Baumann et al. |
| 5,314,457 A | 5/1994 | Jeutter et al. |
| 5,327,335 A | 7/1994 | Maddali et al. |
| 5,345,375 A | 9/1994 | Mohan |
| 5,350,413 A | 9/1994 | Miller |
| 5,400,235 A | 3/1995 | Carroll |
| 5,413,595 A | 5/1995 | Stutz, Jr. |
| 5,438,498 A | 8/1995 | Ingemi |
| 5,444,608 A | 8/1995 | Jain |
| 5,456,715 A | 10/1995 | Liotta |
| 5,499,178 A | 3/1996 | Mohan |
| 5,500,004 A | 3/1996 | Ansourian et al. |
| 5,515,264 A | 5/1996 | Stacey |
| 5,522,865 A | 6/1996 | Schuman et al. |
| 5,559,689 A | 9/1996 | Kirchberg et al. |
| 5,569,156 A | 10/1996 | Mussivand |
| 5,569,307 A | 10/1996 | Schulman et al. |
| 5,584,870 A | 12/1996 | Single et al. |
| 5,594,635 A | 1/1997 | Gegner |
| 5,630,836 A | 5/1997 | Prem et al. |
| 5,662,692 A | 9/1997 | Paspa et al. |
| 5,674,281 A | 10/1997 | Snyder |
| 5,690,693 A | 11/1997 | Wang et al. |
| 5,702,427 A | 12/1997 | Ecker et al. |
| 5,702,431 A | 12/1997 | Wang et al. |
| 5,704,891 A | 1/1998 | Mussivand |
| 5,713,939 A | 2/1998 | Nedungadi et al. |
| 5,713,954 A | 2/1998 | Rosenberg et al. |
| 5,722,930 A | 3/1998 | Larson, Jr. et al. |
| 5,728,154 A | 3/1998 | Crossett et al. |
| 5,735,887 A | 4/1998 | Barreras, Sr. et al. |
| 5,741,314 A | 4/1998 | Daly et al. |
| 5,741,316 A | 4/1998 | Chen et al. |
| 5,749,909 A | 5/1998 | Schroeppel et al. |
| 5,751,125 A | 5/1998 | Weiss |
| 5,755,748 A | 5/1998 | Borza |
| 5,781,419 A | 7/1998 | Kutkut et al. |
| 5,945,762 A | 8/1999 | Chen et al. |
| 5,948,006 A | 9/1999 | Mann |
| 5,991,665 A | 11/1999 | Wang et al. |
| 5,995,874 A | 11/1999 | Borza |
| 6,047,214 A | 4/2000 | Mueller et al. |
| 6,058,330 A | 5/2000 | Borza |
| 6,067,474 A | 5/2000 | Schulman et al. |
| 6,076,016 A | 6/2000 | Feierbach |
| 6,088,619 A | 7/2000 | Hein et al. |
| 6,092,531 A | 7/2000 | Chen et al. |
| 6,112,121 A | 8/2000 | Paul et al. |
| 6,149,683 A | 11/2000 | Lancisi et al. |
| 6,212,430 B1 | 4/2001 | Kung |
| 6,233,485 B1 | 5/2001 | Armstrong et al. |
| 6,240,318 B1 | 5/2001 | Phillips |
| 6,254,525 B1 | 7/2001 | Reinhardt et al. |
| 6,263,247 B1 | 7/2001 | Mueller et al. |
| 6,275,737 B1 | 8/2001 | Mann |
| 6,324,430 B1 | 11/2001 | Zarinetchi et al. |
| 6,342,071 B1 | 1/2002 | Pless |
| 6,345,203 B1 | 2/2002 | Mueller et al. |
| 6,366,817 B1 | 4/2002 | Kung |
| 6,389,318 B1 | 5/2002 | Zarinetchi et al. |
| 6,400,991 B1 | 6/2002 | Kung |
| 6,424,867 B1 | 7/2002 | Snell |
| 6,430,444 B1 | 8/2002 | Borza |
| 6,434,194 B1 | 8/2002 | Eisenberg et al. |
| 6,442,434 B1 | 8/2002 | Zarinetchi et al. |
| 6,443,891 B1 | 9/2002 | Grevious |
| 6,451,055 B1 | 9/2002 | Weiss |
| 6,458,164 B1 | 10/2002 | Weiss |
| 6,478,820 B1 | 11/2002 | Weiss |
| 6,517,476 B1 | 2/2003 | Bedoya et al. |
| 6,579,315 B1 | 6/2003 | Weiss |
| 6,592,620 B1 | 7/2003 | Lancisi et al. |
| 6,641,612 B2 | 11/2003 | Pless |
| 6,648,914 B2 | 11/2003 | Berrang et al. |
| 6,671,554 B2 | 12/2003 | Gibson et al. |
| 6,810,289 B1 | 10/2004 | Shaquer |
| 6,831,944 B1 | 12/2004 | Misra et al. |
| 6,850,803 B1 | 2/2005 | Jimenez |
| 6,862,478 B1 | 3/2005 | Goldstein |
| 6,961,005 B2 | 11/2005 | Clement et al. |
| 6,978,181 B1 | 12/2005 | Snell |
| 7,003,353 B1 | 2/2006 | Parkhouse |

(56) References Cited

U.S. PATENT DOCUMENTS

| | | |
|---|---|---|
| 7,035,689 B1 | 4/2006 | Hawkins et al. |
| 7,062,331 B2 | 6/2006 | Zarinetchi et al. |
| 7,069,086 B2 | 6/2006 | Von Arx |
| 7,076,206 B2 | 7/2006 | Elferich et al. |
| 7,079,901 B1 | 7/2006 | Loftin et al. |
| 7,155,291 B2 | 12/2006 | Zarinetchi et al. |
| 7,173,411 B1 | 2/2007 | Pond |
| 7,191,007 B2 | 3/2007 | Desai et al. |
| 7,299,095 B1 | 11/2007 | Barlow et al. |
| 7,317,947 B2 | 1/2008 | Wahlstrand et al. |
| 7,512,443 B2 | 3/2009 | Phillips et al. |
| 7,515,967 B2 | 4/2009 | Phillips |
| 7,574,262 B2 | 8/2009 | Haugland et al. |
| 7,599,743 B2 | 10/2009 | Hassler, Jr. et al. |
| 7,672,732 B2 | 3/2010 | Sun et al. |
| 7,738,965 B2 | 6/2010 | Phillips et al. |
| 7,774,069 B2 | 8/2010 | Olson |
| 7,781,916 B2 | 8/2010 | Boys |
| 7,822,480 B2 | 10/2010 | Park et al. |
| 7,848,814 B2 | 12/2010 | Torgerson et al. |
| 7,962,211 B2 | 6/2011 | Torgerson et al. |
| 8,024,047 B2 | 9/2011 | Olson et al. |
| 8,027,735 B1 | 9/2011 | Tziviskos et al. |
| 8,032,486 B2 | 10/2011 | Townsend et al. |
| 8,050,068 B2 | 11/2011 | Hussmann et al. |
| 8,093,758 B2 | 1/2012 | Hussmann |
| 8,097,983 B2 | 1/2012 | Karalis et al. |
| 8,116,681 B2 | 2/2012 | Baarman |
| 8,126,563 B2 | 2/2012 | Ibrahim |
| 8,265,770 B2 | 9/2012 | Toy et al. |
| 8,311,638 B2 | 11/2012 | Aghassian |
| 8,428,712 B2 | 4/2013 | Davis et al. |
| 8,428,724 B2 | 4/2013 | Sage |
| 8,437,855 B2 | 5/2013 | Sjostedt et al. |
| 8,457,758 B2 | 6/2013 | Olson |
| 8,473,066 B2 | 6/2013 | Aghassian et al. |
| 8,515,112 B2 | 8/2013 | Crawford et al. |
| 8,543,209 B2 | 9/2013 | Tyers et al. |
| 8,626,308 B2 | 1/2014 | Meskens |
| 8,630,717 B2 | 1/2014 | Olson et al. |
| 8,676,337 B2 | 3/2014 | Kallmyer |
| 8,706,255 B2 | 4/2014 | Philips et al. |
| 8,738,148 B2 | 5/2014 | Olson et al. |
| 8,764,621 B2 | 6/2014 | Badstibner et al. |
| 8,766,788 B2 | 7/2014 | D'Ambrosio |
| 8,903,515 B2 | 12/2014 | Mashiach |
| 8,972,012 B2 | 3/2015 | Lim |
| 9,192,772 B1 | 11/2015 | Kishiyama et al. |
| 9,603,984 B2 | 3/2017 | Romero et al. |
| 2002/0021226 A1 | 2/2002 | Clement et al. |
| 2002/0032471 A1 | 3/2002 | Loftin et al. |
| 2002/0087204 A1 | 7/2002 | Kung et al. |
| 2002/0128709 A1 | 9/2002 | Pless |
| 2002/0177884 A1 | 11/2002 | Ahn et al. |
| 2003/0045912 A1 | 3/2003 | Williams et al. |
| 2003/0085684 A1 | 5/2003 | Tsukamoto et al. |
| 2003/0171792 A1 | 9/2003 | Zarinetchi et al. |
| 2004/0034393 A1 | 2/2004 | Hansen et al. |
| 2004/0039423 A1 | 2/2004 | Dolgin |
| 2004/0049245 A1 | 3/2004 | Gass et al. |
| 2005/0065570 A1 | 3/2005 | Stein et al. |
| 2005/0075694 A1 | 4/2005 | Schmeling et al. |
| 2005/0075696 A1 | 4/2005 | Forsberg et al. |
| 2005/0131491 A1 | 6/2005 | Shaquer |
| 2005/0245996 A1 | 11/2005 | Phillips et al. |
| 2005/0288739 A1 | 12/2005 | Hassler, Jr. et al. |
| 2005/0288741 A1 | 12/2005 | Hassler, Jr. et al. |
| 2006/0020305 A1 | 1/2006 | Desai et al. |
| 2006/0036127 A1 | 2/2006 | Delgado, III |
| 2006/0167333 A1 | 7/2006 | Moore et al. |
| 2006/0184204 A1 | 8/2006 | He |
| 2006/0247737 A1 | 11/2006 | Olson |
| 2006/0267790 A1 | 11/2006 | Matthiessen et al. |
| 2007/0060787 A1 | 3/2007 | Peters et al. |
| 2007/0255349 A1 | 11/2007 | Torgerson et al. |
| 2007/0255350 A1 | 11/2007 | Torgerson et al. |
| 2008/0065173 A1 | 3/2008 | Wahlstrand et al. |
| 2008/0198947 A1 | 8/2008 | Zierhofer |
| 2008/0255631 A1 | 10/2008 | Sjostedt et al. |
| 2008/0303480 A1 | 12/2008 | Prutchi et al. |
| 2009/0067653 A1 | 3/2009 | Meskens et al. |
| 2009/0281597 A1 | 11/2009 | Parramon et al. |
| 2010/0010582 A1 | 1/2010 | Carbunaru et al. |
| 2010/0033023 A1 | 2/2010 | Baarman |
| 2010/0033240 A1 | 2/2010 | Denison et al. |
| 2010/0063347 A1 | 3/2010 | Yomtov et al. |
| 2010/0164296 A1 | 7/2010 | Kurs et al. |
| 2010/0249886 A1 | 9/2010 | Park et al. |
| 2010/0268305 A1 | 10/2010 | Olson |
| 2010/0292759 A1 | 11/2010 | Hahn |
| 2010/0327887 A1 | 12/2010 | Denison et al. |
| 2011/0004278 A1 | 1/2011 | Aghassian et al. |
| 2011/0093048 A1 | 4/2011 | Aghassian |
| 2011/0101790 A1 | 5/2011 | Budgett |
| 2011/0106210 A1 | 5/2011 | Meskens |
| 2011/0301669 A1 | 12/2011 | Olson |
| 2011/0313490 A1 | 12/2011 | Parramon et al. |
| 2012/0032522 A1 | 2/2012 | Schatz et al. |
| 2012/0095528 A1 | 4/2012 | Miller, III et al. |
| 2012/0154143 A1 | 6/2012 | D'Ambrosio |
| 2012/0157753 A1 | 6/2012 | D'Ambrosio |
| 2012/0157754 A1 | 6/2012 | D'Ambrosio |
| 2012/0197352 A1 | 8/2012 | Carbunaru et al. |
| 2012/0215285 A1 | 8/2012 | Tahmasian |
| 2012/0265003 A1 | 10/2012 | D'Ambrosio et al. |
| 2013/0023958 A1 | 1/2013 | Fell |
| 2013/0041429 A1 | 2/2013 | Aghassian |
| 2013/0043736 A1 | 2/2013 | Zilbershlag |
| 2013/0046361 A1 | 2/2013 | DiGiore et al. |
| 2013/0123881 A1 | 5/2013 | Aghassian |
| 2013/0127253 A1 | 5/2013 | Stark |
| 2013/0158631 A1 | 6/2013 | Shea et al. |
| 2013/0163688 A1 | 6/2013 | Calvin |
| 2013/0278226 A1 | 10/2013 | Cong et al. |
| 2013/0310629 A1 | 11/2013 | Lafontaine |
| 2013/0317345 A1 | 11/2013 | Frustaci et al. |
| 2013/0331638 A1 | 12/2013 | Cameron et al. |
| 2013/0338734 A1 | 12/2013 | Hoyer et al. |
| 2014/0005749 A1 | 1/2014 | Stahmann et al. |
| 2014/0031607 A1 | 1/2014 | Zilbershlag et al. |
| 2014/0139034 A1 | 5/2014 | Sankar et al. |
| 2014/0371823 A1 | 12/2014 | Mashiach et al. |
| 2015/0069847 A1 | 3/2015 | Meyer et al. |
| 2015/0073203 A1 | 3/2015 | Wariar et al. |
| 2015/0207331 A1* | 7/2015 | Petersen ............ H02J 5/005 307/104 |
| 2015/0209591 A1 | 7/2015 | Meskens |
| 2015/0333801 A1 | 11/2015 | Hosotani |
| 2015/0364861 A1 | 12/2015 | Lucke et al. |
| 2015/0380988 A1 | 12/2015 | Chappell et al. |
| 2016/0175600 A1 | 6/2016 | Amir et al. |
| 2016/0197511 A1 | 7/2016 | Atasoy et al. |
| 2016/0248265 A1 | 8/2016 | Oo et al. |
| 2016/0294225 A1 | 10/2016 | Blum et al. |
| 2017/0119947 A1 | 5/2017 | Eldridge et al. |

FOREIGN PATENT DOCUMENTS

| | | |
|---|---|---|
| JP | 2597623 B2 | 4/1997 |
| WO | 8301006 | 3/1983 |
| WO | 8700420 | 1/1987 |
| WO | 9809588 | 3/1998 |
| WO | 0191678 A1 | 12/2001 |
| WO | 2007126454 A2 | 11/2007 |
| WO | 2008106717 A1 | 9/2008 |
| WO | 2009029977 A1 | 3/2009 |
| WO | 2010133702 A2 | 11/2010 |
| WO | 2011119352 A1 | 9/2011 |
| WO | 2012077088 A2 | 6/2012 |
| WO | 2012077088 A3 | 6/2012 |

(56) References Cited

FOREIGN PATENT DOCUMENTS

WO 2014036449 A1 3/2014
WO 2014169940 A1 10/2014

OTHER PUBLICATIONS

Bonsor, "How Artificial Hearts Work," HowStuffWorks, Aug. 9, 2001, downloaded from HowStuffWorks.com. at http://science.howstuffworks.com/innovation/everyday-innovations/artificial-heart.htm (12 pages).

Knecht et al., "Optimization of Transcutaneous Energy Transfer Coils for High Power Medical Applications," Workshop on Control and Modeling for Power Electronics (COMPEL), 2014, pp. 1-10.

Ng et al., "Closed-Loop Inductive Link for Wireless Powering of a High Density Electrode Array Retinal Prosthesis," IEEE, 2009, pp. 92-97.

Ng et al., "Wireless Power Delivery for Retinal Prostheses," 33rd Annual International Conference of the IEEE EMBS, Aug. 30, 2011-Sep. 3, 2011, pp. 8356-8360.

Shmilovitz et al., "Noninvasive Control of the Power Transferred to an Implanted Device by an Ultrasonic Transcutaneous Energy Transfer Link," IEEE Transactions on Biomedical Engineering, Apr. 2014, pp. 995-1004, vol. 61, No. 4.

First Office Action for German Patent Application No. 102016106683.4, dated Mar. 4, 2018, with English Translation (17 pages).

\* cited by examiner

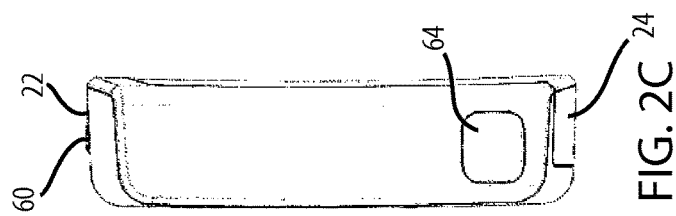
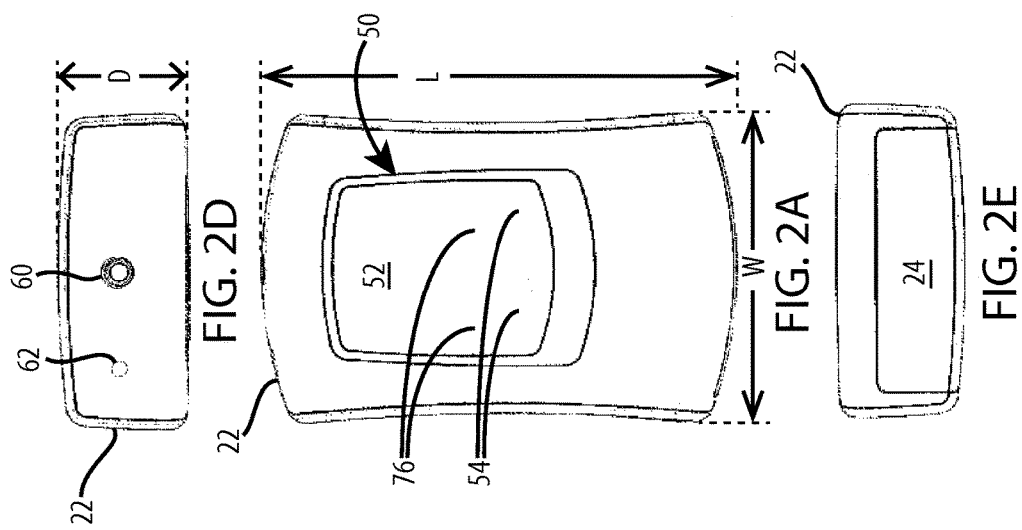
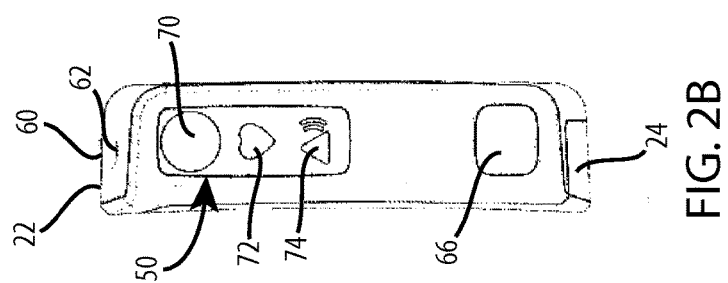

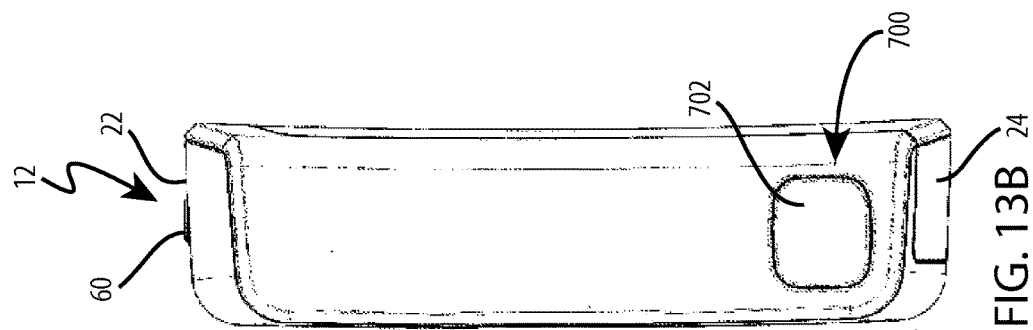
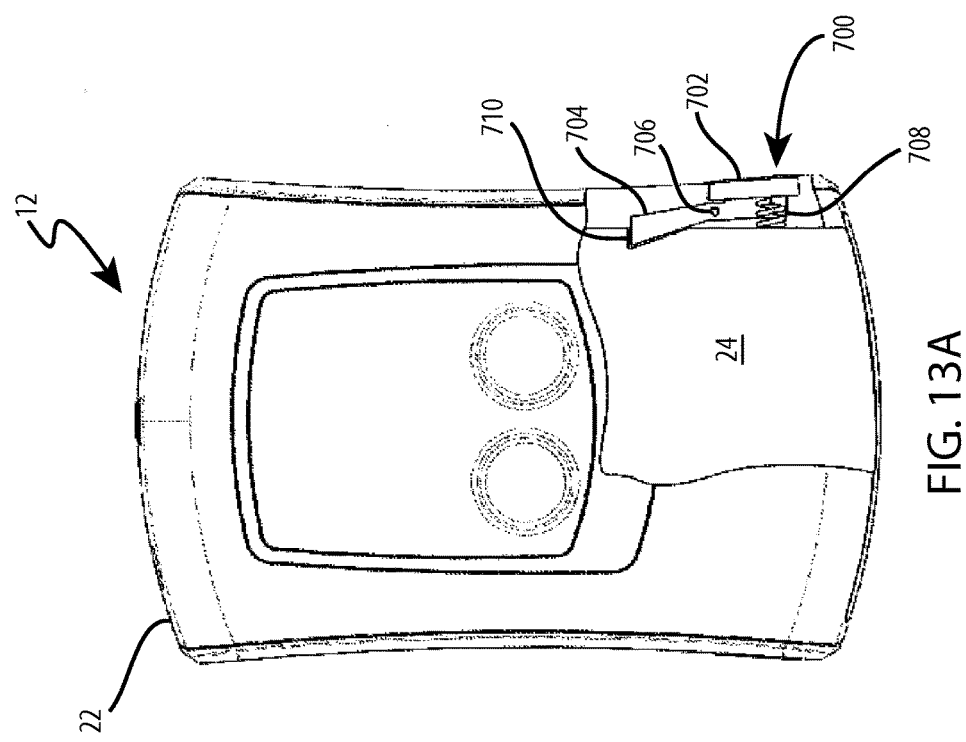

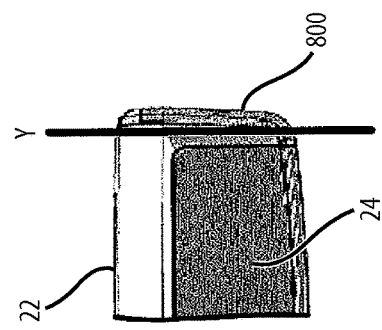
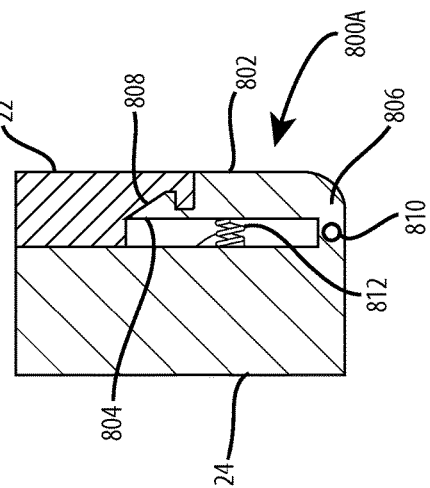
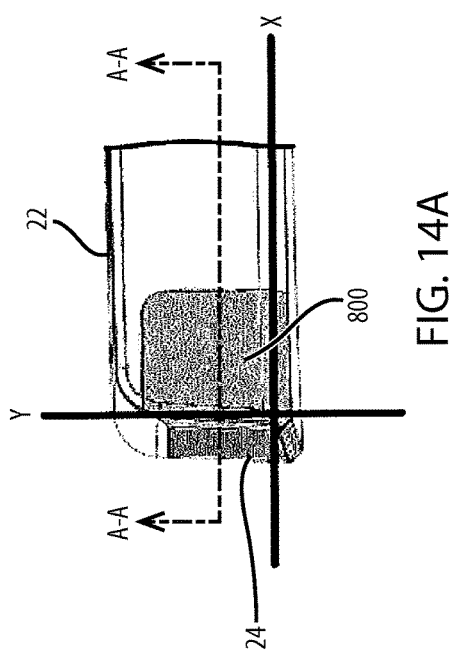
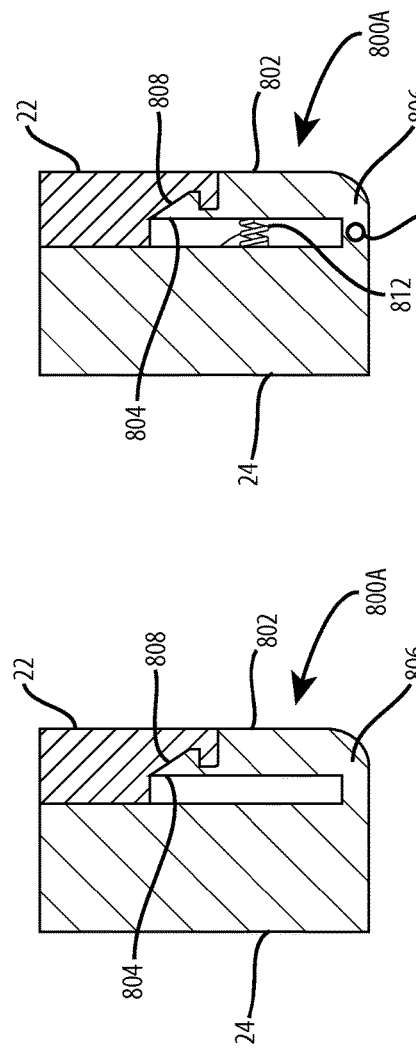
FIG. 14B
FIG. 14D
FIG. 14A
FIG. 14C

COIL PARAMETERS AND CONTROL

CROSS-REFERENCE TO RELATED APPLICATIONS

The present application claims the benefit under 35 U.S.C. § 119(e) to U.S. Provisional Patent Application No. 62/029,333 filed on Jul. 25, 2014, and U.S. Provisional Patent Application No. 62/147,402 filed on Apr. 14, 2015. The entire contents of each of these previously-flied provisional applications are incorporated by reference as if fully disclosed herein.

TECHNICAL FIELD

The technology described herein relates to systems and methods for measuring and calculating parameters to control and monitor a power transfer in an implanted medical device.

BACKGROUND

Currently, there is a need to deliver electric power to implanted medical devices such as artificial hearts and ventricle assist devices. It is possible to deliver power non-invasively through electromagnetic energy transmitted through the skin. However, problems can arise related to the implanted secondary, which receives power from the external primary. Specifically, the secondary can heat-up and injure the subject due to inadvertent non-optimal coupling, including possibly over-coupling or over-coupling, between the primary and the secondary. Because the secondary is implanted and thus relatively inaccessible, a problem can arise and cause injury before the user or the system is aware of the problem. Prior art systems fail to provide mechanisms for addressing these and other issues that concern transfer of electromagnetic energy to implanted medical devices. These and other deficiencies of the prior art are addressed herein.

SUMMARY

Present embodiments are directed to measuring and calculating parameters to control and monitor a power transfer in an implanted medical device. The medical device may be implanted in a subject and can include an artificial heart or ventricle assist device. The system measures parameters and uses the parameters to calculate a coupling coefficient for coils that transfer power between an external primary and an implanted secondary. The system uses the calculated coupling coefficient to estimate heat flux being generated in the system. Based on the level heat flux detected, the system may issue alerts to warn the subject or control actions to mitigate the effects of the heat flux.

In one aspect, the present disclosure is directed to a method of monitoring power transfer between a primary and secondary of a transcutaneous energy transfer system, including measuring at least one system status parameter, performing calculations using the measured status parameters, and performing a control operation based on the calculations.

In some implementations, the at least one system status parameter includes a regulation timing parameter.

In some implementations, measuring the regulation timing parameter includes measuring a primary current signal that indicates the timing of the voltage regulation in the secondary.

In some implementations, measuring the regulation timing parameter includes measuring a primary coil voltage signal that indicates the timing of the voltage regulation in the secondary.

In some implementations, measuring the regulation timing parameter includes measuring a primary capacitor voltage signal that indicates the timing of the voltage regulation in the secondary.

In some implementations, the at least one system status parameter includes a primary current signal.

In some implementations, measuring the primary current signal includes measuring a current in the primary through the operation of a current probe arranged in series with a primary coil.

In some implementations, measuring the primary current signal includes measuring a voltage across a primary coil.

In some implementations, measuring the primary current signal includes measuring a voltage across a primary capacitor.

In some implementations, performing calculations using the measured system status parameters includes a calculation of a coupling coefficient.

In some implementations, performing calculations using the measured system status parameters includes a first calculation of the primary heat flux, and a second calculation of the primary coil temperature.

In some implementations, performing calculations using the measured system status parameters includes a first calculation of a coupling coefficient, a second calculation of the secondary coil current, a third calculation of the secondary coil heat flux, and a forth calculation of the secondary coil temperature.

In some implementations, the control operation includes controlling input voltage based on the coupling coefficient.

In some implementations, the control operation includes control of secondary coil current to control secondary heat flux based on secondary coil heat flux calculation.

In some implementations, the control operation includes control of secondary coil current to control secondary temperature based on secondary coil temperature calculation.

In some implementations, the control operation includes control of primary coil current to control primary heat flux based on primary coil heat flux calculation.

In some implementations, the control operation includes control of primary coil current to control primary temperature based on primary coil temperature calculation.

In another aspect, the present disclosure is directed to a method of monitoring power transfer between a primary and secondary of a transcutaneous energy transfer system, including measuring at least one system status parameter, performing calculations using the measured status parameters, and generating an output based on the calculations.

In some implementations, the at least one system status parameter includes a regulation timing parameter.

In some implementations, measuring the regulation timing parameter includes measuring a primary current signal that indicates the timing of the voltage regulation in the secondary.

In some implementations, measuring the regulation timing parameter includes measuring a primary coil voltage signal that indicates the timing of the voltage regulation in the secondary.

In some implementations, measuring the regulation timing parameter includes measuring a primary capacitor voltage signal that indicates the timing of the voltage regulation in the secondary.

In some implementations, the at least one system status parameter includes a primary current signal.

In some implementations, measuring the primary current signal includes measuring a current in the primary through the operation of a current probe arranged in series with a primary coil.

In some implementations, measuring the at least one system status parameter includes determining the primary voltage.

In some implementations, measuring the primary current signal includes measuring a voltage across a primary coil.

In some implementations, measuring the primary current signal includes measuring a voltage across a primary capacitor.

In some implementations, performing calculations using the measured system status parameters includes a calculation of a coupling coefficient.

In some implementations, performing calculations using the measured system status parameters includes a calculation of the primary coil heat flux.

In some implementations, performing calculations using the measured system status parameters includes a calculation of the primary coil temperature.

In some implementations, performing calculations using the measured system status parameters includes a first calculation of a coupling coefficient, a second calculation of the secondary coil current, and a third calculation of the secondary coil heat flux.

In some implementations, performing calculations using the measured system status parameters includes a first calculation of a coupling coefficient, a second calculation of the secondary coil current, a third calculation of the secondary coil heat flux, and a fourth calculation of the secondary coil temperature.

In some implementations, the output includes assistance in placement and alignment of the external coil based on the calculated coupling coefficient.

In some implementations, the output includes decoupling notifications based on the calculated coupling coefficient.

In some implementations, the output includes heat flux notifications based on the calculated primary heat flux.

In some implementations, the output includes temperature notifications based on the calculated primary temperature.

In some implementations, the output includes heat flux notifications based on the calculated secondary heat flux.

In some implementations, the output includes temperature notifications based on the calculated secondary temperature.

In another aspect, the present disclosure is directed to a portable external device for a mechanical circulation support (MCS) system including a housing, a battery removably connected to the housing, and power module arranged within the housing, powered by the battery and configured to wirelessly transfer electric power across a skin boundary to an implantable pump.

In some implementations, the power module is configured to measure at least one system status parameter, perform calculations using the measured status parameters, and perform a control operation based on the calculations.

In some implementations, the at least one system status parameter includes a regulation timing parameter.

In some implementations, measuring the regulation timing parameter includes measuring a primary current signal that indicates the timing of the voltage regulation in the secondary.

In some implementations, measuring the regulation timing parameter includes measuring a primary coil voltage signal that indicates the timing of the voltage regulation in the secondary.

In some implementations, measuring the regulation timing parameter includes measuring a primary capacitor voltage signal that indicates the timing of the voltage regulation in the secondary.

In some implementations, the at least one system status parameter includes a primary current signal.

In some implementations, measuring the primary current signal includes measuring a current in the primary through the operation of a current probe arranged in series with a primary coil.

In some implementations, measuring the primary current signal includes measuring a voltage across a primary coil.

In some implementations, measuring the primary current signal includes measuring a voltage across a primary capacitor.

In some implementations, performing calculations using the measured system status parameters includes a calculation of a coupling coefficient.

In some implementations, performing calculations using the measured system status parameters includes a first calculation of the primary heat flux, and a second calculation of the primary coil temperature.

In some implementations, performing calculations using the measured system status parameters includes a first calculation of a coupling coefficient, a second calculation of the secondary coil current, a third calculation of the secondary coil heat flux, and a forth calculation of the secondary coil temperature.

In some implementations, the control operation includes controlling input voltage based on the coupling coefficient.

In some implementations, the control operation includes control of secondary coil current to control secondary heat flux based on secondary coil heat flux calculation.

In some implementations, the control operation includes control of secondary coil current to control secondary temperature based on secondary coil temperature calculation.

In some implementations, the control operation includes control of primary coil current to control primary heat flux based on primary coil heat flux calculation.

In some implementations, the control operation includes control of primary coil current to control primary temperature based on primary coil temperature calculation.

In some implementations, the power module is configured to measure at least one system status parameter, perform calculations using the measured status parameters, and generate an output based on the calculations.

In some implementations, the at least one system status parameter includes a regulation timing parameter.

In some implementations, measuring the regulation timing parameter includes measuring a primary current signal that indicates the timing of the voltage regulation in the secondary.

In some implementations, measuring the regulation timing parameter includes measuring a primary coil voltage signal that indicates the timing of the voltage regulation in the secondary.

In some implementations, measuring the regulation timing parameter includes measuring a primary capacitor voltage signal that indicates the timing of the voltage regulation in the secondary.

In some implementations, the at least one system status parameter includes a primary current signal.

In some implementations, measuring the primary current signal includes measuring a current in the primary through the operation of a current probe arranged in series with a primary coil.

In some implementations, measuring the at least one system status parameter includes determining the primary voltage.

In some implementations, measuring the primary current signal includes measuring a voltage across a primary coil.

In some implementations, measuring the primary current signal includes measuring a voltage across a primary capacitor.

In some implementations, performing calculations using the measured system status parameters includes a calculation of a coupling coefficient.

In some implementations, performing calculations using the measured system status parameters includes a calculation of the primary coil heat flux.

In some implementations, performing calculations using the measured system status parameters includes a calculation of the primary coil temperature.

In some implementations, performing calculations using the measured system status parameters includes a first calculation of a coupling coefficient, a second calculation of the secondary coil current, and a third calculation of the secondary coil heat flux.

In some implementations, performing calculations using the measured system status parameters includes a first calculation of a coupling coefficient, a second calculation of the secondary coil current, a third calculation of the secondary coil heat flux, and a fourth calculation of the secondary coil temperature.

In some implementations, the output includes assistance in placement and alignment of the external coil based on the calculated coupling coefficient.

In some implementations, the output includes decoupling notifications based on the calculated coupling coefficient.

In some implementations, the output includes heat flux notifications based on the calculated primary heat flux.

In some implementations, the output includes temperature notifications based on the calculated primary temperature.

In some implementations, the output includes heat flux notifications based on the calculated secondary heat flux.

In some implementations, the output includes temperature notifications based on the calculated secondary temperature.

In some implementations, the battery, when connected to the housing, forms an integral portion of the housing and wherein the battery includes an energy dense battery.

In some implementations, the battery includes a rechargeable battery configured to operate without recharge for a period of time in a range from approximately 4 hours to approximately 12 hours.

In some implementations, the rechargeable battery is configured to operate without recharge for a period of time approximately equal to 8 hours.

In some implementations, the housing includes a width in a range from approximately 60 millimeters to approximately 90 millimeters, a length in a range from approximately 100 millimeters to approximately 140 millimeters, and a depth in a range from approximately 20 millimeters to approximately 40 millimeters.

In some implementations, the housing includes a volume in a range from approximately 120 centimeters cubed to approximately 504 centimeters cubed.

In some implementations, the portable external device includes a weight in a range from approximately 0.25 kilograms to approximately 1.0 kilograms.

In some implementations, the portable external device further includes a latch configured to release the battery for removal from the housing, wherein the latch is configured to be actuated to release the battery for removal from the housing by at least two independent motions.

In some implementations, the latch includes two push buttons, each of which is biased into a locked position that inhibits removal of the battery from the housing, and both of which are configured to be pushed into an unlocked position simultaneously to release the battery for removal from the housing.

In some implementations, the two push buttons are arranged on opposing sides of the housing such that the two buttons are configured to be pushed in approximately opposite directions to one another.

In some implementations, the latch includes a channel and a post biased into a locked position toward a first end of the channel that inhibits removal of the battery from the housing, and wherein the post is configured to be pushed in at least two directions toward a second end of the channel into an unlocked position to release the battery for removal from the housing.

In some implementations, each of the battery and the power module is configured to power the implantable pump.

In some implementations, the energy dense battery includes a lithium-ion (Li-ion), nickel-metal hydride (NiMH), or nickel-cadmium (NiCd) rechargeable battery.

In some implementations, the energy dense battery includes an energy density in a range from approximately 455 watt-hours per liter to approximately 600 watt-hours per liter.

In some implementations, the power dense second battery includes a power density in a range from approximately 700 watts per liter to approximately 6 kilowatts per liter.

In some implementations, the portable external device further includes at least one piezoelectric speaker controlled by the power module to emit one or more audible sounds.

In some implementations, the portable external device further includes a first telemetry module configured to communicate information between the portable external device and one or more other devices according to a first wireless communication technique.

In some implementations, the portable external device further includes a second telemetry module configured to communicate information between the portable external device and one or more other devices according to a second wireless communication technique.

In some implementations, the first wireless communication technique is different than the second wireless communication technique.

In some implementations, the portable external device further includes a user interface includes a capacitive sensor configured to receive user input.

In some implementations, the portable external device further includes a depression in which the capacitive sensor is arranged.

In some implementations, power consumed by the power module is in a range from approximately 0.25 to approximately 1.25 watts.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIGS. 2A-E are a number of plan and elevation views illustrating an example of the control and power source module of FIG. 1.

FIGS. 13A and 13B illustrate another battery release latch mechanism that may be employed in conjunction with control and power source modules according to this disclosure.

FIGS. 14A-14D illustrate two other battery release latch mechanisms that may be employed in conjunction with control and power source modules according to this disclosure.

DETAILED DESCRIPTION

Present embodiments are directed to an external controller that may be configured to calculate parameters for sensing and acting on a condition, including a fault condition, during a power transfer in an implanted medical device. The medical device may be implanted in a subject and may include a device such as an artificial heart or ventricle assist device. The system measures at least one parameter and uses the at least one parameter to calculate a coupling coefficient for coils that transfer power between an external primary and an implanted secondary. The system uses the calculated coupling coefficient to estimate heat flux in the primary and secondary coils being generated in the system. Based on the level heat flux detected, the system may issue alerts to warn the subject or control actions to mitigate the effects of the heat flux.

Figure 1:
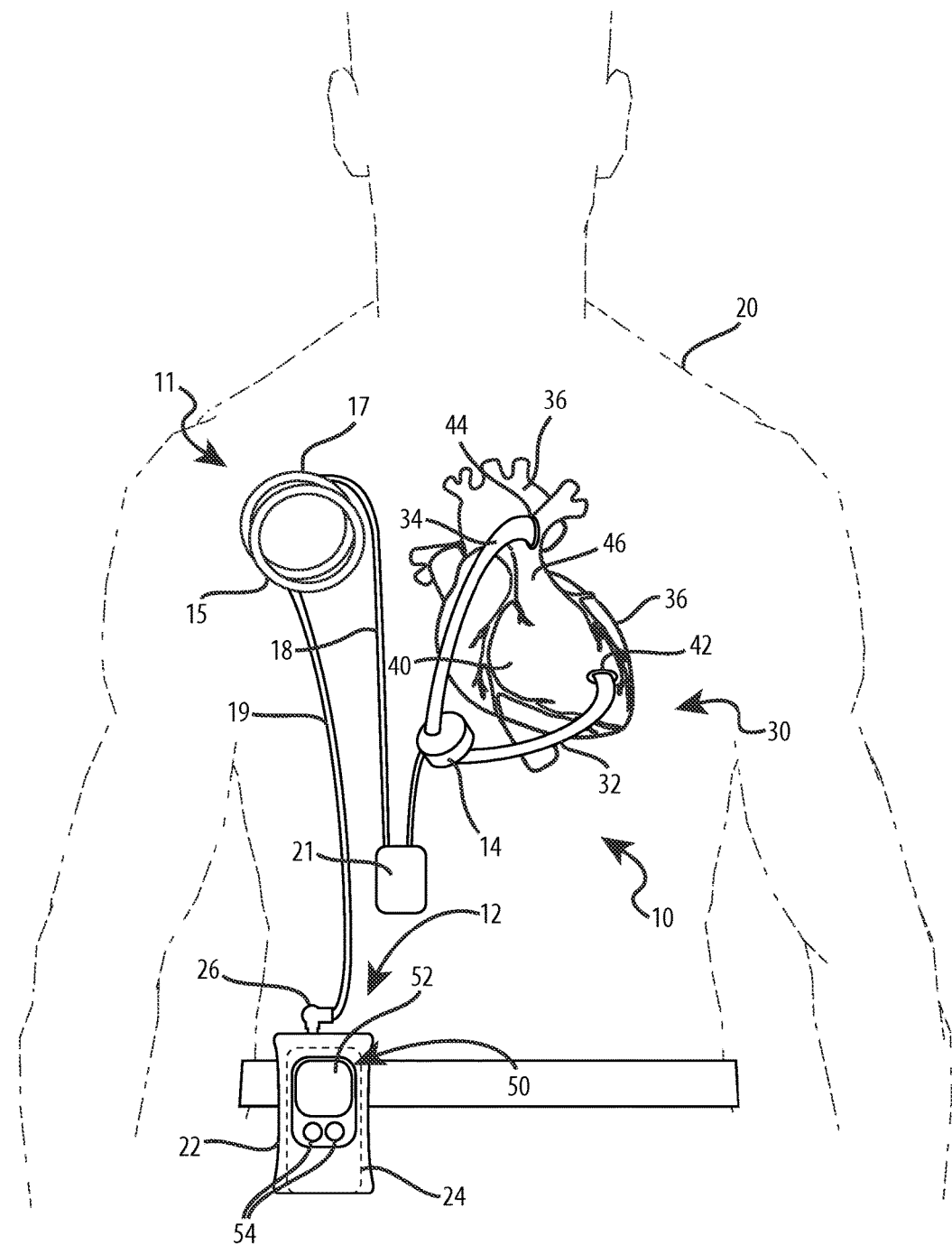
FIG. 1 is a conceptual diagram illustrating an example left ventricular assist device (LVAD) including a portable external control and power source module.

FIG. 1 is a conceptual diagram illustrating an example left ventricular assist device (LVAD) 10 including portable control and power source module 12 that is configured to provide electrical power to an implanted pump controller 21 and implanted pump 14 through a wireless power transfer system 11. Control and power source module 12 includes housing 22, an optional internal battery (see FIGS. 3 and 5), and removable battery 24 shown in FIG. 1. Control and power source module 12 also includes connector 26 and user interface 50. User interface 50 includes display screen 52 and input buttons 54, as well as a number of other elements described below with reference to FIG. 2B.

The wireless power transfer system 11 includes an external resonant network 15 that is disposed on the exterior of the patient 22 and an internal resonant network 17 that is implanted within the patient 22. The external resonant network 15 connects to the control and power source module 12 through an external cable 19. The internal resonant network 17 connects to an internal controller module 21 through an internal cable 18. The internal controller module 21 is generally configured to manage a power transfer that occurs across the external 15 and internal 17 resonant networks and to provide power and pump control to the implanted pump 14. In some implementations, the implant pump controller module 21 includes a battery that provides power to the implanted pump 14 when the power is not available through from across the external 15 and internal 17 resonant networks. In this implementation, the internal battery associated with the control and power source module 12 may be omitted and battery charging support is included within the implant pump controller. The operation on the TETS component 11 is described in greater detail below in connection with FIGS. 15-30.

As described in greater detail in the following examples, control and power source module 12 is a portable external device for a mechanical circulation support system that includes a controller for transferring power to implanted pump controller 21 and implanted pump 12, which is powered by a power source integral with the controller. The power source of example control and power source module 12 includes removable battery 24, which is removably connected to housing 22 of the control and power source module, and an internal back-up battery (see FIGS. 3 and 5) arranged within the housing. Control and power source module 12 is sized to accommodate a variety of wearable configurations for patient 20, including, e.g., being worn on a belt wrapped around the waist of patient 20 in FIG. 1.

The external 15 and internal 17 resonant networks connect control and power source module 12 and implanted pump controller 21 to communicate power and other signals between the external module and the implanted pump controller. In the example of FIG. 1, cable 19 connects to control and power source module 12 via connector 26. Cable 19 may be fabricated in a variety of lengths and may be employed to improve the flexibility of wearing control and power source module 12 on the body of patient 20. In one example, cable 19 may be itself extendable such that the cable can assume a number of different lengths. For example, cable 19 may be coiled such that stretching and unwinding the coiled cable extension will cause it to assume a number of different lengths. In another example, control and power source module 12 may include a mechanism from which cable 19 may be unwound and to which the extension may be rewound to cause it to assume a number of different lengths.

Control and power source module 12 also includes control electronics (not shown in FIG. 1) configured to control operation of various components of LVAD 10 including implanted pump controller 21, removable battery 24, the internal battery (see FIGS. 3 and 5), and user interface 50. As noted above, user interface 50 includes display screen 52 and input buttons 54. Display screen 52 may include a number of different types of displays, including, e.g., a liquid crystal display (LCD), dot matrix display, light-emitting diode (LED) display, organic light-emitting diode (OLED) display, touch screen, or any other device capable of delivering to and/or accepting information from a user. Display 52 may be configured to present text and graphical information in one or more colors. For example, display 52 may be configured to display the charge status of removable battery 24 and the internal battery of control and power source module 12, as well as present alarms to a user including instructions for taking action in response to the alarm. In an implementation where the internal battery associated with the control and power source module 12 is omitted, the display 52 may be configured to display the charge status of the implanted battery included within the implant pump controller 21. In one example of control and power source module 12, input buttons 54 are non-contact capacitive sensors configured to indicate input from a user without the user actually touching the buttons or any other part of the control and power source module.

Pump 14 of LVAD 10 may be surgically implanted within patient 20 including, e.g., in the abdominal cavity of the patient as illustrated in the example of FIG. 1. In other examples, pump 14 may be implanted in other locations within patient 20. Pump 14 is connected to heart 30 of patient 20 by inlet and outlet cannula 32, 34. In the example LVAD 10 of FIG. 1, inlet cannula 32 communicates blood from left ventricle 36 (LV) of heart 30 pump 14. Outlet cannula 34 communicates blood from pump 14 to aorta 38 of patient 20. Pump 14 includes a rigid housing formed from or with a biocompatible material or coating that resists corrosion and degradation from bodily fluids. Examples of suitable biocompatible materials include titanium and biologically inert polymers. Pump 14 may include a variety of types of positive displacement mechanisms capable of drawing blood into and ejecting the blood out of the pump. For example, pump 14 may include one of a centrifugal impeller, peristaltic, electromagnetic piston, axial flow turbine pump, magnetic bearing rotary pump, pneumatic displacement pump or another positive displacement mechanism appropriate for use with implantable devices such as RVAD 10.

The implant pump controller 21 is generally configured to provide power and control inputs to the implanted pump 14 and/or other component of the LVAD 10. In one respect, the implant pump controller 21 includes a power circuit and a rectifier through which the controller 21 manages a power transfer that occurs across the external 15 and internal 17 resonant networks. In another respect, includes power transfer components through which the controller provides power to the implanted pump 14. The various components of the implant pump controller 21 including the power circuit, rectifier, and power transfer components are described in greater detail in connection with FIGS. 15 and 16.

In the example of FIG. 1, ventricular assist system 10 is illustrated assisting left ventricle 36 (LV) of heart 30 of patient 20. However, in other examples, the techniques disclosed may be employed in other types of mechanical circulation support (MCS) systems configurable to, e.g., assist right ventricle 40 in a right ventricular assist device (RVAD), as well as both ventricles 36, 40 in a biventricular assist device (BiVAD). As a general matter, therefore, the source of blood for example VADs may be described generally as the assisted ventricle, while the destination of the pressurized blood delivered by the control and power source module may be designated as the arterial vessel.

Referring again to FIG. 1, each of inlet and outlet cannulas 32, 34 may be formed from flexible tubine extending to left ventricle 36 and aorta 38, respectively. Inlet and outlet cannulas 32, 34 may be attached to tissue of left ventricle 36 and aorta 38, respectively, by, e.g., sutures to establish and maintain blood flow, and may include appropriate structure for such attachment techniques including, e.g. suture rings 42, 44. In any of the aforementioned LVAD, RVAD, or BiVAD configurations, inlet cannula 32 is anastomosed to the assisted ventricle (or ventricles), while outlet cannula 34 is anastomosed to the corresponding assisted arterial vessel, which for left ventricular assist is typically aorta 38 and for right ventricular assist is typically pulmonary artery 46.

FIGS. 2A-E are a number of plan and elevation views illustrating an example configuration of control and power source module 12 of FIG. 1. FIG. 2A is a front elevation view of example control and power source module 12. FIGS. 2B and 2C are left and right elevation views, respectively, of control and power source module 12. FIGS. 2D and 2E are top and bottom plan views, respectively, control and power source module 12. Control and power source module 12 includes housing 22, user interface 50, cable port 60, external power source port 62, battery release buttons 64 and 66, and removable battery bay door 68. User interface 50 includes display screen 52, input buttons 54, as well as mute button 70 and status indicators 72 and 74 illustrated in FIG. 2B.

Control and power source 12 includes a controller for controlling implanted pump 12 powered by a power source integral with the controller and is sized to accommodate a variety of wearable configurations for patient 20, including, e.g., being worn on a belt wrapped around the waist of the patient, as illustrated in FIG. 1. In one example, control and power source module 12, and, in particular, housing 22 is fabricated to specific size and weight targets to maintain the module at a size that facilitates flexibility and convenience for patient 20. For example, housing 22 of control and power source module 12 may be fabricated with a length, L, in a range from approximately 100 millimeters to approximately 140 millimeters, a width, W, in a range from approximately 60 millimeters to approximately 90 millimeters, and a depth, D, in a range from approximately 20 millimeters to approximately 40 millimeters. Control and power source module 12 may also be sized based on a total volume of the device. For example, housing 22 of control and power source module 12 may be fabricated to include a volume in a range from approximately 120 centimeters cubed to approximately 504 centimeters cubed. In one example, in addition to or in lieu of specific size targets, control and power source module 12 may also include a target weight. For example, control and power source module 12, including removable battery 24 and the internal battery (not shown in FIGS. 2A-E) may be fabricated to include a weight in a range from approximately 0.4 kilograms to approximately 0.8 kilograms.

The size and weight of control and power source module 12 may depend, at least in part, on the components of which the device is comprised, including, e.g. housing 22, display 52, removable battery 24 and in the internal battery, as well as the control electronics arranged within the housing of the device. In one example, the electronics of control and power source module 12 may include, e.g., one or more processors, memory, telemetry, charging circuitry, speakers, power management circuitry, and power transfer circuitry. In any event, the size and weight of the internal components of control and power source module, including, e.g., display 52, status indicators 72 and 74, and the internal electronics of the device, may be proportional to the energy required to power the components. Thus, reducing the energy requirements of the electronics of control and power source module 12 may not only serve to extend battery life, but may also reduce the size and weight of the device.

In another example, control and power source module 12 may be configured such that the power consumed by the electronics of the control and power source module is equal to a target value. For example, the electronics of control and power source module 12 may be configured to consume power in a range from approximately 0.25 to approximately 1.25 watts.

Example control and power source module 12 of FIGS. 2A-2E includes user interface 50, including display screen 52, input buttons 54, mute button 70 and status indicators 72 and 74. Display screen 52 may include a number of different types of displays, and may be configured to present text and graphical information in one or more colors. In one example, input buttons 54 are non-contact capacitive sensors configured to indicate input from a user without the user actually touching the buttons or any other part of the control and power source module. Although input buttons 54 may, in one example, include non-contact sensors, the buttons may be arranged in depressions 76 in housing 22 provide tactile feedback to a user searching for or using the buttons to view information on display 52 and otherwise interact with control and power source module 12. In one example, input buttons 54 may be soft keys configured to execute different functions on control and power source module 12 based on, e.g., current functions and contexts indicated on display 52. In such examples, the current function associated buttons 54 operating as soft keys may be presented as labels on display 52 just above each of the buttons. In one example, input buttons 54 correspond to two main functions for interacting with control and power source module 12. For example, one of input buttons 54 may function as a "home" button that, when activated by a user, navigates to a default screen presented on display 52 of user interface 50. Additionally, in such an example, the other one of input buttons 54 may function as a "next" button that, when activated by a user, toggles to the next screen in a series of possible screens that may be presented on display 52 of user interface 50.

As illustrated in FIG. 2E, user interface 50 of control and power source module 12 also includes mute button 70 and status indicators 72 and 74. In one example, mute button 70 may be configured to, when depressed, mute audible alerts issued by speakers of control and power source module 12. Mute button 70 may, in one example, only mute alerts temporarily, for example to allow patient 20 to leave a public place with other people that may be disturbed by the alert issued by speakers of control and power source module 12. In one example, status indicators 72 and 74 may be lighted, e.g. LED lighted windows that indicate the operating status of control and power source module 12 and/or implanted pump 14. For example, status indicator 72 may be illuminated to indicate that control and power source module 12 and/or implanted pump 14 are operating normally without error. Status indicator 74, on the other hand, may be illuminated to indicate one or more alarm states that indicate errors or other actionable states of control and power source module 12 and/or implanted pump 14. For example, status indicator 74 may be illuminated to indicate the state of removable battery 24 and/or the internal battery of control and power source module 12 as at or below a threshold charge level. In some examples, status indicator 74 may be illuminated in a variety of manners to indicate different states of control and power source module 12 and/or implanted pump 14, including being illuminated in different colors to indicate alarm states of removable battery 24 and/or the internal battery and/or the implant battery of different levels of severity.

Example control and power source module of FIGS. 2A-2E also includes cable port 60, external power source port 62, and battery release buttons 64 and 66. Cable port 60 may be configured to receive cable 19 via connector 26 as illustrated in FIG. 1. External power source port 62 may be configured to receive one or more types of external power source adaptors, e.g. an AC/DC or DC/DC adaptor configured to charge removable battery 24 and/or the internal battery of control and power source module 12.

As will be described in greater detail with reference to FIGS. 3 and 4, control and power source module 12 includes a latch configured to release removable battery 24 from housing 22. The battery release latch of control and power source module may be, in one example, configured to be actuated to release removable battery 24 from housing 22 by at least two independent motions. In FIGS. 2A-2E, the battery release latch of control and power source module 12 includes battery release buttons 64 and 66. In one example, battery release buttons 64 and 66 are biased into a locked position that inhibits removal of removable battery 24 from housing 22 and are configured to be pushed into an unlocked position simultaneously to release the first power source for removal from the housing. In the example control and power source module 12 of FIGS. 2A-2E, battery release button 64 is arranged on right side (from the perspective of the views of FIGS. 2A-2E) of housing 22 and battery release button 66 is arranged on opposing left side of housing 22 such that the two buttons are configured to be pushed in approximately opposite directions to one another.

Figure 3:
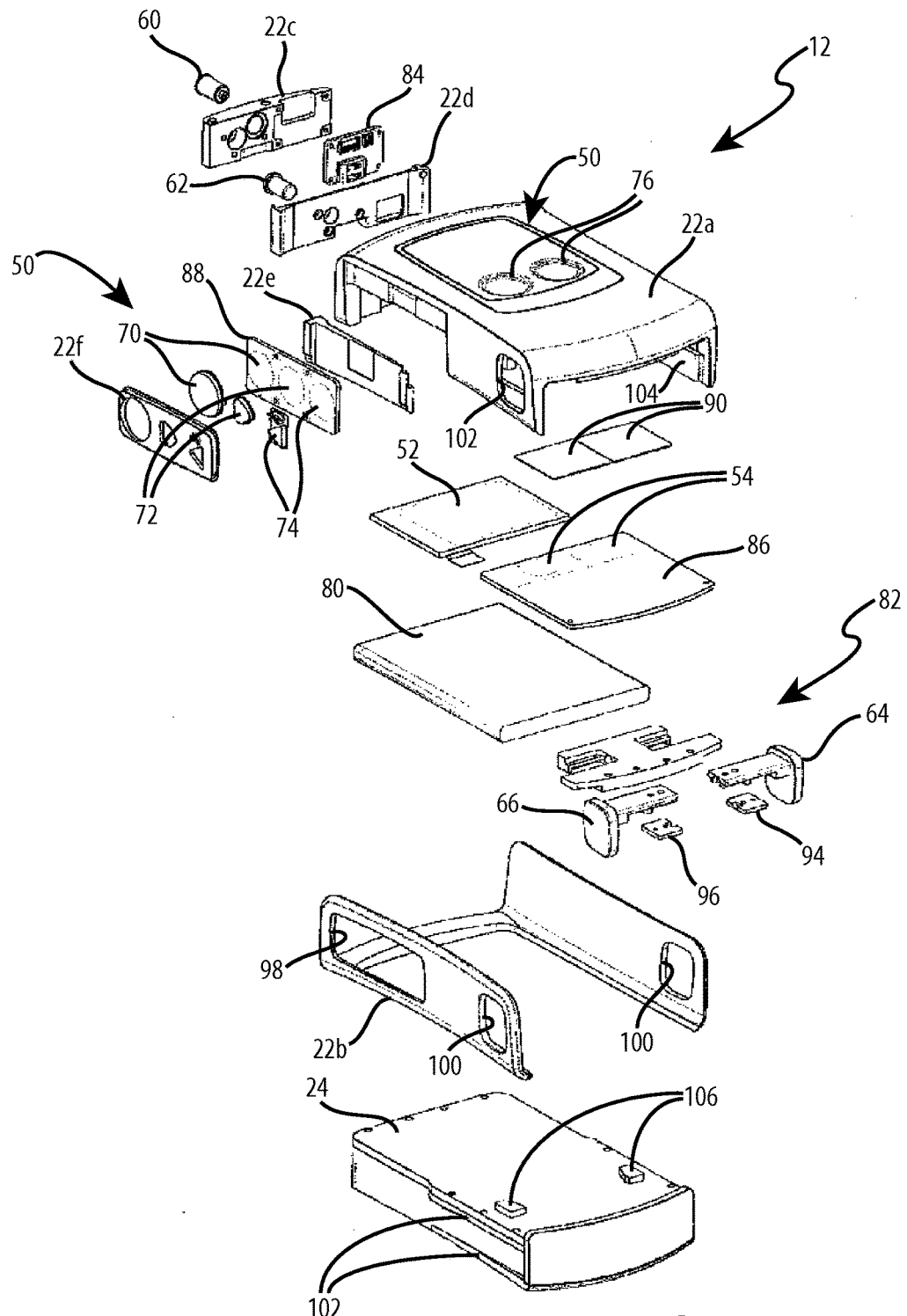
FIG. 3 is an exploded view of the example control and power source module of FIGS. 2A-2E.

FIG. 3 is an exploded view of example control and power source module 12 of FIGS. 2A-2E. Example control and power source module 12 includes housing 22, removable battery 24, internal battery 80, user interface 50, cable port 60, external power source port 62, battery release latch 82, circuit boards 84, 86, and 88, and speakers 90. Housing 22 includes a number of pieces, including front shield 22a, sides and back shield 22b, top cap 22c, main board backing 22d, status indicator backing 22e, and status indicator bezel 22f. As illustrated in FIG. 3, removable battery 24 forms part of the back of control and power source module 12. Housing 22 of control and power source module 12, including one or more of front shield 22a, sides and back shield 22b, top cap 22c, main board backing 22d, status indicator backing 22e, and status indicator bezel 22f may be fabricated from a variety of materials, including, e.g., plastics including acrylonitrile butadiene styrene (ABS), polyvinyl siloxane (PVS), silicone, metals including stainless steel, aluminum, titanium, copper, and composites including carbon fiber, glasses, and ceramics. In some examples different portions of housing 22, including front shield 22a, sides and back shield 22b, top cap 22c, main board backing 22d, status indicator backing 22e, and status indicator bezel 22f may be fabricated from the same materials. In another example, however, different portions of housing 22, including one or more of front shield 22a, sides and back shield 22b, top cap 22c, main board backing 22d, status indicator backing 22e, and status indicator bezel 22f may be fabricated from different materials.

In one example, front shield 22a of housing 22 may include a metallic bezel partially or completely surrounding display 52 of user interface 50. The metallic bezel may be fabricated from a variety of thermally conductive materials including, e.g., aluminum, copper, and alloys thereof. The metallic bezel of front shield 22a of housing 22 may be configured to provide thermal conductance of heat generated by one or more of circuit boards 84, 86, and 88, as well as internal battery 80 and/or removable battery 24. In one example, a metallic bezel of front shield 22a is configured to sink heat generated by circuit board 86 associated with user interface 50. The metallic portion of front shield 22a may be thermally coupled to circuit board 86 to increase thermal conduction between the two components, e.g., using a thermally conductive pad, potting material, or a thermal grease interposed between the shield and the circuit board. In a similar manner to front shield 22a, indicator bezel 22f may be configured, in one example, to provide thermal conductance of heat generated by circuit board 88. In such an example, indicator bezel 22f may be fabricated from a variety of thermally conductive materials including, e.g., aluminum, copper, and alloys thereof and may be thermally coupled to circuit board 88 to increase thermal conduction between the two components, e.g., using a thermally conductive pad, potting material, or a thermal grease interposed between the shield and the circuit board.

User interface 50 of control and power source module includes display 52, input buttons 54, mute button 70, and status indicators 72 and 74. Battery release latch 82 includes base 92, right and left push buttons 64 and 66, respectively, and right and left back plates 94 and 96, respectively. Control and power source 12 includes a number of circuit boards, including main board 84, display board 86, and status indicator board 88, one or more of which may be connected to one another. In one example, main board 84 includes the main control electronic components for control and power source module 12, including, e.g. processor(s), memory, telemetry, charging, and power management electronics. Display board 86 includes input buttons 54 and may include other electronics associated with the function of display 52. Additionally, status indicator board 88 may include a number of electronic components associated with mute button 70 and status indicators 72 and 74.

In FIG. 3, main board backing 22d is configured to be connected to front shield 22a and to secure main board 84 and to help secure cable port 60 and external power source port 62, along with top cap 22c. Main board 84 is interposed between top cap 22c and main board backing 22d. Cable port 60 and external power source port 62 are received by apertures in top cap 22c and main board backing 22d. Status indicator board backing 22e is configured to be connected to front shield 22a and to secure status indicator board 88 to housing 22 of control and power source module 12. Status indicator board 88 may be connected to backing 22e. Each of mute button 70 and status indicators 72 and 74 are comprised of a user interface component configured to be received by bezel 22f and an electronic component on status indicator board 88. In the example of FIG. 3, mute button 70 includes a push button received in an aperture of bezel 22f and a contact or non-contact sensor on indicator board 88. In the example of FIG. 3, status indicators 72 and 74 each include a lens configured to be received in a corresponding aperture in bezel 22f and a light emitter, e.g. an LED on status indicator board 88. Status indicator board 88 and the push button of mute button 72 and lenses of indicators 72 and 74 are interposed between main board backing 22e and bezel 22f.

The sides of shield 22b are configured to mate with and overlay the sides of front shield 22a of housing 22 of control and power source module 12. Sides and back shield 22b includes apertures 98 and 100. Aperture 98 is configured to receive bezel 22f. Apertures 100 are configured to receive buttons 64 and 66 of battery release latch 82 and to be aligned with corresponding apertures 102 in front shield 22a, only one of which can be seen in the view of FIG. 3. Removable battery 24 is connected to housing 22 and configured to be released by battery release latch 82. In particular, tabs 104 on removable battery 24 is configured to be received on rails 106 on the interior of front shield 22a such that the battery may slide into and out of a locked connection with housing 22 of control and power source module 12 via battery release latch 82. Display 52, display board 86 including input buttons 54, speakers 90, internal battery 80, and battery release latch 82 are configured to be arranged within housing 22 of control and power source module over removable battery 24. Base 92 of battery release latch 82 is configured to be fastened to front shield 22a and to slidably receive right and left push buttons 64 and 66 and back plates 94 and 96. Display 52 is generally aligned with a window in front shield 22a and input buttons 54 on display board 86 are generally aligned with depressions 76 in the front shield of housing 22 of control and power source module 12.

In some examples, control and power source module 12 may employ a variety of waterproofing techniques and mechanisms for protecting various components of the device from ingress or egress of one or more materials into or out of housing 22. In one example, removable battery 24 may be electrically coupled with one or more of circuit boards 84, 86, and 88 with, e.g. a multi-pin connection that employs a gasket to seal the releasable connection between battery 24 and the inner components of control and power source module 12 from ingress of materials into housing 22. Such a gasket may be fabricated from a variety of materials, including, e.g. a compressible polymer or an elastomer, e.g. rubber. In one example, one or more parts of housing 22, e.g. one or more of front shield 22a, sides and back shield 22b, top cap 22c may be hermetically sealed. For example, front shield 22a, sides and back shield 22b, top cap 22c may be connected to form enclosed housing 22 by gasket(s), sonic welding or adhesives.

In one example, speakers 90 are piezoelectric speakers that are configured to be fastened, e.g. with an adhesive to an interior surface of front shield 22a of housing 22 of control and power source module 12. Piezoelectric speakers may include a piezoelectric crystal coupled to a mechanical diaphragm. Sound is produced by alternatively applying and removing an electrical signal to the crystal, which responds by flexing and unflexing the mechanical diaphragm in proportion to the voltage applied across the crystal's surfaces. The action of flexing and unflexing the mechanical diaphragm at relatively high frequencies produces vibrations in the diaphragm that emit an audible sound, e.g. sounds in a frequency range from approximately 150 Hz to approximately 4 kHz.

In some examples, a portion of housing 22 may be configured to act in conjunction with speakers 90 to effectively increase the amplitude of the sounds emitted by the speakers. For example, the geometry of a portion of front shield 22a of housing 22 to which speakers 90 are connected may be shaped and sized to cause the shield to resonate in response to vibration of the speakers. For example, the portion of front shield 22a of housing 22 to which speakers 90 are connected may be shaped and sized such that the natural frequency of the combination of housing and speakers modulated to a target frequency within the operational range of the speakers. Controlling speakers 90 to operate at a particular frequency may then cause the speakers and portion of front shield 22a to resonate, thereby effectively increasing the amplitude of the sounds emitted by the speakers. In one example, speakers 90 include piezoelectric speakers that generally perform better above 1000 Hz. As such, the natural frequency of the combination of the portion of front shield 22a to which speakers 90 are attached and the speakers may be modulated to greater than 1000 Hz.

Modulating the housing of a control and power source module to particular resonant frequencies may be accomplished by a number of analytical, numerical, and experimental methods. In one example, the resonant frequency of a housing of a control and power source module may be modulated analytically using theory for thin, elastic plates to determine a starting point for geometry and material properties of the housing. In another example, the resonant frequency of a housing of a control and power source module may be modulated numerically using finite element analysis (FEA) modeling to simulate the vibration characteristics of different modeled geometries. Additionally, a number of processes and techniques, such as Chladni patterns, may be employed to experimentally refine the natural frequency of the housing with the speakers.

Although the example of FIG. 3 includes two speakers 90, other examples may include more or fewer speakers configured to emit audible sounds, e.g. alarms to a user of control and power source module 12. In one example, a control and power source module according to this disclosure includes one speaker. In another example, a control and power source module according to this disclosure includes four speakers.

Figure 4A:
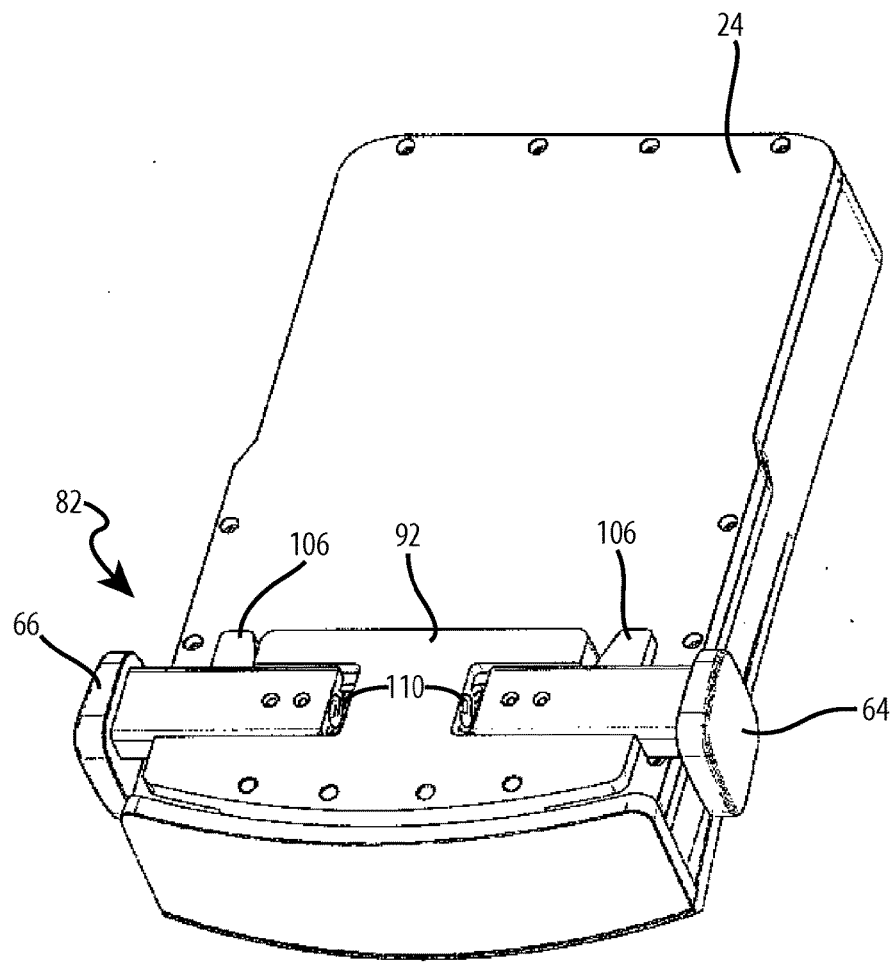
FIGS. 4A and 4B are perspective views of the battery release latch of the example control and power source module of FIGS. 2A-3.
Figure 4B:
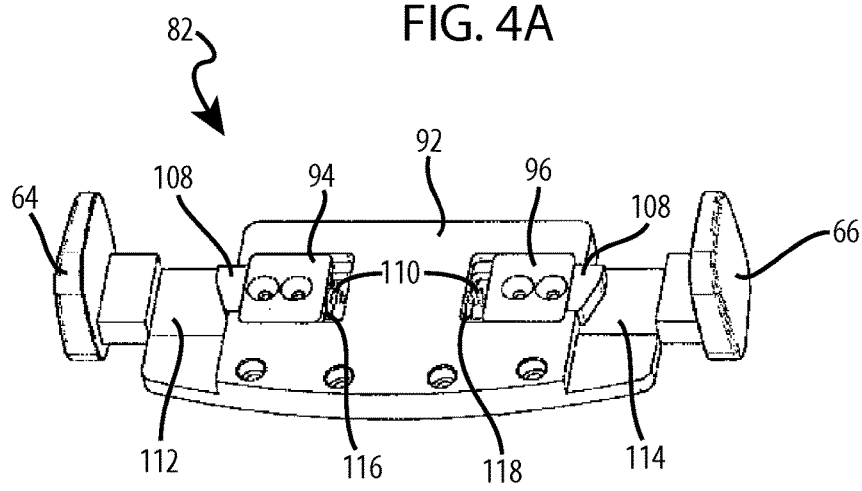

FIGS. 4A and 4B are perspective views of removable battery 24 and battery release latch 82 of control and power source module 12. Removable battery 24 includes stops 106 configured to engage catches 108 on battery release latch 82 to lock the battery in housing 22 of control and power source module 12. Battery release latch 82 includes base 92, right and left push buttons 64 and 66, respectively, right and left back plates 94 and 96, respectively, catches 108, and springs 110.

In FIGS. 4A and 4B, flanges 112 and 114 protrude from push buttons 64 and 66, respectively, and are received by slots 116 and 118, respectively, in base 92. Back plates 94 and 96 are also received by slots 116 and 118 and are fastened to flanges 112 and 114 to slidably connect push buttons 64 and 66, respectively, to base 92 of battery release latch 82. Springs 110 are interposed between a face of slots 116 and 118 of base 92 and connected flanges 112 and 114 and back plates 94 and 96. Springs 110 may function to bias push buttons 64 and 66 into a locked position that inhibits removal of battery 24 from housing 22 of control and power source module 12. In the example of FIGS. 4A and 4B, springs 110 are configured to bias push buttons 64 and 66 laterally outward, in generally opposing directions away from the outer surfaces of removable battery 24 such that catches 108 engage stops 106 on removable battery 24 to inhibit the battery from being removed from housing 22 of control and power source module 12. To release battery 24 from housing 22 of control and power source module 12, both of push buttons 64 and 66 are pushed laterally inward, in generally opposing directions toward the interior region of removable battery 24 such that catches 108 move out of engagement with stops 106 on removable battery 24. In one example, control and power source module 12 may be configured with a second mechanical latching mechanism for battery 24. For example, battery 24 may be received in housing 22 of control and power source module 12 with a friction fit such that a user must apply a threshold force, e.g. 1 pound force to remove the battery from the housing.

Although the example control and power source module 12 described and illustrated with reference to FIGS. 2A-4 includes battery release latch 82 including push buttons 64 and 66, in another example according to this disclosure the latch may be triggered by another mechanism that requires two independent motions to release a removable battery from a control and power source module. In one example according to this disclosure, a battery release latch actuated by at least two independent motions and configured to release a removable power source from a housing of a control and power source module may include a channel and a post biased into a locked position toward a first end of the channel that inhibits removal of the power source from the housing. In such an example, the post may be configured to be pushed in at least two directions toward a second end of the channel into an unlocked position to release the removable power source from the housing of the control and power source module. FIGS. 4C-4H illustrate a number of particular alternative latching mechanisms that may be employed in conjunction with control and power source modules according to this disclosure. In each of the examples of FIGS. 4C-4H, the control and power source module includes a removable battery that may be released from and locked to a housing by the respective example latching mechanisms. Additionally, the direction in which the removable battery may be released from the control and power source module in the illustrated examples is indicated in each of the figures by arrow R.

Figure 4C:
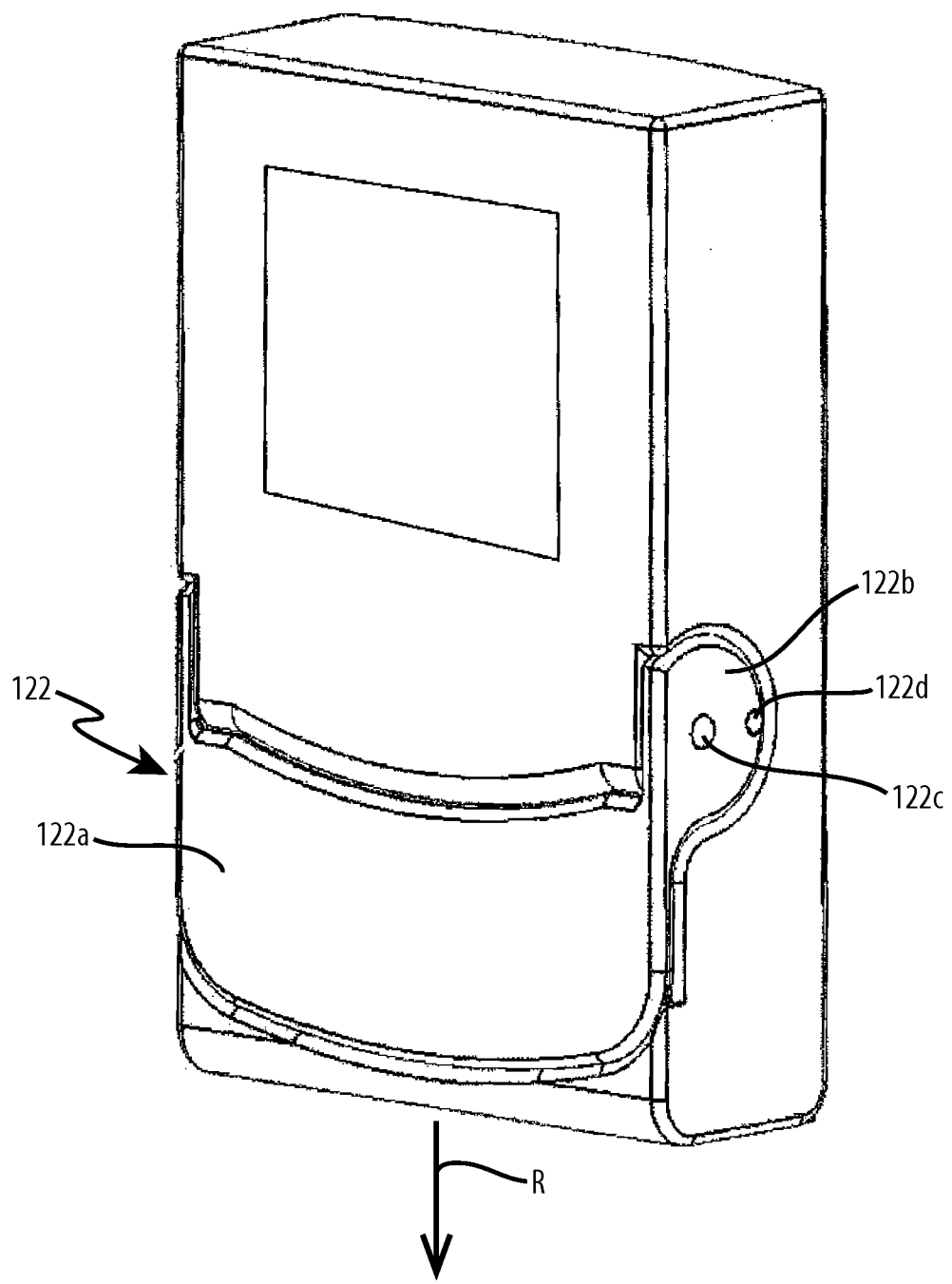
FIGS. 4C-4H illustrate a number of alternative battery release latch mechanisms that may be employed in conjunction with control and power source modules according to this disclosure.

FIG. 4C is a perspective view of a control and power source module including battery release latch 122. Battery release latch 122 includes paddle 122a, two flanges 122b (only one of which is viewable FIG. 4C), pivot 122c and cam 122d. In FIG. 4C, paddle 122a and flanges 122b are pivotably connected to the control and power source module at pivot 122c. Cam 122d is a protrusion extending inward from paddle 122b. Latch 122 may be actuated by rotating paddle 122a away from the control and power source module, which causes flanges 122b to rotate about pivot 122c. Flanges 122b turn cam 122d, which may be received within a channel in the removable battery. Rotating cam 122d pushes against the removable battery such that the battery is pushed downward and out of engagement with the control and power source module. When the battery, or a new or replacement removable battery is reinserted into the control and power source module of FIG. 4C a channel in the battery may engage cam 122d and rotating paddle 122a, which, in turn, rotates flanges 122b, may cause the cam to draw the battery into the housing and lock the battery in place. In one example of latch 122, paddle 122a may be releasably secured to the housing of the control and power source module to prevent inadvertent actuation of the latch. For example, paddle 122a may be held to the housing by a small permanent magnet.

Figure 4D:
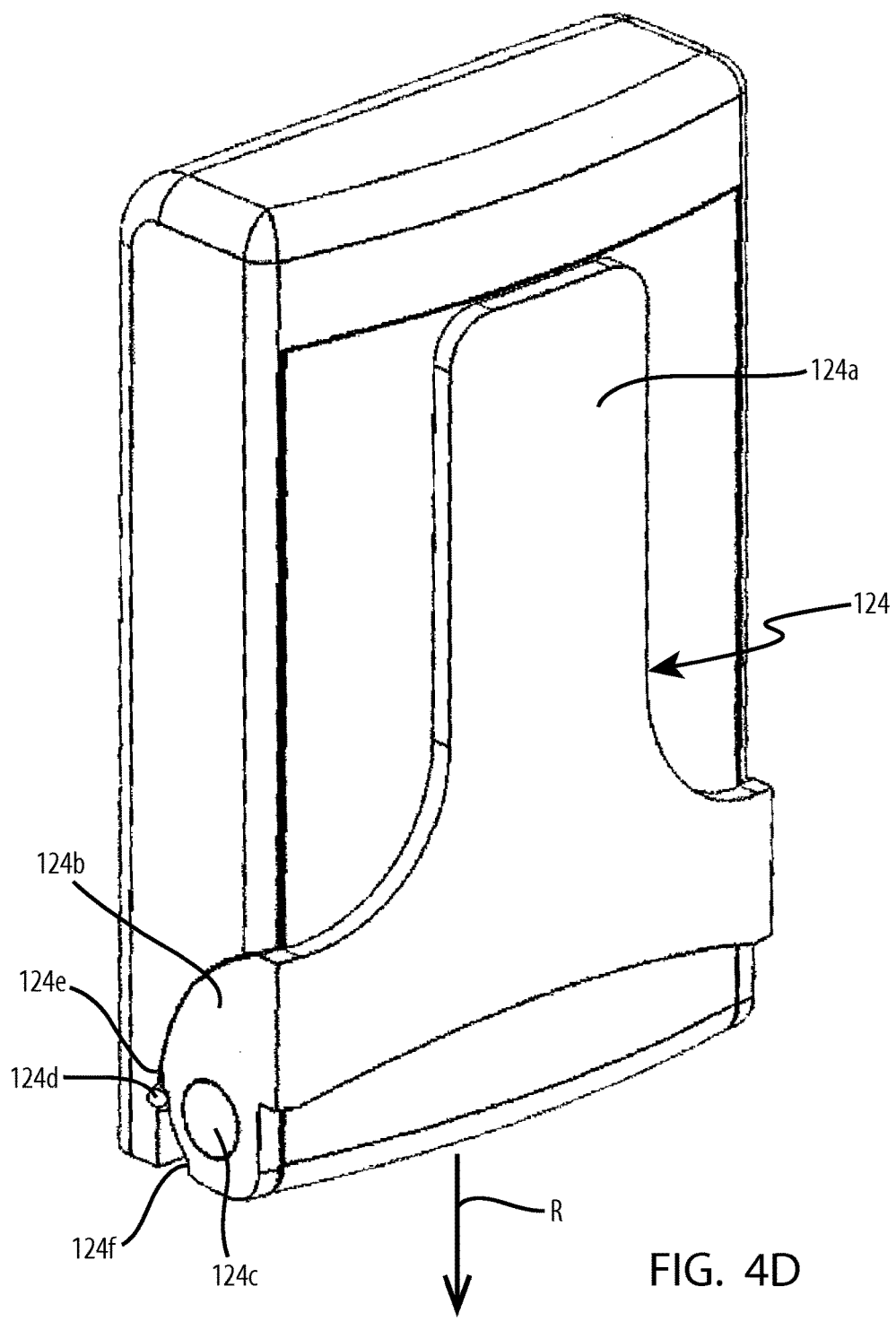

FIG. 4D is a perspective view of a control and power source module including battery release latch 124. Battery release latch 124 includes paddle 124a, two flanges 124b (only one of which is viewable FIG. 4C), pivot 124c and post 124d. Flanges 124b each include two landings 122e, 122f, which are configured to engage post when the removable battery is released and locked into the control and power source module of FIG. 4D. In FIG. 4D, paddle 124a and flanges 124b are pivotably connected to the removable battery of the control and power source module at pivot 124c. Post 124d protrudes from the housing of the control and power source module. Latch 124 may be actuated by rotating paddle 124a away from the control and power source module, which causes flanges 124b to rotate about pivot 124c. Flanges 124b turn until release landing 124f engages post 124b. As paddle 124a and flanges 124c continue to rotate, landing 124f pushes against post 124b, which causes the latch and removable battery to be released from the housing of the control and power source module. When the battery, or a new or replacement removable battery is reinserted into the control and power source module of FIG. 4D, the battery and latch 124 may be pushed into the housing until landing 124f engages post 124d, after which paddle 124a and flanges 124b may be rotated until lock landing 124e engages post 124d. As paddle 124a and flanges 124c continue to rotate, landing 124e pushes against post 124b, which causes the latch and removable battery to be pulled into and locked to the housing of the control and power source module. In one example of latch 124, paddle 124a may be releasably secured to the housing of the control and power source module to prevent inadvertent actuation of the latch. For example, paddle 124a may be held to the housing by a small permanent magnet.

Figure 4E:
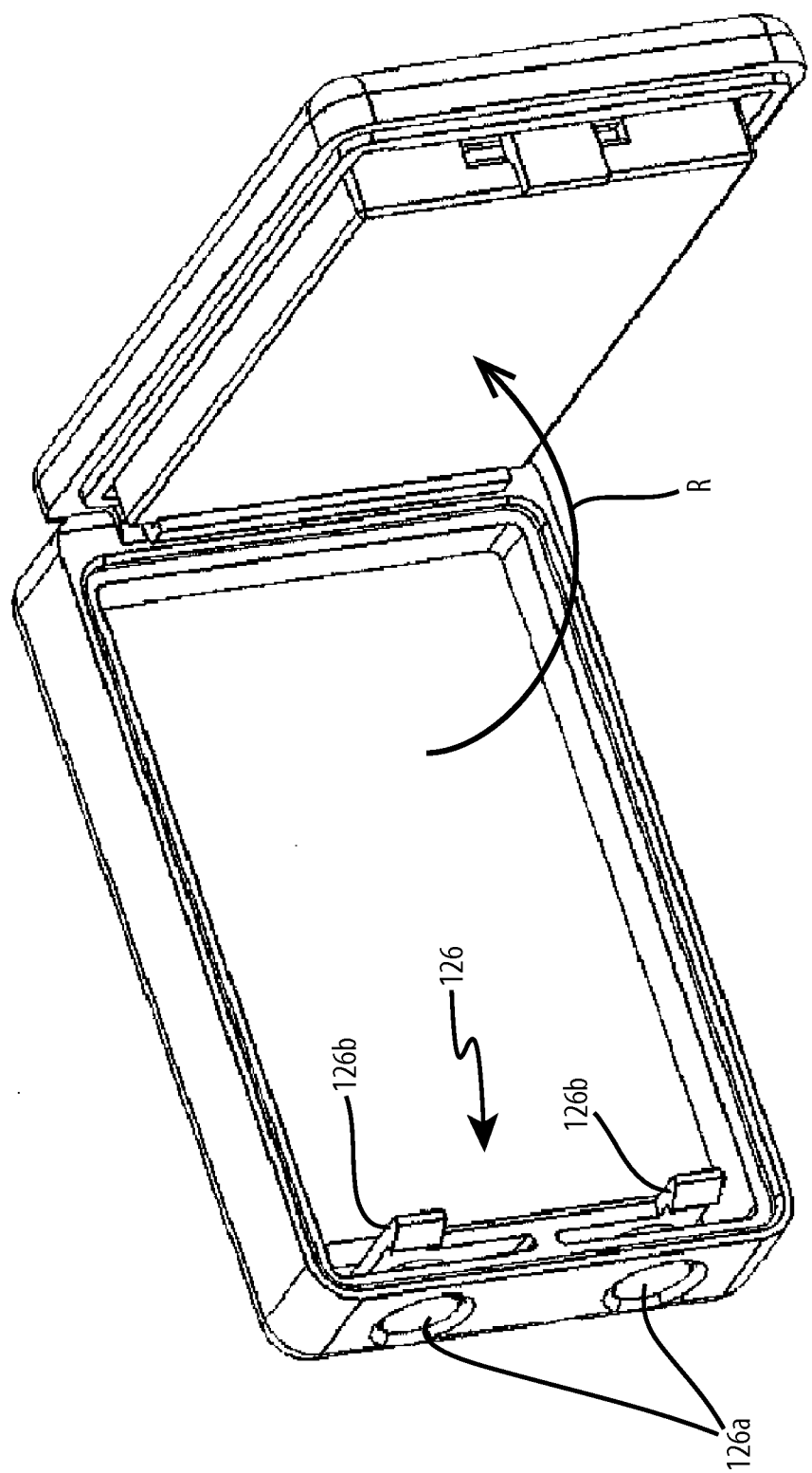

FIG. 4E is a perspective view of a control and power source module including battery release latch 126. The control and power source module of FIG. 4E includes a clam shell design including two halves pivotably connected to one another. Battery release latch 126 includes two buttons 126a and two clips 126b. In FIG. 4E, buttons 126a and clips 126b are connected to the housing of the control and power source module. Buttons 126a are configured to cause clips 126b to move into and out of engagement with catches in the other half of the clam shell housing of the control and power source module of FIG. 4E. Latch 126 may be actuated by pushing both of buttons 126a simultaneously to cause both clips 126b to move out of engagement with respective catches in the other half of the clam shell housing. In one example, the interior surface of the half of the housing opposite clips 126b may include slots that are configured to receive the clips.

Figure 4F:
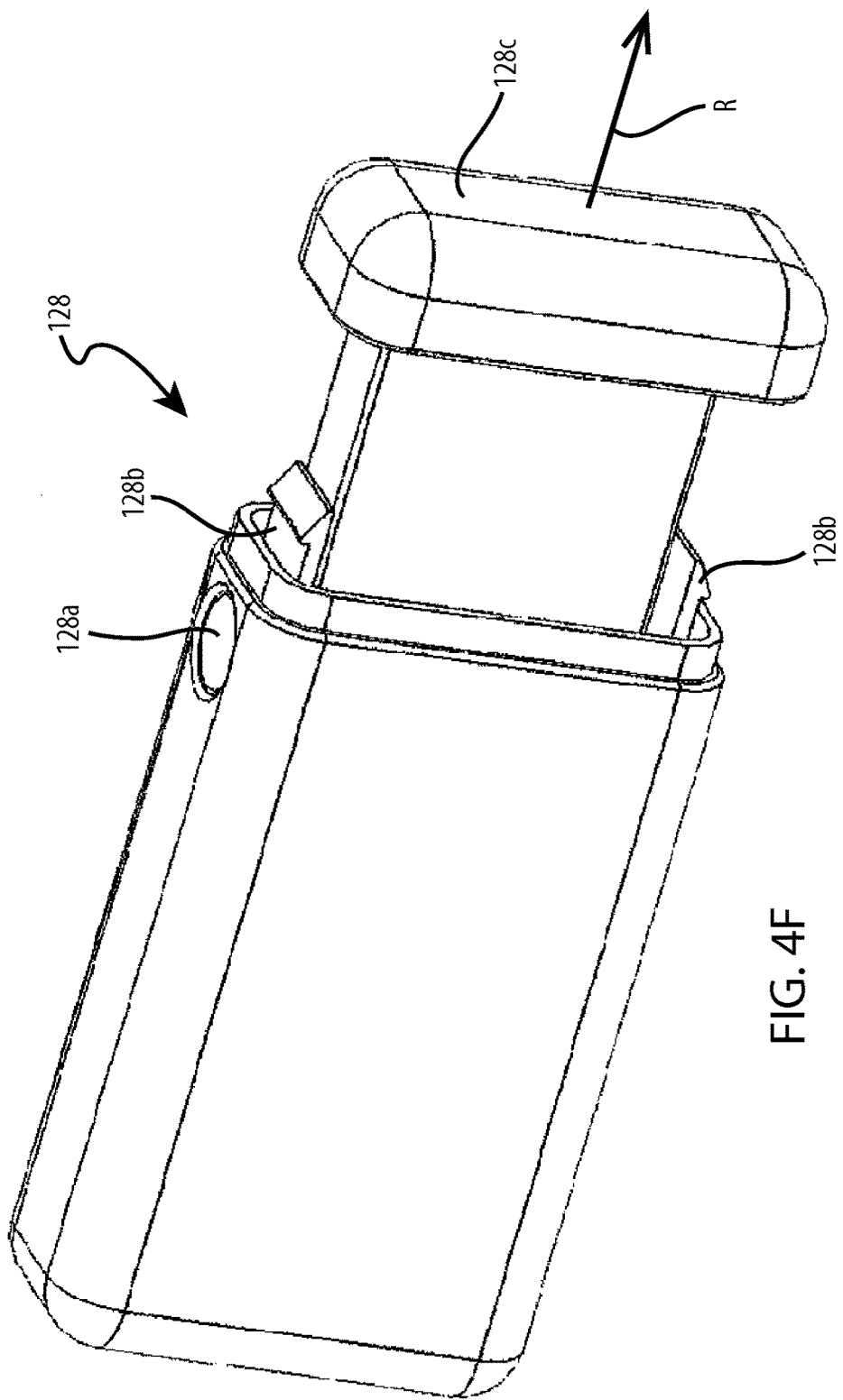

FIG. 4F is a perspective view of a control and power source module including battery release latch 128. Battery release latch 128 includes two buttons 128a and two clips 128b. In FIG. 4F, buttons 128a and clips 128b are connected to the housing of the control and power source module. Buttons 128a are configured to cause clips 128b to move into and out of engagement with catches in cap 128c of the housing of the control and power source module of FIG. 4E. Latch 128 may be actuated by pushing both of buttons 128a simultaneously to cause both clips 128b to move out of engagement with respective catches in cap 128c of the housing. In one example, the interior surface of cap 128c of the housing may include slots that are configured to receive the clips.

Figure 4G:
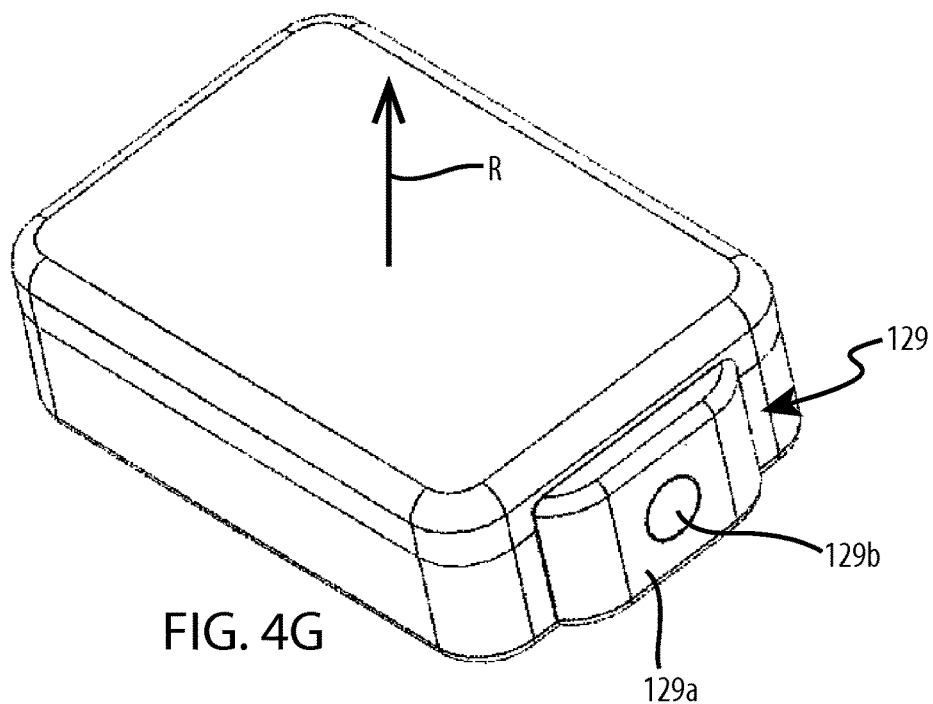
Figure 4H:
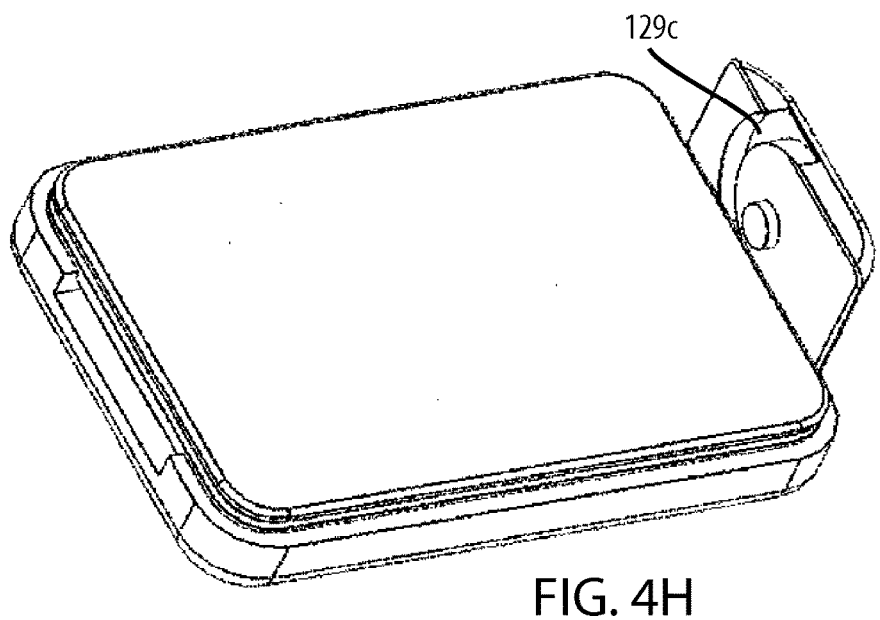

FIGS. 4G and 4H are perspective views of a control and power source module including battery release latch 129. Battery release latch 129 includes knob 129a, pivot 129b, and channel 129c. In FIGS. 4G and 4H, knob 129a is pivotably connected to the housing of the control and power source module at pivot 129b. The removable battery of the control and power source module of FIGS. 4G and 4H includes a post that protrudes from one end of the battery and is configured to be received in channel 129c. Latch 129 may be actuated to release the battery by rotating knob 129a about pivot 129b. In one example, knob 129a is rotated approximately 180 degrees about pivot 129b. Channel 129c is configured to push on the post protruding from the battery as knob 129a is rotated such that the battery is gradually released upward away from the housing. After rotating knob 129a completely, e.g. 180 degrees, the post in the battery may be released from channel 129c to release the battery from the housing of the control and power source module.

Figure 5:
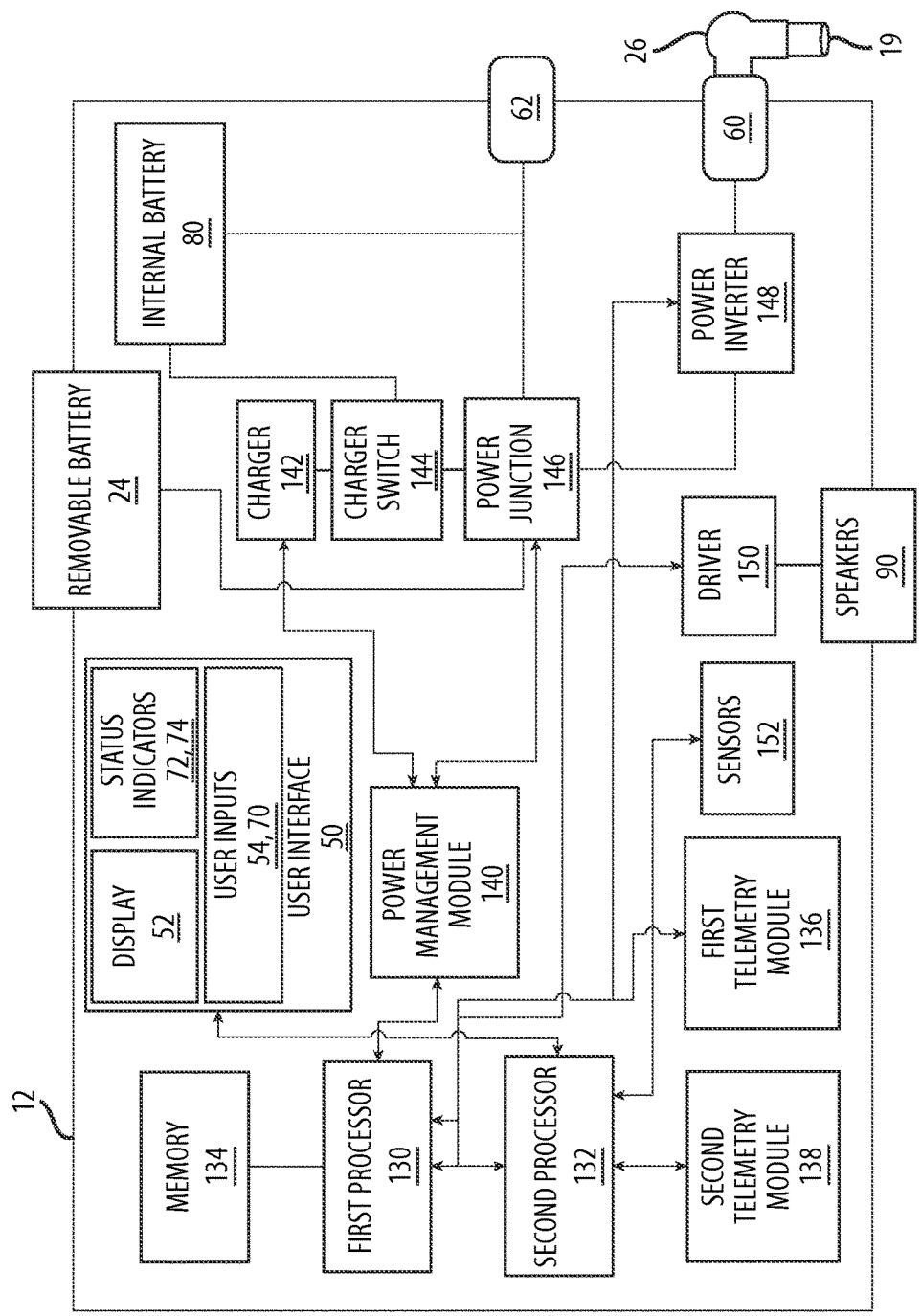
FIG. 5 is functional block diagram illustrating an example control and power source module according to this disclosure.

FIG. 5 is a functional block diagram illustrating components of an example of control and power source module 12, which includes removable battery 24, internal battery 90, cable port 60 connected to cable 19 via connector 26, external power source port 62, speakers 90, and a variety of electronics. The electronics of control and power source module 12 include first processor 130, second processor 132, memory 134, first telemetry module 136, second telemetry module 138, power management module 140, charger 142 and charger switch 144, power junction 146, and power transfer inverter or power bridge 148. Control and power source module 12 includes speakers 90 driven by driver 150 for emitting audible sounds, such as alarms to patient 20 or a caregiver, such as a clinician. As illustrated in the example of FIG. 5, control and power source module 12 may also include one or more sensors 152, including, e.g. motion or light sensors. In one example, sensors 152 includes an ambient light sensor that is configured to automatically adjust the contrast and/or brightness of display 52 of user interface 50 based on current ambient light conditions.

Control and power source module 12 is configured to provide uninterrupted power to components of a VAD, e.g. implanted pump 14, by employing one removable battery 24 as a primary power source and internal battery 80 as a back-up to bridge operation of the control and power source module components during recharge of removable battery 24. Internal battery 80 may be non-removably connected to control and power source module 12 in the sense that it is not configured to be removed and replaced by users during normal operation of the device. In some examples, internal battery 80 may, of course, be removed from control and power source module 12, e.g. by disassembling the device and disconnecting the internal battery from the internal circuitry of the device. In one example, one or both of removable battery 24 and internal battery 80 of control and power source module 12 may include, e.g., rechargeable lithium-ion (Li-ion), lithium polymer (Lipoly), nickel-metal hydride (NiMH), or nickel-cadmium (NiCd) battery cells. In one example, removable battery 24 includes rechargeable lithium-ion (Li-ion), nickel-metal hydride (NiMH), or nickel-cadmium (NiCd) battery cells, while internal battery 80 includes lithium polymer (Lipoly) battery cells.

Control and power source module 12 employs two power sources for redundancy and continuous operation. The primary power source is removable battery 24, which may be removed to recharge the battery, e.g. using a separate charging station. Internal battery 80 is generally non-removable and, in some examples, may be charged by either removable battery 24 or an external power source. Although control and power source module 12 is described as including removable battery 24 as the primary power source, the module also includes an adapter, external power source port 62 for a DC or AC source. An external power source connected to control and power source module 12 via port 62 may function not only to charge removable battery 24 and internal battery 80, but also as a third source of power for the device. In one example, such an external power source may be employed by control and power source module 12 over both removable battery 24 and internal battery 80 to power components of the device, as well as, e.g., implanted pump 14.

Control and power source module 12 may contain only the primary power source, removable battery 24, which may be removed to recharge the battery, e.g. using a separate charging station. An implant battery in implant controller 21 may be employed for redundancy and continuous operation. In some examples, the implant battery, may be charged by either removable battery 24 or an external power source through the power transfer to the battery charger in the implantable controller. Although control and power source module 12 is described as including removable battery 24 as the primary power source, the module also includes an adapter, external power source port 62 for a DC or AC source. An external power source connected to control and power source module 12 via port 62 may function not only to charge removable battery 24 and the implant battery, but also as a third source of power for the device. In one example, such an external power source may be employed by control and power source module 12 over both removable battery 24 and the implant battery to power components of the device, the implant controller 21, as well as, e.g., implanted pump 14.

In examples according to this disclosure, in addition to connecting an external power source to control and power source module 12 as a third power source, removable battery 24 may be replaced by an external power source, including, e.g., an alternating or direct current (AC or DC respectively) power supply. In one such example, removable battery 24 may include an adapter to which the external power source may connect. As another alternative to the configuration illustrated in the example of FIG. 5, in the event that patient 20 desires a longer runtime between charges than removable battery 24 provides, control and power source 12 may be configured to have an enlarged removable battery connected to the device. In one example the enlarged removable battery may include twice the capacity of removable battery 24, but may also be significantly larger than battery 24. In any event, such an enlarged removable battery may be connected to control and power source module 12, e.g., via port 62 or through a port on removable battery 24.

Referring again to the example of FIG. 5, removable battery 24 and back-up internal battery 80 may be configured to have the same or different operational life times between successive charges. Additionally, removable battery 24 and back-up internal battery 80 may be rated for the same or different number of charge cycles before requiring replacement. In one example, removable battery 24 is configured to operate without recharge for a period of time in a range from approximately 4 hours to approximately 8 hours. In another example, removable battery 24 is configured to operate without recharge for a period of time approximately equal to 6 hours. In one example, internal battery 80 is configured to operate without recharge for a period of time in a range from approximately 30 minutes to approximately 2 hours. In one example, internal battery 80 is configured to operate without recharge for a period of time approximately equal to 1 hour. Employing a smaller internal battery 80 in control and power source module 12 may act to reduce the size, complexity, and cost of the device by removing the necessity for two full-size external batteries and a mechanical battery locking mechanism.

In one example, removable battery 24 is a 4S2P battery with four battery cells in series and two in parallel. Removable battery 24 may include a 3 amp-hour (Ah), 14.4 volt battery that is configured to operate in a range from approximately 500 to approximately 1000 recharging cycles before necessitating replacement. The operating lifetime of removable battery 24 over the approximately 500 to approximately 1000 recharging cycles may, in one example, equate to approximately one year. In one example, internal battery 80 is a 4S1P battery with four battery cells in series and one in parallel. Internal battery 80 may include a 100 milliamp-hour (mAh), 14.4 volt battery that is configured to operate for approximately 500 recharge cycles before necessitating replacement. As noted above, in examples according to this disclosure, internal battery 80 may be non-removably connected to control and power source module 12 in the sense that it is not configured to be removed and replaced by users during normal operation of the device. However, internal battery 80 may be removed from control and power source module 12, e.g. by disassembling the device and disconnecting the internal battery from the internal circuitry of the device in order to, e.g. replace the battery after it is no longer capable of holding a charge.

Control and power source module 12 includes power management module 140, which may be embodied as a variety of hardware and/or software components. In one example, power management module 140 may be one or more algorithms stored on memory 134 and executed by one or both of first processor 130 and second processor 132 of control and power source module 12. In any event, power management module 140 may be configured to manage the charging of the power sources of control and power source module 12, which of the power sources delivers powers to which components under different operational modes of the device, and communicate the status of the power sources to users, e.g. via one or more elements of user interface 50.

In one example of control and power source module 12 of FIG. 5, power management module 140 manages the charging of removable battery 24 and internal battery 80. For example, power management module 140 may control the operation of charger 142 and charger switch 144 to selectively charge one or both of removable battery 24 and internal battery 80. As noted above, control and power source module 12 includes external power source port 62 for connecting a third external power source to the device. In examples in which a third source is employed to power some or all of the components of control and power source module 12, the device may also employ flexible on-board charging techniques to provide users the ability to charge removable battery 24 and/or internal battery 80 while connected to the device. The third power source may be either an additional external battery or another external power source, e.g. a DC or AC external power source.

In one example, charger switch 144 may include a series of field-effect transistors (FETs) or other switches may allow one or more algorithms, e.g. stored on memory 134 and executed by power management module 140 of control and power source module 12 to control which of removable battery 24 or internal battery 80 is being charged at a given time and operational state of module 12. Additionally, in one example, power management module 140 may control charger 142 and/or charger switch 144 of control and power source module 12 to select either removable battery 24 or preferably the third external power source connected via port 62 to be employed for charging the other power sources of the device. The components associated with charger 142 and charger switch 144 of control and power source management module 12 are described in detail below with reference to the example circuits of FIG. 12. In one example, the same or different algorithms executed by power management module 140 to control which power source of control and power source module 12 is charged may also control the battery charge profile based on the state of removable battery 24 and internal battery 80 and, if connected via port 62, the third external power source.

When employed for use with a VAD or other MCS, power will be delivered by control and power source module 12 to implanted pump controller 21 primarily from removable battery 24. If battery 24 becomes depleted and requires removal and recharging, or, if the removable battery fails, power management module 140 of control and power source module 12 may automatically toggle to internal battery 80 or to an external power source connected to the device via port 62. Power management module 140 accomplishes this multiplexing of power sources associated with control and power source module 12 via power junction 146 in the example of FIG. 5.

In one example, power junction 146 may include a number of ideal diodes connected to removable battery 24, internal battery 80, and, if connected to control and power source module 12 via port 62, a third external power source. The ideal diodes of such an example of power junction 146 may be configured to automatically select the power source connected to control and power source module 12 with the highest voltage. In some examples of control and power source module 12, however, removable battery 24 and internal battery 80 may be configured to operate at approximately the same voltage. In such an example, a small amount of discharge of removable battery 24 may cause the operating voltage of the removable battery to fall below internal battery 80, which, without intervention would cause the ideal diodes of power junction 146 to select the internal battery after only a small amount of use of the removable battery. As such, in one example, in addition to the ideal diodes, power junction 146 may include a switch controlled by power management module 140 that may function to override the diodes, under some conditions, to select removable battery 24 to power components of control and power source module 12 and implanted pump 14 over internal battery 80.

Power management module 140 may control the switch of power junction 146 to select removable battery 24 to deliver power until the removable battery has been deleted to a threshold charge level, at which point, the power management module 140 may, e.g., deactivate the switch to allow the ideal diodes of power junction 146 to select internal battery 80. In one example, power management module 140 in conjunction with power junction 146 may be configured to select an external power source to power components of control and power source module 12 and implanted pump 14 over removable battery 24 and internal battery 80 whenever such a source is connected the device via port 62. In one example, power management module 140 in conjunction with power junction 146 may be configured to select the external power source regardless of the level of charge on removable battery 24 of internal battery 80. Additional details of power junction 146 are described in detail below with reference to the example circuits of FIG. 11.

Regardless of the particular configuration of power junction 146, power management module 140 may monitor the power sources connected to control and power source module 12 and selectively activate one of the power sources depending on the operating conditions of the device. For example, power management module 140 may monitor which of removable battery 24, internal battery 80, and an external power source are connected to control and power source module 12 to determine which of the connected sources should be used to power components of module 12, as well as implanted pump 14. Additionally, power management module 140 may monitor removable battery 24 and internal battery 80 to selectively activate one of the batteries based on the level of charge remaining on the batteries. For example, while removable battery 24 is being used, back-up internal battery 80 may be periodically tested by power management module 140 to determine a level of charge left in the internal battery. In the event removable battery 24 drops below a threshold charge level, power management module 140 may activate internal battery 80, provided, in some examples, the internal battery has at least a threshold amount of charge left.

Power management module 140, alone or in conjunction with power junction 146 may be configured to selectively activate one of the power sources of module 12 based on reasons other than the voltage delivered by the power source and the charge level remaining on the power source. For example, power management module 140 may be configured to selectively activate one of removable battery 24 or internal battery 80 based on the source and amplitude of a particular power requirement. As noted above, removable battery 24 and internal battery 80 may include rechargeable batteries with a variety of chemistries, including, e.g., lithium-ion (Li-ion), lithium polymer (Lipoly), nickel-metal hydride (NiMH), or nickel-cadmium (NiCd). In addition to removable battery 24 and internal battery 80 including particular chemistries, each of the batteries of control and power source module 12 may be configured with particular performance characteristics, based upon which, in some examples, power management module 140 may selectively activate one of the batteries.

In one example according to this disclosure, control and power source module 12, or another such device according to this disclosure, includes one energy dense power source and one power dense power source. For example, removable battery 24 of control and power source module 12 may be an energy dense power source and internal battery 80 may be a power dense power source. In another example, removable battery 24 of control and power source module 12 may be a power dense power source and internal battery 80 may be an energy dense power source. An energy dense power source may be a power source that is designed to maximize the total amount of energy per unit volume that the source can deliver. In the case of a rechargeable battery, an energy dense power source may be a battery that is designed to maximize the total amount of energy per unit volume that the source can deliver between successive charges. A power dense power source, on the other hand, may be a power source that is designed to maximize the power per unit volume that the source can deliver at any given time, e.g. to accommodate large power loads.

In one example, removable battery 24 of control and power source module 12 may be an energy dense power source including an energy density in a range from approximately 455 to approximately 600 watt-hours per liter (W-hr/L). In one example, internal battery 80 may be a power dense power source including a power density in a range from approximately 700 watts per liter (W/L) to approximately 6 kilowatts per liter (kW/L). In one example in which removable battery 24 of control and power source module 12 is an energy dense power source and internal battery 80 is a power dense power source, power management module 140 may be configured to selectively activate one of removable battery 24 or internal battery 80 based on the amplitude of a particular power requirement. For example, implanted pump 14 may have transient operating conditions which temporarily cause large spikes in the power drawn by the pump. In one example, starting implanted pump 14 may draw a significantly larger amount of power than running the pump at steady state, e.g. start-up may draw approximately 50 watts while steady state draws approximately 5 watts. In another example, transient physiological conditions of patient 20 may cause large power draws from pump 14. In examples including large power spikes in the power requirements of, e.g. implanted pump 14, power management module 140 may selectively activate internal battery 80, e.g. by controlling power junction 146, regardless of the charge level of removable batter 24, because the power dense internal battery may be better adapted for handling the power spike than the energy dense removable battery.

In addition to managing power source charging and selectively activating power sources for power delivery, as described in the foregoing examples, power management module 140 may also be configured to manage communicating the status of the power sources to users, e.g. via one or more elements of user interface 50. An example process by which power management module 140 of control and power source 12 may manage communicating the status of the power sources of the device to users is illustrated in the state diagram of FIG. 6. Functions and appearances of an example configuration of the elements of user interface 50 of control and power source module 12 are illustrated in FIGS. 7A-9C, some of which are described with reference to the state diagram of FIG. 6 by which power management module 140 of control and power source 12 manages communicating the status of the power sources of the device to users in one example according to this disclosure.

Figure 6:
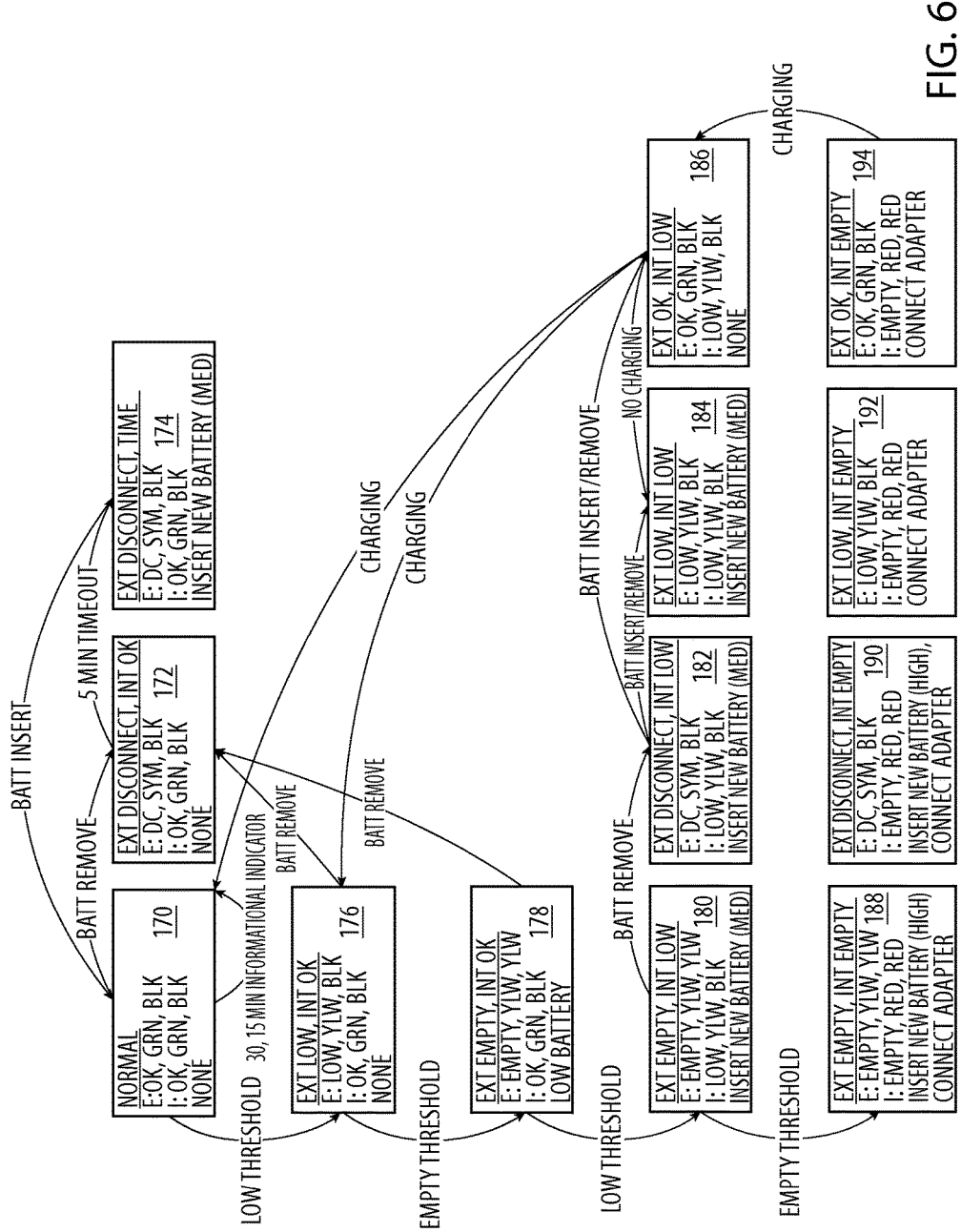
FIG. 6 is a state diagram representing a process by which the status of power sources of the control and power source module of FIG. 5 may be communicated to a user.

FIG. 6 illustrates states 170-194 of the power sources connected to control and power source module 12, e.g. removable battery 24, internal battery 80, and, in some examples, an external power source connected via port 62. The state diagram of FIG. 6 is organized such that movement between states from the left side to the right of the diagram indicates states in which removable battery 24 is disconnected from and reconnected to control and power source module 12. Additionally, the state diagram of FIG. 6 is organized such that movement between states from the top to the bottom of the diagram indicates states in which one or both of one or both of removable battery 24 and internal battery 80 are progressively depleted to different threshold charge levels.

The state diagram of FIG. 6 uses a number of abbreviations. In FIG. 6, "batt" generally refers to battery. Each of states 170-194 include a state description, e.g. "Normal" for state 170, status and user interface indications related to each of removable battery 24 and internal battery 80, e.g. "E: OK, GRN, BLK" for removable battery 24 and "I: OK, GRN, BLK" for internal battery 80, and alarms communicated to users via user interface 50. With reference to the status and user interface indications related to each of removable battery 24 and internal battery 80, the abbreviations used in FIG. 6 have the following meanings The first letter, e.g. E or I, refers to which of removable battery 24 or internal battery 80, respectively, the status and user interface indications relates. The first letter E, as well as the abbreviation Ext in the state description refers to an external battery, which in the example of FIG. 6 is equivalent to a removable battery, such as removable battery 24 of control and power source module 12. For both the removable battery 24 and internal battery 80, the status and user interface indications are the charge and operational state of the battery, the color of the alarm indication on user interface 50, and the color of the graphical representation of the battery on user interface 50. For example, in state 170, "E: OK, GRN, BLK" means that removable battery 24 is above a low charge level threshold and is operating properly (OK), the color of the alarm indication on user interface 50 is green (GRN), and the color of the graphical representation of the battery on user interface 50 is black (BLK).

In the state diagram of FIG. 6, alarm and battery representation color "YLW" stands for yellow and "RED" indicates the color red. In the event removable battery 24 is disconnected from control and power source module 12, the state of the battery is indicated in FIG. 6 as "DC," which stands for disconnected. Additionally, both removable battery 24 and internal battery 80 include three threshold charge levels, indicated by "OK, LOW, and EMPTY." The battery condition OK, as far as charge level is concerned, indicates that the battery to which the condition refers is above a threshold low charge level, while LOW indicates the battery is at a threshold low charge level, which may be a range of charge levels, and EMPTY indicates the battery is at a threshold empty charge level, which may also be a range of charge levels and which may be greater than zero charge. The threshold charge levels for removable battery 24 and internal battery 80 employed in examples according to this disclosure may be the same or different, in number as well as magnitude.

Starting in the upper right hand corner of the state diagram of FIG. 6, state 170 indicates a normal operational state for control and power source module 12. In state 170, removable battery 24 and internal battery 80 are both above a threshold low charge level, and there state is thus indicated in state 170 as OK. The indication in state 170 that removable battery 24 and internal battery 80 are both OK because the batteries are above a threshold low charge level does not necessarily mean that the batteries are fully charged and may occur regardless of whether control and power source module 12 is connected to an external power source to charge one or both of the batteries. For example, state 170 may occur when removable battery 24 is partially discharged, but the charge level of the battery is still above a low threshold level that may necessitate alerting the user and recharging. Similarly, state 170 may occur when internal battery 80 is partially discharged, but the charge level of the battery is still above a low threshold level that may necessitate alerting the user and recharging. State 170 may also occur when both removable battery 24 and internal battery 80 are partially discharged, but the charge levels of both the batteries are still above a low threshold level that may necessitate alerting the user and recharging. In another example, state 170 may occur when both removable battery 24 and internal battery 80 are fully charged and when an external power source is connected to control and power source module 12, as long as both batteries are also above a threshold low charge level.

Figure 7A:
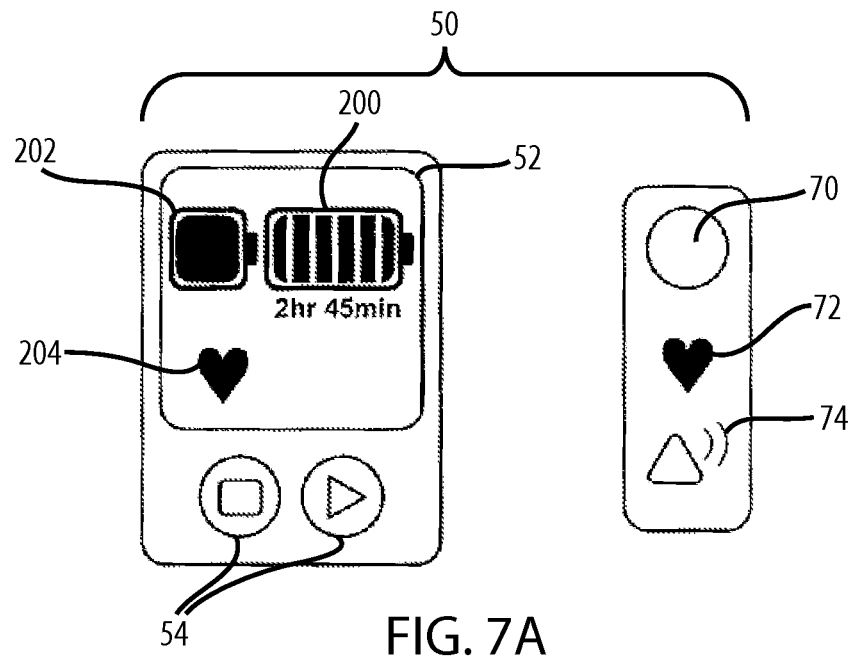
FIGS. 7A-10B illustrate a number of functions associated with elements of an example user interface of the control and power source module of FIG. 5.
Figure 7B:
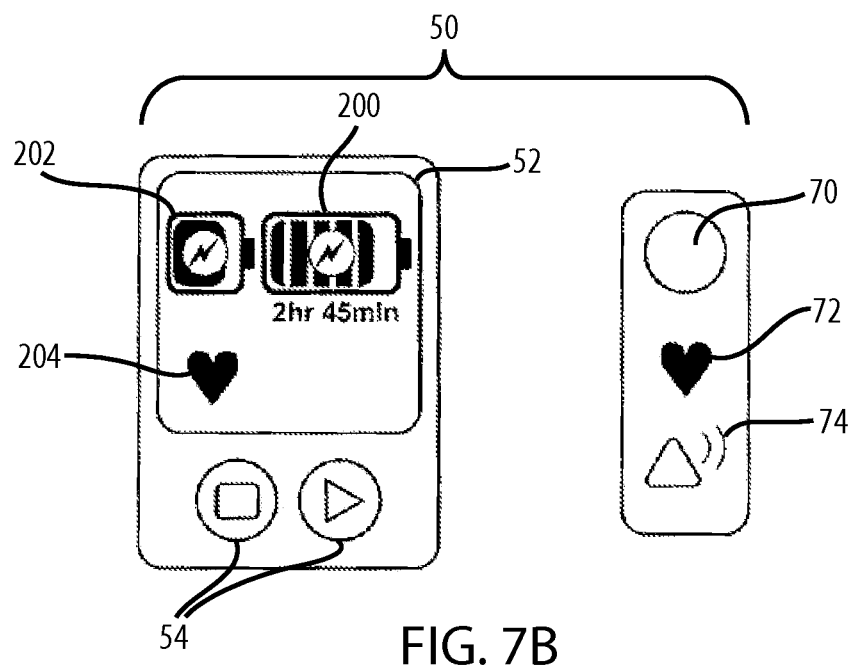

FIGS. 7A and 7B illustrate examples of the manner in which power management module 140 may control user interface 50 when control and power source module 12 is in the normal operational state indicated by state 170 in FIG. 6. As described above, user interface 50 of control and power source module 12 includes display 52, input buttons 54, as well as mute button 70 and status indicators 72 and 74. In the examples of FIGS. 7A and 7B, display 52 includes removable battery icon 200, internal battery icon 202, and status indicator 204. Also in the examples of FIGS. 7A and 7B, as well as FIGS. 8-10B, input buttons 54 are encoded with two different icons, one a rectangular icon and the other a triangular icon. In these examples of user interface 50, input buttons 54 correspond to two main functions for interacting with control and power source module 12. Input button 54 encoded with the rectangular icon may function as a "home" button that, when activated by a user, navigates to a default screen presented on display 52 of user interface 50. Input button 54 encoded with the triangular icon may function as a "next" button that, when activated by a user, toggles to the next screen in a series of possible screens that may be presented on display 52 of user interface 50.

FIG. 7A illustrates an example in which removable battery 24 and internal battery 80 of control and power source module 12 are fully charged, as indicated by the amount of fill in removable battery icon 200 and internal battery icon 202 associated with removable and internal batteries 24 and 80, respectively. In FIG. 7A, neither removable battery 24 or internal battery 80 are currently being charged, e.g. either by an external power source connected to control and power source module 12 via port 62 or, in the case of internal battery 80 by removable battery 24.

As the conditions of removable battery 24 and internal battery 80, as well as various other components of control and power source module 12, in FIG. 7A indicate a normal operating state corresponding to state 170 from FIG. 6, status indicator 204 on display 52 presents a heart icon. Additionally, status indicator 72 is activated by control and power source module 12 to illuminate the heart shaped indicator. Finally, because the conditions of removable battery 24 and internal battery 80, as well as various other components of control and power source module 12, indicate a normal operating state that does not necessitate any alarms, display 52 does not present any alarm icons and status indicator 74 associated with alarm conditions is not illuminated.

FIG. 7B illustrates an example in which removable battery 24 and internal battery 80 of control and power source module 12 are less than fully charged, but are above a threshold low charge level, as indicated by the amount of fill in graphics 200 and 202 associated with removable and internal batteries, respectively. Additionally, in FIG. 7B, both removable battery 24 and internal battery 80 are currently being charged, as indicated by charging icon 206 overlaid on removable battery icon 200 and internal battery icon 202. As described above, removable battery 24 may be charged while connected to control and power source module 12 by an external power source connected to module 12 via port 62. Additionally, internal battery 80 may be charged by the external power source or removable battery 24. As the conditions of removable battery 24 and internal battery 80, as well as various other components of control and power source module 12, in FIG. 7B indicate a normal operating state corresponding to state 170 from FIG. 6, as with the state of the device illustrated in FIG. 7A, status indicator 204 on display 52 presents a heart icon, status indicator 72 is illuminated, and status indicator 74 associated is not illuminated.

In both FIGS. 7A and 7B, power management module 140 may present control battery icon 200 and internal battery icon 202 in black, while the charge level of removable battery 24 and internal battery 80 indicated by the fill in battery icon 200 and internal battery icon 202, as well as status indicator 204 on display 52 and status indicator 72 may be presented in green, as indicated by state 170 in FIG. 6.

Referring again to FIG. 6, moving from state 170 to the right, state 172 indicates that removable battery 24 is disconnected from control and power source module 12, while internal battery 80 is above a threshold low charge level. State 172 indicates the disconnection of removable battery 24 as DC. In the example state diagram of FIG. 6, whenever removable battery 24 is disconnected from control and power source module 12, the alarm color is indicated not by a color but by a symbol, which is abbreviated in the states of FIG. 6 as "SYM." An example of this disconnection symbol is illustrated in the example of user interface 50 in FIG. 8. Removable battery 24 may disconnect from control and power source module 12 for a variety of reasons. In one example, a user, e.g. patient 20 may have more than one removable battery that may be connected to control and power source module 12 such that it is possible to always or nearly always have a fully charged removable battery that can be swapped for a discharged battery. In another example, removable battery 24 may malfunction and necessitate complete replacement. In another example, removable battery 24 may reach its maximum number of charge cycles such that it is no longer able to hold a charge and thus necessitates complete replacement.

Figure 8:
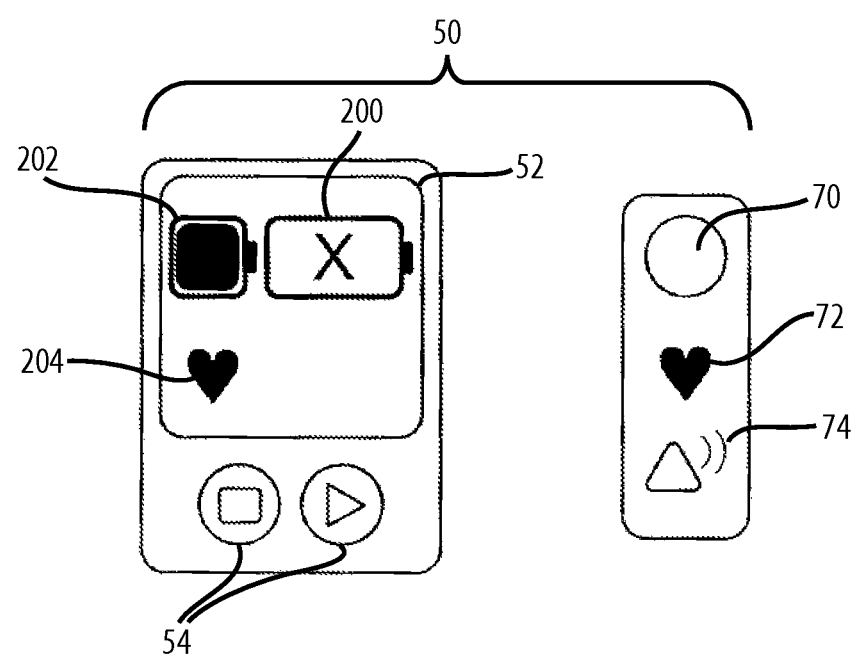

FIG. 8 illustrates an example of the manner in which power management module 140 may control user interface 50 when control and power source module 12 is in the disconnected removable battery state indicated by state 172 in FIG. 6. In the example of FIG. 8, display 52 includes removable battery icon 200, internal battery icon 202, status indicator 204, and disconnect symbol 206. FIG. 8 illustrates an example in which removable battery 24 is disconnected from control and power source module, as indicated by disconnect symbol 206 overlaid on removable battery icon 200. Internal battery 80 of control and power source module 12, as indicated in state 172 in FIG. 6, is above a threshold low charge level, and, in particular in FIG. 8 is fully charged, as indicated by the amount of fill in internal battery icon 202.

In FIG. 8, neither removable battery 24 or internal battery 80 are currently being charged, e.g. either by an external power source connected to control and power source module 12 via port 62 or, in the case of internal battery 80 by removable battery 24.

As the conditions of internal battery 80, as well as various other components of control and power source module 12, in FIG. 8 do not indicate any alarm conditions, power management module 140 may present status indicator 204 on display 52 as a heart icon. Additionally, status indicator 72 is activated by power management module 140 to illuminate the heart shaped indicator. Finally, because the condition of control and power source module 12 does not the necessity for any alarms, display 52 does not present any alarm icons and status indicator 74 associated with alarm conditions is not illuminated.

In FIG. 8, power management module 140 may present battery icon 200, internal battery icon 202, and disconnect symbol 206 in black, while the charge level of internal battery 80 indicated by the fill in internal battery icon 202, as well as status indicator 204 on display 52 and status indicator 72 may be presented in green, as indicated by state 172 in FIG. 6.

Referring again to FIG. 6, moving from state 172 to the right, state 174 indicates that disconnection timeout has been reached, which causes power control module 140 to trigger an alarm instructing a user of control and power source module 12 to reconnect removable battery 24 or another such power source to the device. The disconnection timeout in the example of FIG. 6 is indicated as five minutes such that leaving removable battery 24 disconnected from control and power source module 12 for more than five minutes will trigger a battery reconnection alarm. However, in other examples according to this disclosure, the disconnection timeout may be more or less time than in the example of FIG. 6. For example, the disconnection timeout may be equal to ten minutes such that power management module 140 will trigger a battery reconnection alarm after leaving removable battery 24 disconnected from control and power source module 12 for more than ten minutes. In one example of state 174, power management module 140 may control user interface 50 to present instructions to a user of control and power source module 12 on display 52 to insert a new or recharged removable battery after the disconnection timeout has been reached. In another example, power management module 140 may also control speaker driver 150 and speakers 90 to cause the speakers to issue and audible sound.

In the example of FIG. 6, moving down from normal state 170 to state 188 the charge levels of removable battery 24 and internal battery 80 get progressively lower. Additionally, moving down from normal state 170 to state 188 the alarms issued by power management module 140 and the instructions associated with such alarms increase in severity, e.g. by changing graphical symbols, color, and/or the amplitude of audible sounds issued by speakers 90 of control and power source module 12. In state 176, removable battery 24 has reached a threshold low charge level, while internal battery 80 remains above a threshold low charge level. In state 178, removable battery 24 has reached a threshold empty charge level, while internal battery 80 remains above a threshold low charge level. In state 178, because removable battery 24 has reached a threshold empty charge level, power management module 140 of control and power source module 12 triggers a low battery alarm. In one example of state 18, user interface 50 may illuminate status indicator 74 and present status indicator 204 on display 52 as an alarm icon. Additionally, user interface 50 may present a user of control and power source module 12 an indication on display 52 of the low battery charge level, e.g. by coloring part or all of a removable battery icon on display 52 yellow. In state 180, removable battery 24 has reached a threshold empty charge level and internal battery 80 has reached a threshold low charge level. Finally, in state 188, removable battery 24 and internal battery 80 have both reached a threshold empty charge level.

In addition to the charge levels of removable battery 24 and internal battery 80 progressively lowering moving down from state 170 to state 188 in the example of FIG. 6, the alarms issued by power management module 140 and the instructions associated with such alarms increase in severity, e.g. by changing graphical symbols and colors associated with elements of user interface 50 and/or changing the amplitude of audible sounds issued by speakers 90 of control and power source module 12. For example, while the alarm associated with the empty removable battery and ok internal battery state 178 may include user interface 50 presenting a user of control and power source module 12 an indication on display 52 of the low battery charge level, e.g. by coloring part or all of a removable battery icon on display 52 yellow, the alarm associated with the empty removable battery and low internal battery state 180 may include presenting the user instructions on display 52 to insert a new battery. In one such example, the priority of the alarm instructing the user to insert a new battery, as indicated, e.g., by the amplitude of a sound issued by speakers 90, may be medium.

In the empty removable battery and empty internal battery state 188, in contrast to both states 178 and 180, power management module 140 may further increase the severity of the alarms presented to the user of control and power source module. As indicated in FIG. 6, for example, power management module 140 may color alarms and battery icons presented by user interface 50 on display 52 red and may also issue instructions to the user to insert a new battery and/or connect control and power source module 12 to an external power source, e.g. via port 62. In one such example, the priority of the alarm instructing the user to insert a new battery and/or connect control and power source module 12 to an external power source, as indicated, e.g., by the amplitude of a sound issued by speakers 90, may be high.

Referring again to state 180 in the example of FIG. 6, moving to the right from state 180 indicates situations in which internal battery 80 maintains a charge at a threshold low charge level, but the state of removable battery 24 changes, including disconnecting and reconnecting or replacing the removable battery. In state 182, removable battery 24 is disconnected from control and power source module 12 and internal battery 80 is at a threshold low charge level. In state 182, power management module 140 may issue an alarm to a user of control and power source module 12, including, e.g., controlling user interface 50 to present a symbol associated with a removable battery icon indicating that battery 24 has been disconnected and to color part or all of an internal battery icon on display 52 yellow. Power management module 140 may also present instructions on display 52 to insert a new battery, as well as indicating the priority of the alarm instructing the user to insert a new battery as medium by, e.g., controlling speakers 90 to issue an audible sound at a particular amplitude.

In state 184, a removable battery at a threshold low charge level is connected to control and power source module 12 and internal battery 80 is at a threshold low charge level. In one example of state 184, removable battery 24 has been recharged to the threshold low charge level and reconnected to control and power source module 12. In another example, however, removable battery 24 has been replaced by another removable battery, which is at the threshold low charge level and which is connected to control and power source module 12. In state 184, power management module 140 may issue an alarm to a user of control and power source module 12, including, e.g., controlling user interface 50 to color part or all of a removable battery icon and an internal battery icon on display 52 yellow, present instructions on display 52 to insert a new battery, as well as indicating the priority of the alarm instructing the user to insert a new battery as medium by, e.g., controlling speakers 90 to issue an audible sound at a particular amplitude.

In state 186, a removable battery above a threshold low charge level is connected to control and power source module 12 and internal battery 80 is at a threshold low charge level. In one example of state 186, removable battery 24 has been recharged to above the threshold low charge level and reconnected to control and power source module 12. In another example, however, removable battery 24 has been replaced by another removable battery, which is charged above the threshold low charge level and which is connected to control and power source module 12. In state 186, power management module 140 may issue an alarm to a user of control and power source module 12, including, e.g., controlling user interface 50 to color part or all of a removable battery icon green to indicate that the removable battery is above the threshold low charge level and controlling user interface 50 to color part or all of an internal battery icon on display 52 yellow to indicate that internal battery 80 is still at the threshold low charge level.

Referring again to state 188 in the example of FIG. 6, moving to the right from state 188 indicates situations in which internal battery 80 maintains a charge at a threshold empty charge level, but the state of removable battery 24 changes, including disconnecting and reconnecting or replacing the removable battery. In state 190, removable battery 24 is disconnected from control and power source module 12 and internal battery 80 is at a threshold empty charge level. In state 190, power management module 140 may issue an alarm to a user of control and power source module 12, including, e.g., controlling user interface 50 to present a symbol associated with a removable battery icon indicating that battery 24 has been disconnected and to color part or all of an internal battery icon on display 52 red. Power management module 140 may also present instructions on display 52 to insert a new battery and/or connect control and power source module 12 to an external power source, as well as indicating the priority of the alarm instructing the user to insert a new battery as high by, e.g., controlling speakers 90 to issue an audible sound at a particular amplitude, e.g. a higher amplitude than a sound issued for a medium priority alarm.

In state 192, a removable battery at a threshold low charge level is connected to control and power source module 12 and internal battery 80 is at a threshold empty charge level. In one example of state 192, removable battery 24 has been recharged to the threshold low charge level and reconnected to control and power source module 12. In another example, however, removable battery 24 has been replaced by another removable battery, which is at the threshold low charge level and which is connected to control and power source module 12. In state 192, power management module 140 may issue an alarm to a user of control and power source module 12, including, e.g., controlling user interface 50 to color part or all of a removable battery icon yellow and an internal battery icon on display 52 red, as well as present instructions on display 52 to connect control and power source module 12 to an external power source.

In state 194, a removable battery above a threshold low charge level is connected to control and power source module 12 and internal battery 80 is at a threshold empty charge level. In one example of state 194, removable battery 24 has been recharged to above the threshold low charge level and reconnected to control and power source module 12. In another example, however, removable battery 24 has been replaced by another removable battery, which is charged above the threshold low charge level and which is connected to control and power source module 12. In state 194, power management module 140 may issue an alarm to a user of control and power source module 12, including, e.g., controlling user interface 50 to color part or all of an internal battery icon on display 52 red to indicate that internal battery 80 is still at the threshold empty charge level. As internal battery 80 is still at the threshold empty charge level, power management module 140 may also present instructions on display 52 to connect control and power source module 12 to an external power source to charge the internal battery above the empty threshold without depleting the removable battery.

The foregoing example of the state diagram of FIG. 6 is described by beginning with state 170 in the upper right hand corner of the diagram and moving in a number of directions from that state. However, the selection of state 170 as a starting point as well as the movements from there to other states described below is arbitrary and does not indicate any required order for the states of control and power source module 12. The arrows in the state diagram of FIG. 6 illustrate that movement between the various states of control and power source module 12 may occur as a result of a number of different factors, including, e.g. removing or inserting a removable battery, depleting or increasing the charge level of one or both of removable battery 24 and internal battery 80 to a number of different thresholds, and charging one or both of removable battery 24 and internal battery 80.

Figure 9A:
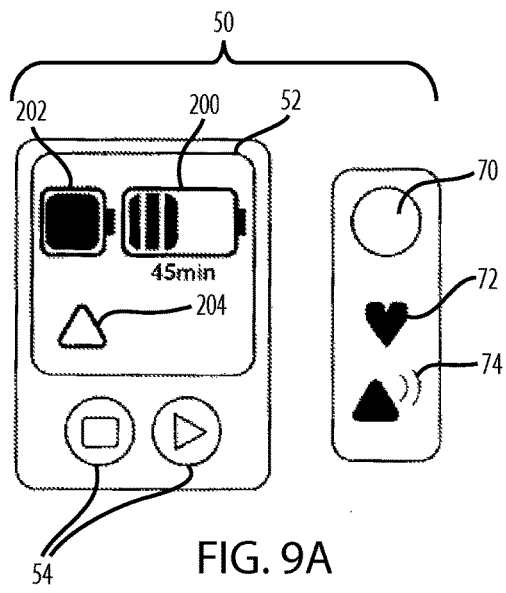

FIGS. 9A-10B illustrate a number of additional example functions and appearances of an example configuration of the elements of user interface 50 of control and power source module 12. FIGS. 9A-C illustrate a number of examples of user interface 50 by which power management module 140 indicates three states of control and power source module 12 with removable battery 24 and internal battery 80 at varying charge levels. In the examples of FIGS. 9A-C, neither removable battery 24 or internal battery 80 are currently being charged, e.g. either by an external power source connected to control and power source module 12 via port 62 or, in the case of internal battery 80 by removable battery 24.

FIG. 9A illustrates examples of the manner in which power management module 140 may control user interface 50 when removable battery 24 is at a threshold low charge level and internal battery 80 is above a threshold charge level. In one example of the state represented by user interface 50 in FIG. 9A, power management module 140 may present status indicator 204 on display 52 as an alarm icon. In the example of FIG. 9A, status indicator 204 indicates the lowest level alarm condition by outlining the alarm icon and presenting no emphasis symbols. Status indicator 72 is also deactivated by power management module 140 such that the heart shaped indicator is not illuminated and status indicator 74 is illuminated to indicate the alarm condition. In the example of FIG. 9A, status indicator 204 indicates the lowest level alarm condition by illuminating the triangle portion of the indicator without illuminating the emphasis symbols indicated as two curved lines in FIG. 9A. In one example, power management module 140 may present removable battery icon 200 and internal battery icon 202 in black, while the charge level of removable battery 24 indicated by the fill in battery icon 200, as well as status indicator 204 on display 52 and status indicator 74 may be presented in yellow. Power management module may present the charge level of internal battery 80 indicated by the fill in battery icon 202 as green to indicate, in contrast to removable battery 24, the internal battery is above a threshold low charge level.

Figure 9B:
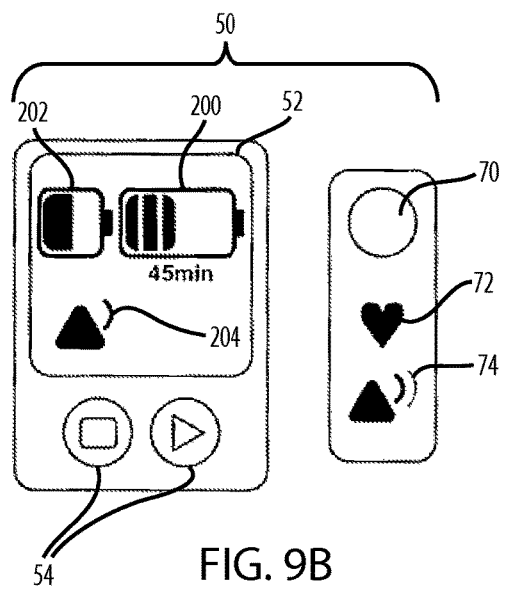

FIG. 9B illustrates examples of the manner in which power management module 140 may control user interface 50 when both removable battery 24 and internal battery 80 are at a threshold low charge level. In one example of the state represented by user interface 50 in FIG. 9B, power management module 140 may present status indicator 204 on display 52 as an alarm icon. In the example of FIG. 9B, status indicator 204 indicates a medium level alarm condition by filling the alarm icon and presenting one emphasis symbol represented by a thickened curved line. Status indicator 72 is also deactivated by power management module 140 such that the heart shaped indicator is not illuminated and status indicator 74 is illuminated to indicate the alarm condition. In the example of FIG. 9B, status indicator 204 indicates the medium level alarm condition by illuminating the triangle portion of the indicator and illuminating one of the two emphasis symbols indicated as two curved lines in FIG. 9B. In one example, power management module 140 may present removable battery icon 200 and internal battery icon 202 in black, while the charge level of removable battery 24 and internal battery 80 indicated by the fill in battery icons 200 and 202, as well as status indicator 204 on display 52 and status indicator 74 may be presented in yellow.

Figure 9C:
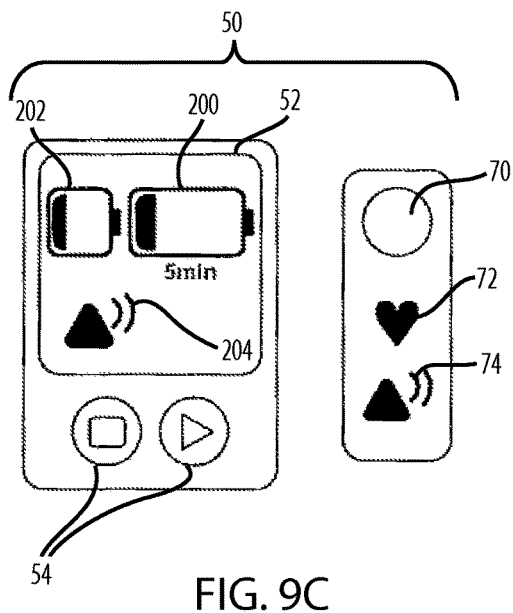

FIG. 9C illustrates examples of the manner in which power management module 140 may control user interface 50 when both removable battery 24 and internal battery 80 are at a threshold empty charge level. In one example of the state represented by user interface 50 in FIG. 9C, power management module 140 may present status indicator 204 on display 52 as an alarm icon. In the example of FIG. 9C, status indicator 204 indicates a high level alarm condition by filling the alarm icon and presenting two emphasis symbols represented by two thickened curved lines. Status indicator 72 is also deactivated by power management module 140 such that the heart shaped indicator is not illuminated and status indicator 74 is illuminated to indicate the alarm condition. In the example of FIG. 9C, status indicator 204 indicates the high level alarm condition by illuminating the triangle portion of the indicator and illuminating both emphasis symbols indicated as two curved lines in FIG. 9C. In one example, power management module 140 may present removable battery icon 200 and internal battery icon 202 in black, while the charge level of removable battery 24 and internal battery 80 indicated by the fill in battery icons 200 and 202, as well as status indicator 204 on display 52 and status indicator 74 may be presented in red.

Figure 10A:
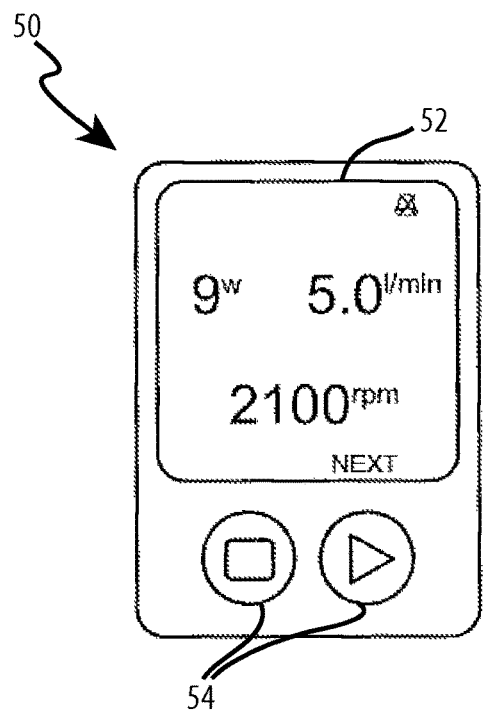
Figure 10B:
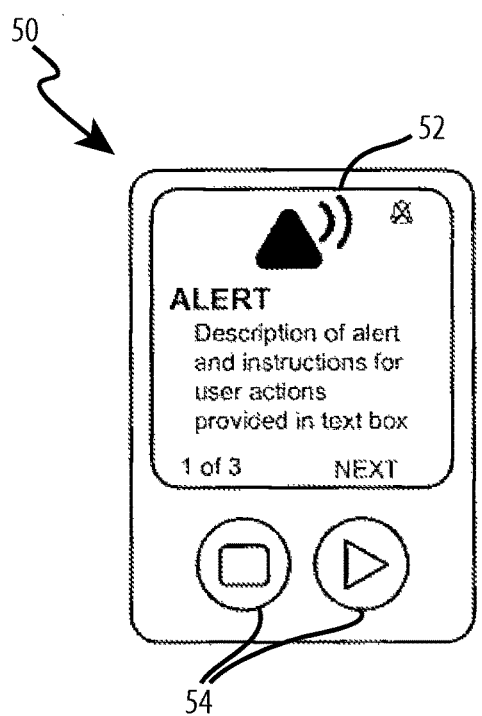

FIGS. 10A and 10B illustrate screens that may be presented by display 52 of user interface 50 in addition to the screens indicating battery charge state and alarm conditions. FIG. 10A illustrates an example in which power management module 140 presents various parameters related to the implanted pump 14. As described below, power management module 140, in conjunction with power bridge 148 illustrated in FIG. 5, may be configured to detect the operational parameters of the motor driving implanted pump 14. In FIG. 10A, power management module 140 presents the current power drawn by the motor driving pump 14 in watts (w), the current throughput of the pump in liters per minute (l/min), and the current angular velocity of the pump motor in revolutions per minute (rpm). FIG. 10B illustrates an example in which power management module 140 presents a description of an alarm the module issues to a user of control and power source module 12, as well as instructions for remedial actions that may be performed by the user to take the control and power source module out of the alarm state.

Referring to FIGS. 7A, 7B, and 9A-10B, power management module 140 not only presents users of control and power source module 12 with estimations of the amount of charge remaining in removable battery 24 and internal battery 80, but also provides an estimate of the amount of time the batteries will continue to operate before requiring replacement or recharging. For example, in FIGS. 7A and 7B, power management module 140 calculates the time remaining on the battery charges as two hours and forty five minutes, which is presented by user interface 50 on display 52 just below removable battery icon 200. In FIGS. 9A and 9B, power management module 140 calculates the time remaining on the battery charges as forty five minutes, which is presented by user interface 50 on display 52 just below removable battery icon 200. In one example, power management module 140 may calculate and user interface 50 may present the time remaining on the charge of removable battery 24. In another example, power management module 140 may calculate and user interface 50 may present the time remaining on the charge of internal battery 80. In another example, power management module 140 may calculate and user interface 50 may present the total time remaining on the charges of both removable battery 24 and internal battery 80. In another example, power management module 140 may calculate the time remaining on the charges of each of removable battery 24 and internal battery 80, which user interface may present separately on display 52.

Power management module 140 may use a number of different types of estimations and/or assumptions to calculate time remaining on the battery charges for control and power source module 12. In one example, power management module 140 may assume a default nominal power draw from the components of control and power source module 12 and implanted pump 14 and calculate the time remaining on the battery charges based on the default power requirement and the amount of charge left on removable battery 24 and internal battery 80. In another example, power management module 140 may track and store the power drawn by the components of control and power source module 12 and implanted pump 14 and average the power requirements over time. Power management module 140 may then calculate the time remaining on the battery charges based on the average historical power requirement and the amount of charge left on removable battery 24 and internal battery 80.

Referring again to FIG. 5, in addition to the redundant power source architecture described above, control of control and power source module 12 also includes dual processors 130, 132 and two telemetry modules 136, 138, both which elements of the device of FIG. 5 may be configured for redundant and/or complementary operation. Control and power source module 12 may employ first and second processors 130, 132 to provide error protection and redundant operation in the event one processor malfunctions. Additionally, first and second processors 130, 132 may be configured to power different components of control and power source module 12 and to further improve power management achieved by the device. In this sense, the use of first and second processors 130, 132 may be controlled by power management module 140, which, as noted above, may, in some examples, be embodied as one or both of processors 130, 132 and memory 134.

In one example employing error protection and redundancy techniques, first and second processors 130, 132 are configured to periodically test each other to detect malfunctions and/or failures. In the event one of first and second processors 130, 132 malfunctions or fails, the other of the processors may shut down the malfunctioning processor and assume management/control of any of the components of control and power source module 12 and/or implanted pump 14 previously handled by the malfunctioning processor. Additionally, the one of first and second processors 130, 132 that is still operating properly may trigger an alarm to alert a user of control and power source module 12 to the processor error/failure. For example, the one of first and second processors 130, 132 that is still operating properly may control display 52 of user interface 50 to present a message to the user of control and power source module 12, which the processor may retrieve, e.g., from memory 134.

In addition to error protection and redundancy techniques, first and second processors 130, 132 may be configured to manage and control different components of control and power source module 12 and one of the two may be configured to manage and control implanted pump 14. In the example of FIG. 5, first processor 130 is communicatively connected to memory 134, first telemetry module 136, power management module 140, and speaker driver 150. Power management module 140, connected to and associated with first processor 130, is communicatively connected to charger 142, power junction 146, and power inverter 148. In the example of FIG. 5, therefore, first processor 130, by default, is configured to control and manage implanted pump 14 via power management module 140 and power inverter 148. Second processor 132, on the other hand, is connected to memory 134, second telemetry module 138, sensors 152, and user interface 50. Thus, the control and management of control and power source module 12 is split between first processor 130 and second processor 132. The connection lines illustrated between components of control and power source module 12 in FIG. 5 are not meant to represent the only connections in the device. For example, in the event that first processor 130 malfunctions or fails, second processor 132 may take over control and management of implanted pump 14 via power management module 140 and power bridge 148.

In order to provide redundant operation of implanted pump controller 21, both first and second processors 130, 132 are configured to control and manage the power transfer in the event the other processor malfunctions or fails. However, first and second processors 130, 132 may not be, in some examples, exactly the same. For example, one of first and second processors 130, 132 may have lower power requirements than the other processor to further decrease the power loads on removable batter 24 and internal battery 80 of control and power source module 12. In any event, splitting the control and management of control and power source module 12 between first processor 130 and second processor 132 enables some of the components of the device to be shut down when not in use, which may, in turn, significantly decrease the power requirement of the electronics of the device. Thus, although control and power source module 12 may be designed to maximize space utilization and minimize the size of the device and although two processors may take up more space and weighs more than one, employing first and second processors 130, 132 may effectively reduce the power requirements enough that the size and capacity of removable battery 24 and internal battery 80 are also reduced.

In one example, first processor 130 is configured to transfer power and communicate to pump controller 21 via power bridge 148, first telemetry module 136, power management module 140, and also to control speaker driver 150. Second processor 132 is configured to control user interface 50, second telemetry module 138, and sensors 152. However, only a limited number of these components of control and power source module 12 are required be running all or even most of the time, which are primarily those affecting or relating to operation of power transfer and communications to pump controller 21. As such, first processor 130 and second processor 132 may be configured to shut down one or more of the components they control in the event they are not in use. For example, second processor 132 may be configured to shut down user interface 50 and second telemetry module 138 when these components of control and power source module 12 are not in use. Additionally, in this example, second processor 132 does not control any components related to implanted pump controller 21 or any other component that must operate uninterrupted. As such, second processor 132 may be shut down. In such examples in which second processor 132 is shut down, in the event a component controlled by the processor needs to operate, e.g. a user calls on an element of user interface 50, first processor 130 may be configured to detect this activity and wake-up second processor 132. Additionally, in order to continue to provide error protection and redundancy, first processor 130 may be configured to periodically wake-up second processor 132, which, in turn, may then check the first processor for any malfunctions or failures. In another example, second processor 132 may be configured to periodically wake itself up to test first processor 130 for errors or failures.

In accordance with foregoing example split of control between first and second processors 130, 132, first processor 130 may store data on and retrieve data from memory 134 related to the operation of pump controller 21 and pump 14, as well as, e.g., speakers 90. In particular, first processor 130 may, e.g., retrieve information stored on memory 134 related to parameters for controlling pump 14 to pump blood through heart 30 of patient 20. In some examples, pump 14 may include an electric motor that drives operation of the pump to draw blood from left ventricle 36 and deliver it to aorta 38. For example, pump 14 may include any number of types of three-phase direct current (DC) or alternating current (AC) motors that are controlled by implanted pump controller 21 using parameters received from first processor 130 including, e.g., motor speed (RPM) and power range (nominal, high, max power in Watts), retrieved from memory 134.

First processor 130 may also receive feedback from pump controller 21 or other devices including, e.g., removable battery 24 and internal battery 80 and store data related to the operation of the devices on memory 134. In another example, first processor 130, e.g. as part of power management module 140 monitors the level of charge in each of removable battery 24 and internal battery 80 and controls status user interface 50 to indicate to patient 20 how much charge remains in each battery, e.g. graphically on display 52.

In another example, one or more of the foregoing functions related to the operation of implanted pump 14 may be executed by second processor 132. For example, in the event first processor 130 malfunctions or fails, second processor 132 may be configured to take over power transfer to implanted pump controller 21.

Memory 134 of control and power source module 12 is a computer-readable storage medium that may be used to store data including instructions for execution by first and second processors 130, 132 or a processor of another device, such as, but not limited to, data related to the operation of pump 14 to assist heart 30 of patient 20. In another example, memory 134 may store data related to power management functions executed by power management module 140. In another example, memory 134 may store data related to power transfer functions executed by power inverter 148. For example, memory 134 may store threshold charge level values associated with different threshold charge levels for one or both of removable battery 24 and internal battery 80. In one example, memory 134 stores the low and empty threshold charge levels employed in the power management state diagram of FIG. 6. Memory 134 may include separate memories for storing instructions, patient information, pump or pump motor parameters (e.g., motor speed and power range), patient and pump operation histories, and other categories of information such as any other data that may benefit from separate physical memory modules. In some examples, memory 134 stores data that, when executed by first or second processor 130, 132, cause control and power source module 12 and pump 14 to perform the functions attributed to them in this disclosure.

Components described as processors within control and power source module 12, e.g. first and processors 130, 132 or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination. Additionally, memory 62 and other computer readable storage media described in this disclosure may include a variety of types of volatile and non-volatile memory including, e.g., random access memory (RAM), static random access memory (SRAM), read only memory (ROM), programmable read only memory (PROM), erasable programmable read only memory (EPROM), electronically erasable programmable read only memory (EEPROM), flash memory, a hard disk, magnetic media, optical media, or other computer readable media.

In addition to first and second processors 130, 132 and memory 134, control and power source module 12 includes first and second telemetry modules 136, 138. Generally speaking, first telemetry module 136 facilitate wireless communications from and to control and power source module 12 and implanted pump controller 21. Generally speaking, second telemetry modules 138 facilitate wireless communications from and to control and power source module 12 and other devices including, e.g. a separate display device for presenting a user interface to patient 20 or another user like a clinician or an device implanted within the patient, e.g. an implanted physiological sensor. First and second telemetry modules 136, 138 in control and power source module 12, as well as telemetry modules in other devices described in this disclosure, can be configured to use a variety of wireless communication techniques, including, e.g. RF communication techniques to wirelessly send and receive information to and from other devices respectively. First and second telemetry modules 136, 138 may, e.g., employ RF communication according to one of the 802.11, a Medical Implant Communication Service (MICS), Bluetooth or Bluetooth Low Energy specification sets, infrared (IR) communication according to the IRDA specification set, or another standard or proprietary telemetry protocol. First and second telemetry modules 136, 138 may send information from and receive information to control and power source module 12 on a continuous basis, at periodic intervals, or upon request from a user, e.g. patient 20 via a user interface device. In one example, second telemetry modules 138 communicates with a separate user interface device that includes a display, e.g. a liquid crystal display device (LCD) to display to patient 20 or another user the operation status of control and power source module 12, implanted pump controller 21, and pump 14, as well as the specific status of removable battery 24 and internal battery 80.

In one example of control and power source module 12, power may be delivered unregulated from removable battery 24 or internal battery 80, e.g via a switch to driver 150 and speakers 90. In contrast to the operation of a component such as speakers 90, however, power management module 140 may manage power delivered from removable battery 24 or internal battery 80 through connector 26 and cable 18 to the primary resonant network 15, using power inverter 148. In one example, first processor 130 may control power bridge 148, which may include circuitry for properly and safely delivering power to internal pump controller 21.

Figure 11:
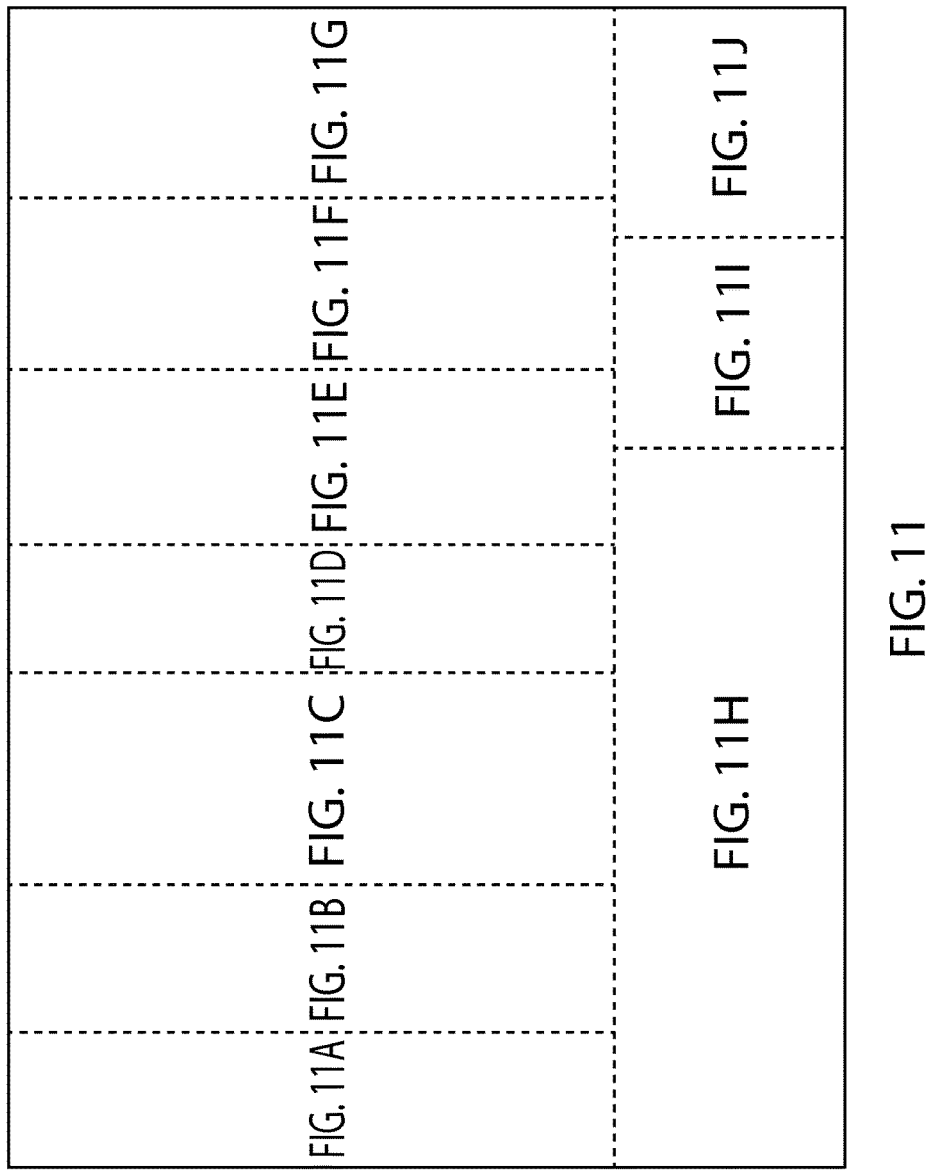
FIGS. 11A-11J ("FIG. 11") are circuit diagrams illustrating circuitry of an example of the power junction of the control and power source module of FIG. 5.
Figure 11A:
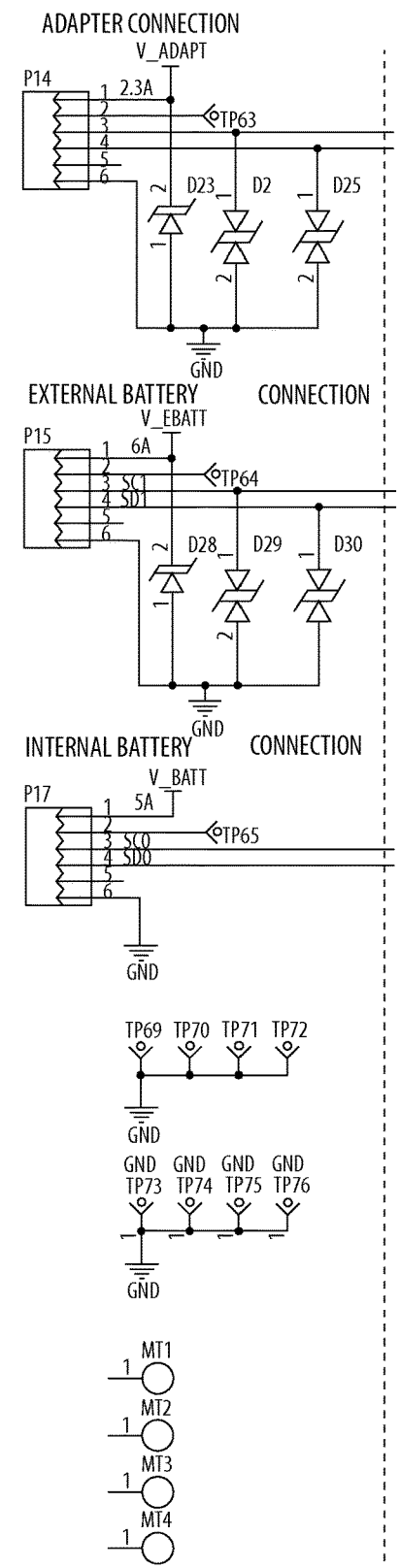
Figure 11B:
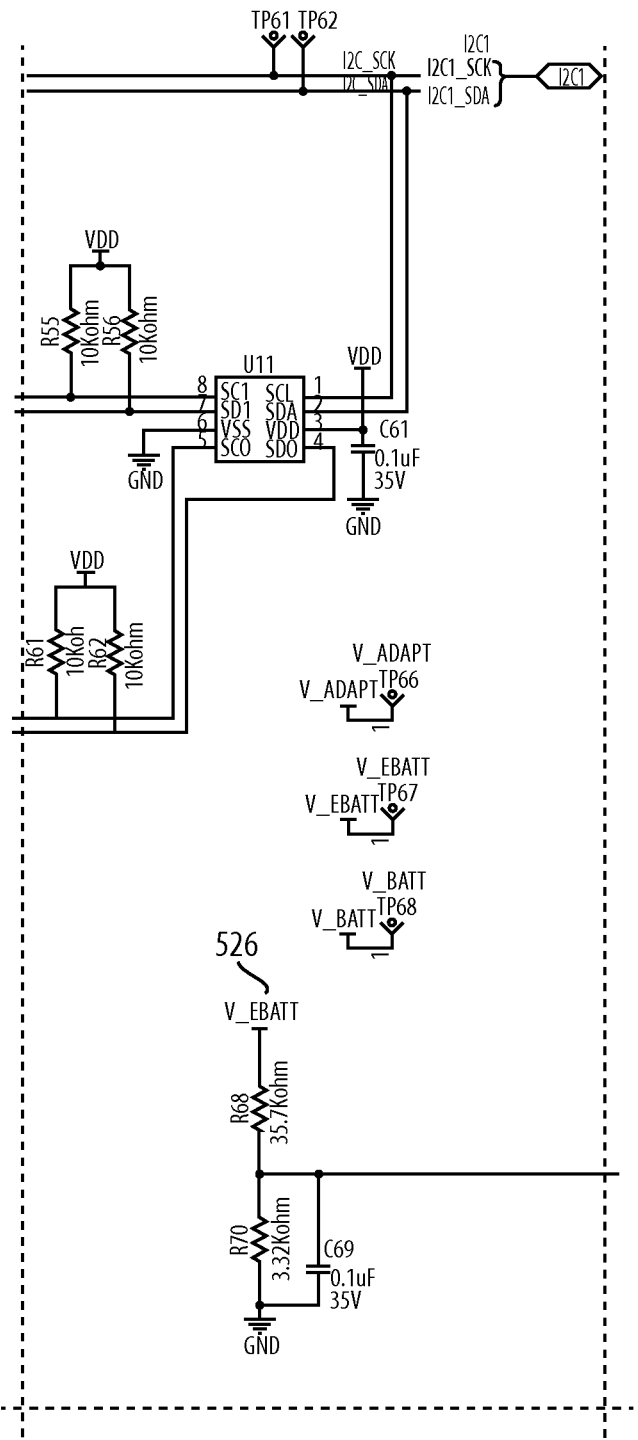
Figure 11C:
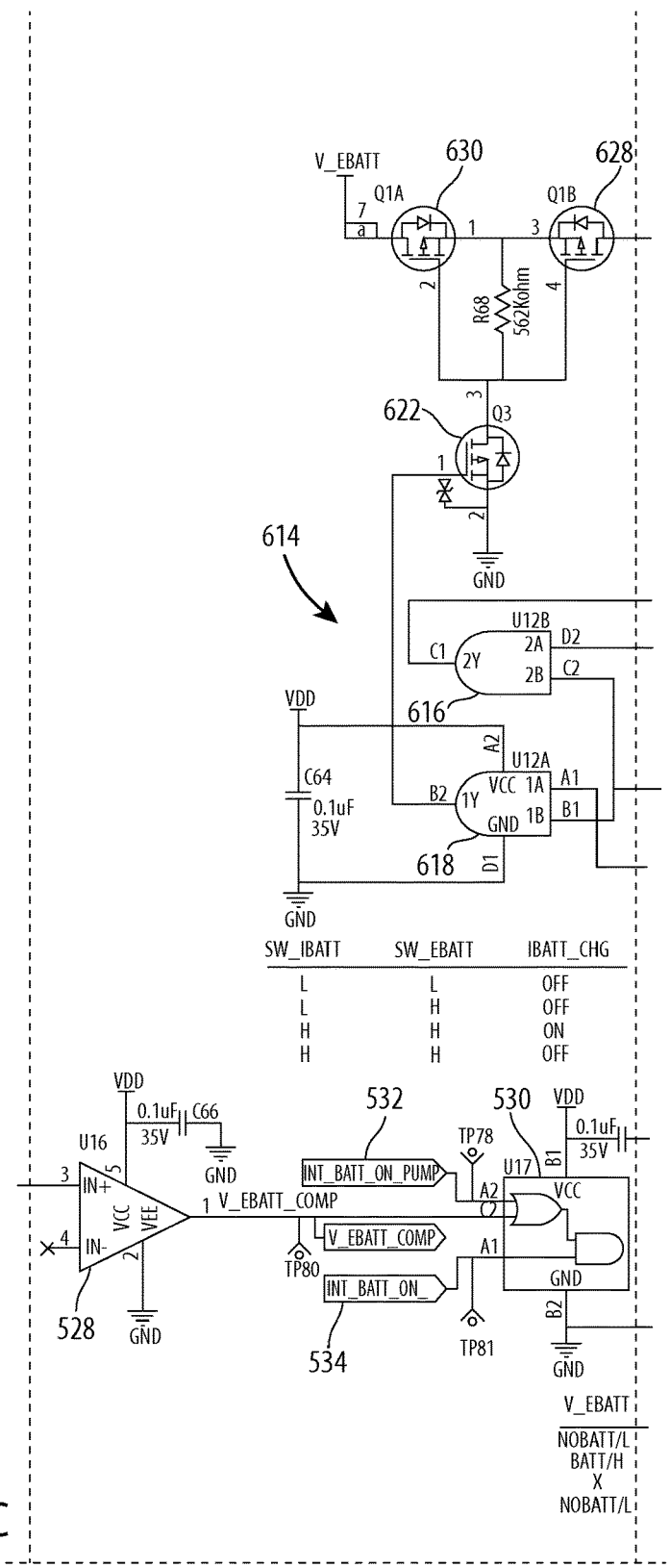
Figure 11D:
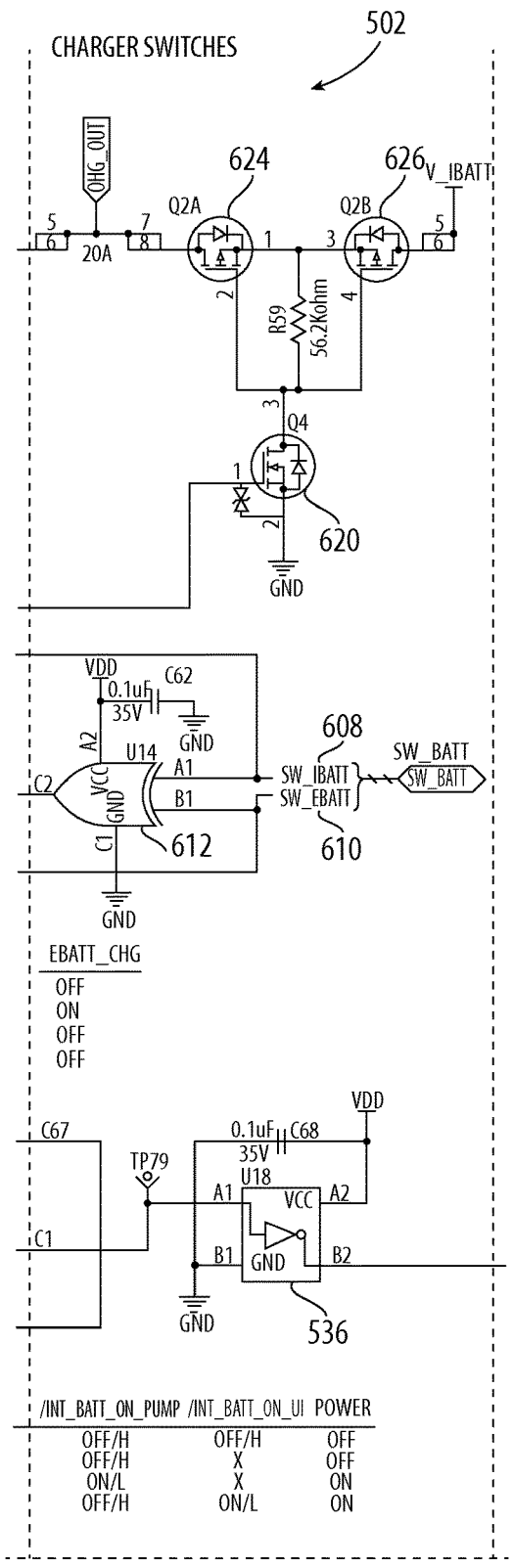
Figure 11E:
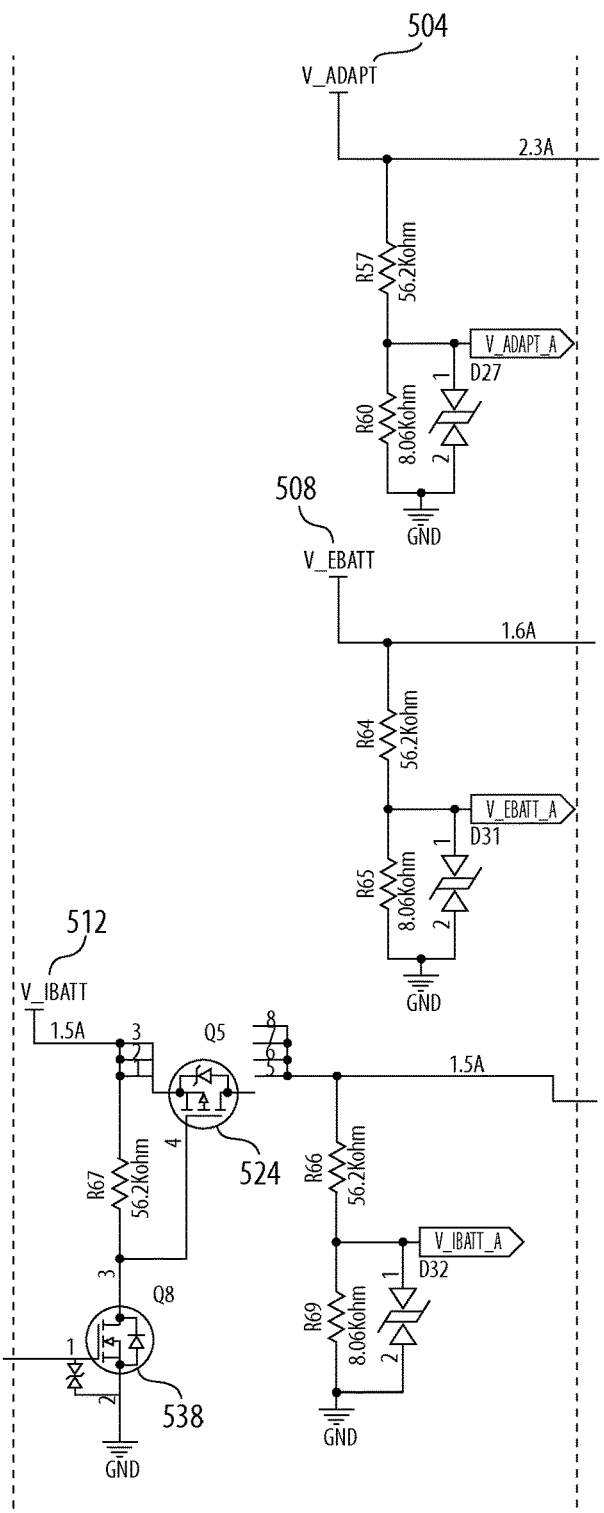
Figure 11F:
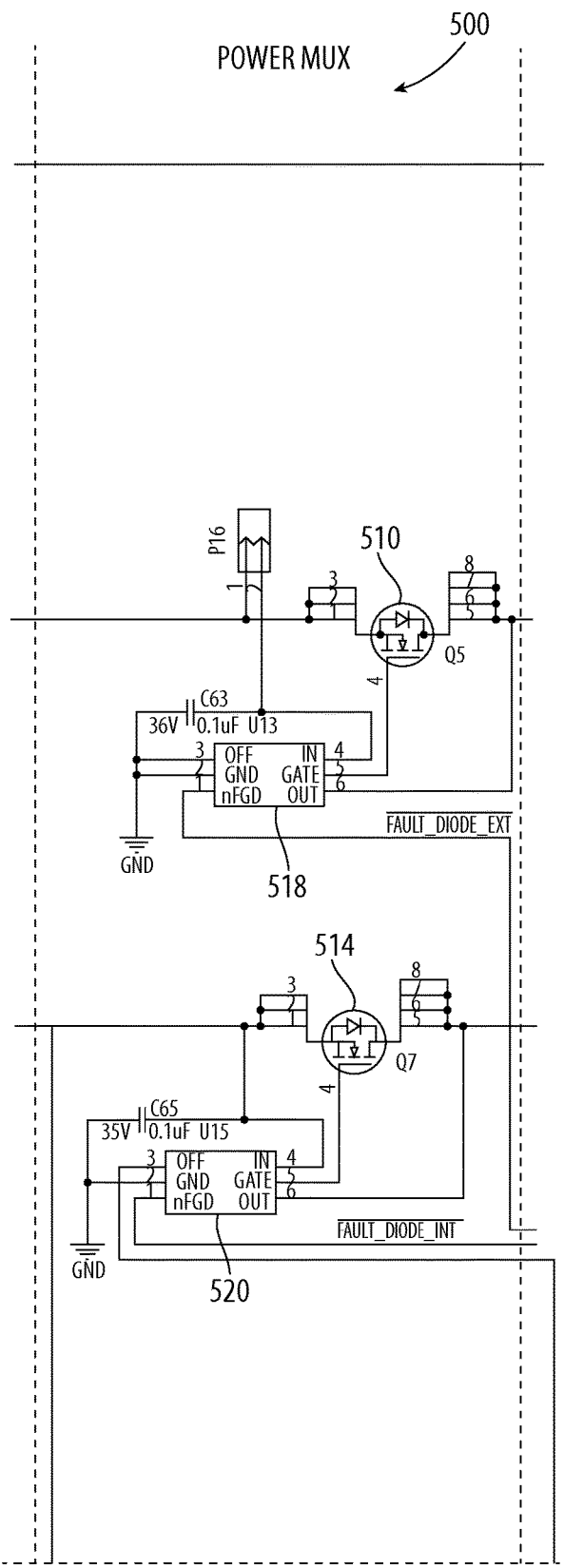
Figure 11G:
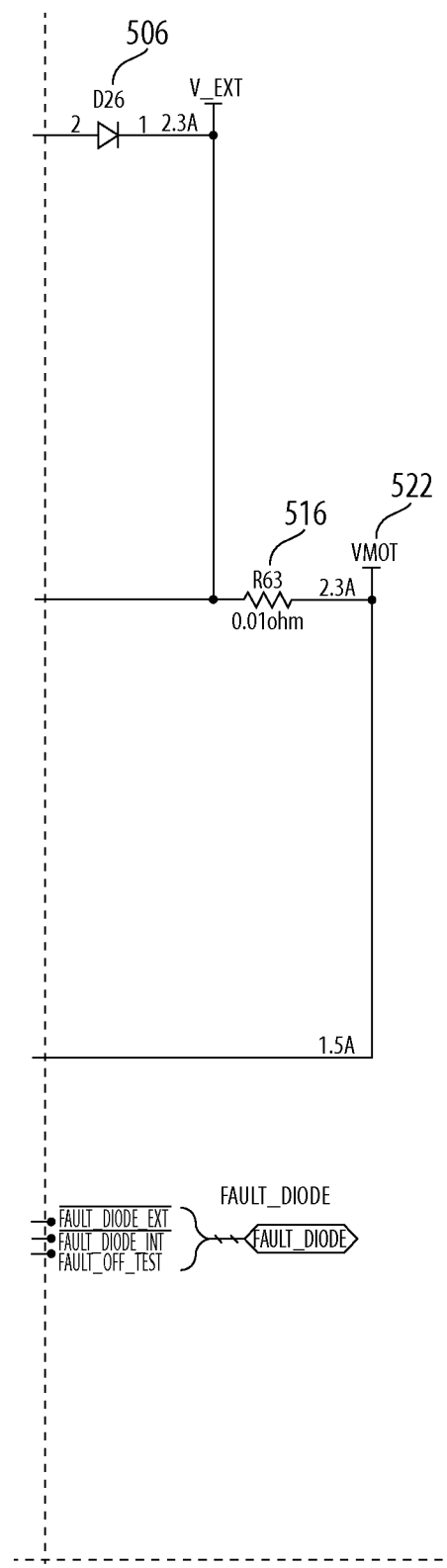
Figure 11H:
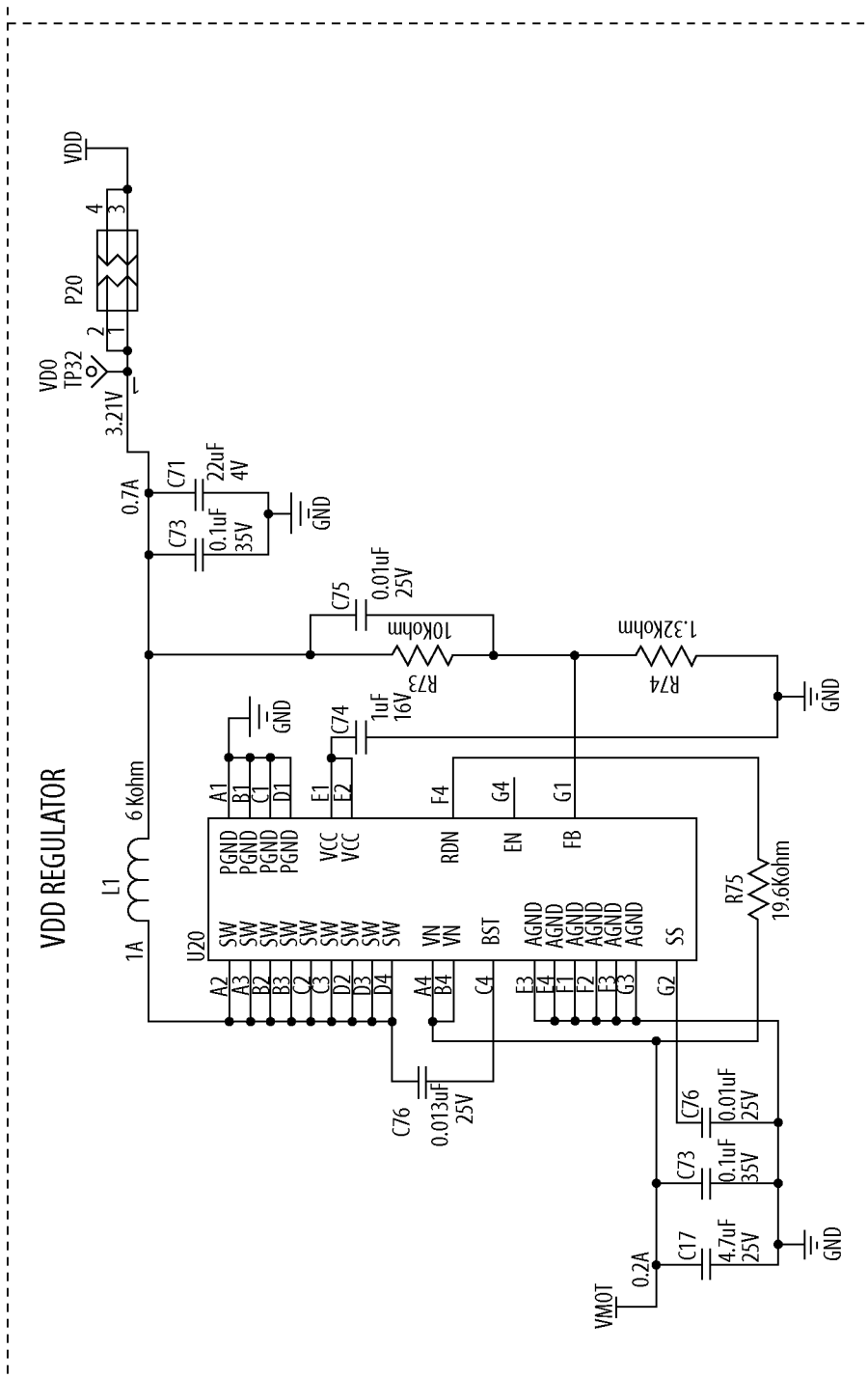
Figure 11I:
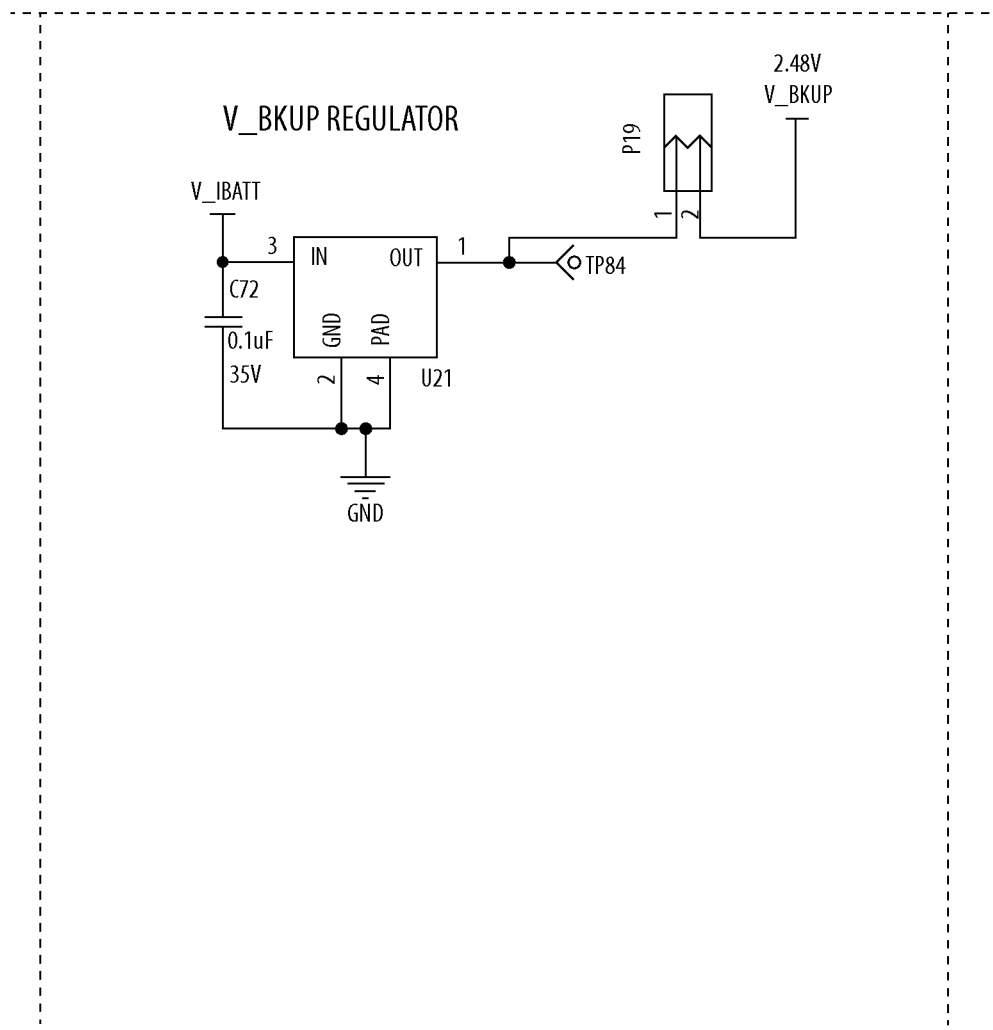
Figure 11J:
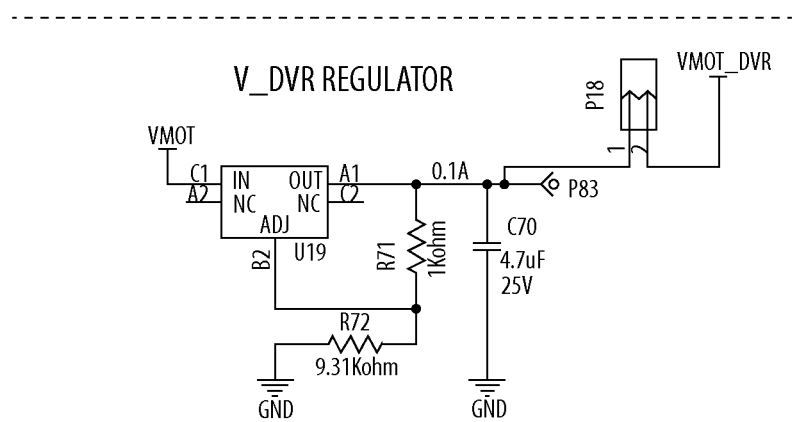

FIG. 11 is a circuit diagram illustrating the circuitry of power junction 146 (FIG. 5) in more detail. As seen in FIG. 11, power junction 146 includes power mux circuitry, shown generally at 500, and charger switches circuitry, shown generally at 502. As described in more detail below, power mux circuitry 500 allows power from several power sources, i.e., a power adapter, removable battery 24, and internal battery 80, to be combined and delivering power from only a single power source to the power inverter 148.

In accordance with this disclosure, power mux circuitry 500 is designed to allow the highest voltage between the power sources, i.e., a power adapter, the removable battery, and the internal battery, to be selected and thus power the pump motor. As seen in FIG. 11, adapter voltage rail 504 is connected to Schottky diode 506, removable battery voltage rail 508 is connected to FET 510, and internal battery voltage rail 512 is connected to FET 514. The cathode of diode 506 and the drain of FET 510 are connected at a first terminal of charger sense resistor 516 and the drain of FET 514 is connected to a second terminal of sense resistor 516. Each of FETs 510, 514 is controlled by a FET controller, namely FET controllers 518, 520, respectively, to keep FETs 510, 514 operating at peak efficiency. One example FET controller that may be used to control FETs 518, 520 is an LM5050-2, available from National Semiconductor.

Each of FETs 518, 520 behave like ideal diodes, thereby effectively creating three "OR"-ing diodes. Whichever of the three voltages rails, i.e., adapter voltage rail 504, removable battery voltage rail 508, and internal battery voltage rail 512, is highest will appear at the common node between the three, i.e., sense resistor 516. For example, removable battery voltage rail 508 and internal battery voltage rail 512 may each have a maximum voltage of 16.8 Volts (V) and adapter voltage rail 504 may have a maximum voltage of 18V. Whenever an adapter is connected to a control and power source module, e.g., control and power source module 12, the adapter voltage will always be selected as the voltage to power the pump motor via motor bus 522 (an unregulated high voltage rail to the pump). That is, adapter voltage rail 504 will be reduced by about 0.2-0.3V by Schottky diode 506 to a voltage of about 17.7-17.8V, and the removable battery voltage rail 508 and internal battery voltage rail 512 will be reduced to a voltage of about 16.1-16.2V due to the ideal diode drop (0.6V-0.7V) of FETs 510, 514. It should be noted that the adapter voltage (either AC or DC) is designed to be higher than either the removable or internal battery voltages so that power mux circuitry 500 automatically defaults to the adapter as the power supply to motor bus 522.

Still referring to power mux circuitry 500, internal battery voltage rail 512 is also connected to FET 524. FET 524 acts as a switch and is included in power mux circuitry 500 to allow the internal battery to be connected and disconnected. In addition, if not for FET 524, the internal battery and the removable battery would drain at the same voltage level.

To the left of FET 524 in FIG. 11, logic circuitry is included to control the operation of FET 524. Generally, the removable battery voltage rail, shown at 526, is fed into comparator 528, which includes a 1.25V internal reference voltage. The output of comparator 528 is fed into 3-input OR-AND gate 530 along with two internal battery signals, 532, 534. In particular, the output of comparator 528 is fed along with internal battery signal 532 from a pump processor, e.g. first processor 130 of control and power source module 12 of FIG. 5, into the OR portion of OR-AND gate 530, and internal battery signal 534 from a UI processor, e.g. second processor 132 of control and power source module 12 of FIG. 5, is fed along with the output of the OR portion into the AND portion of OR-AND gate 530. In this manner, the operation of FET 524, and thus whether the internal battery is connected to the control and power source module, may be controlled (via inverter gate 536 and FET 538). For example, as a safety feature, if there is no removable battery voltage, then both the pump processor and the UI processor must agree and generate control signals in order for the system to shut off FET 524 (and thus disconnect the internal battery from the circuit and the control and power source module).

As another safety feature, a sudden drop in the removable battery voltage will turn FET 524 ON, thereby connecting the internal battery to the control and power source module. In particular, comparator 528 compares the removable battery voltage to its internal reference and provides an output, e.g., a logical low, to the OR portion of OR-AND gate 530. The output of the OR portion is fed along with internal battery signal 534, e.g., a logical low, into the AND-portion of OR-AND gate 530, which then turns on FET 524 via inverter gate 536 and FET 538, thereby connecting the internal battery to the control and power source module.

In other examples, FET 524 may be automatically controlled based on load demands. For example, during power up, the pump motor may draw more power than during a steady state condition. Using the techniques described above, power mux circuitry 500 may automatically switch over from the removable battery to the more power-dense internal battery until the pump motor reaches a steady state condition. In operation, if the removable battery cannot sustain the load, then removable battery voltage rail 526 temporarily collapses, resulting in comparator 528 firing, thereby turning on FET 524 and connecting the internal battery voltage rail 508 to motor bus 522.

In some examples, the pump processor may control FET 524 during pump start up by outputting specific control signals. It may be desirable for the first processor to control FET 524 during start up because allowing the removable battery voltage to temporarily collapse may generate unnecessary heat. In addition to start up, physiological conditions may cause the pump motor to work harder and thus increase the load. For example, certain medications may result in thickening of the blood, and certain activities, such as lifting heavy objects, may cause vasoconstriction. In either case, the pump may need to work harder and, as a result, draw more power from the power source. Using the techniques described above, an alternate power source may be used to accommodate increased demand from the pump.

Figure 12:
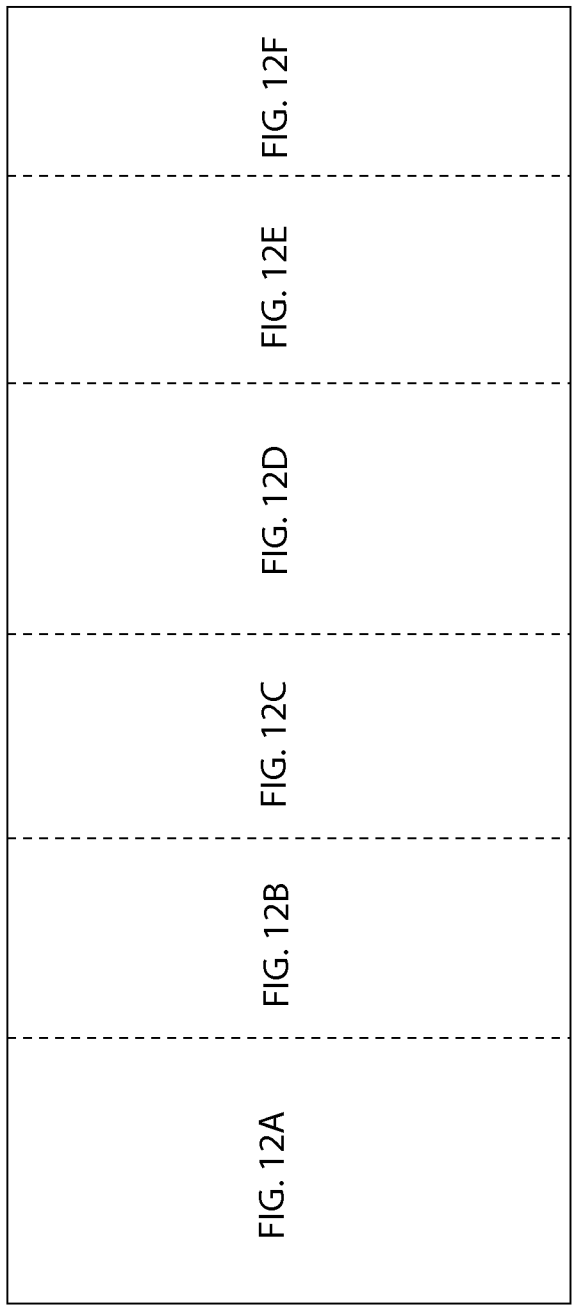
FIGS. 12A-12F ("FIG. 12") are circuit diagrams illustrating circuitry of an example of the charger of the control and power source module of FIG. 5.
Figure 12A:
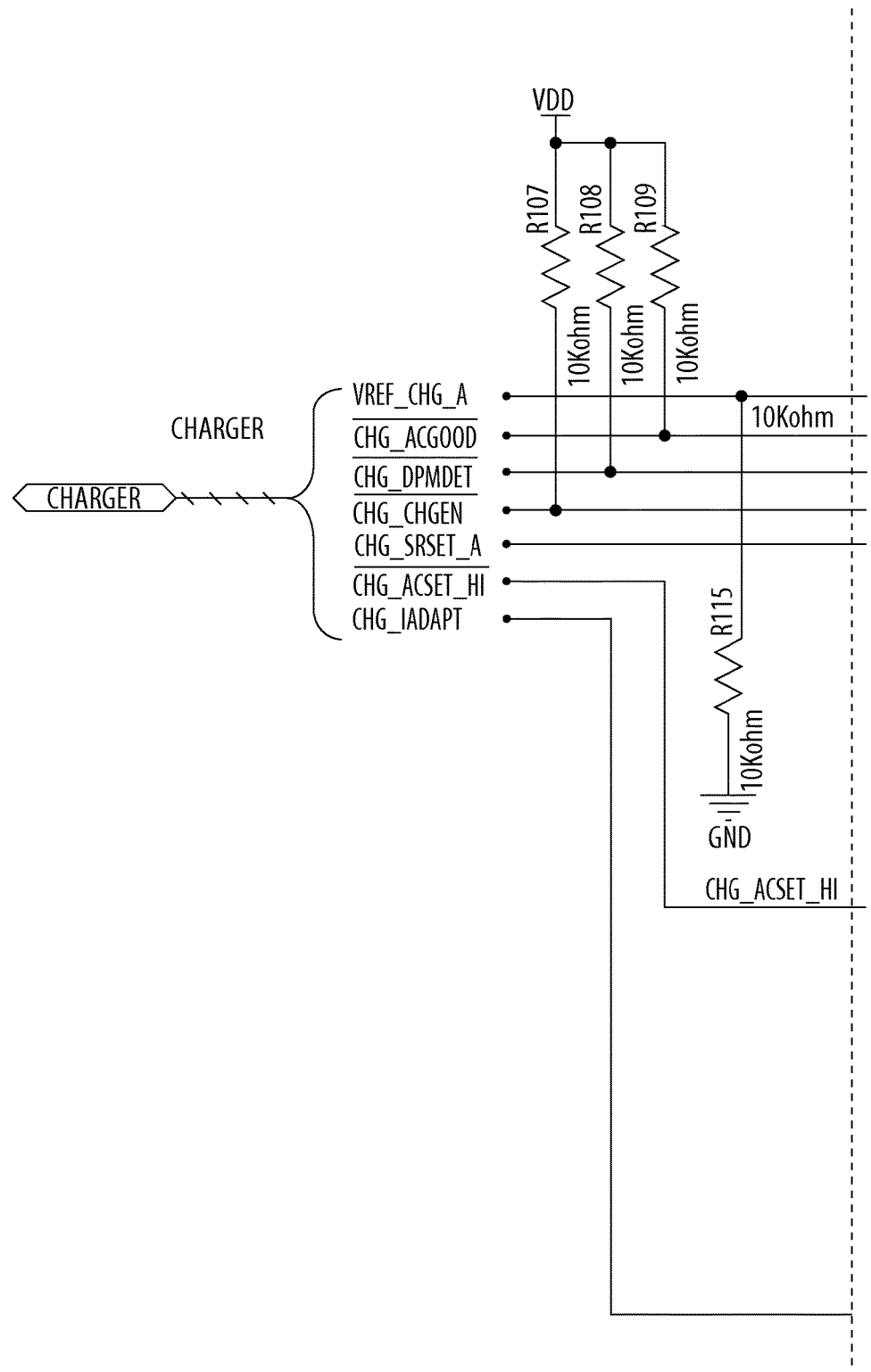
Figure 12B:
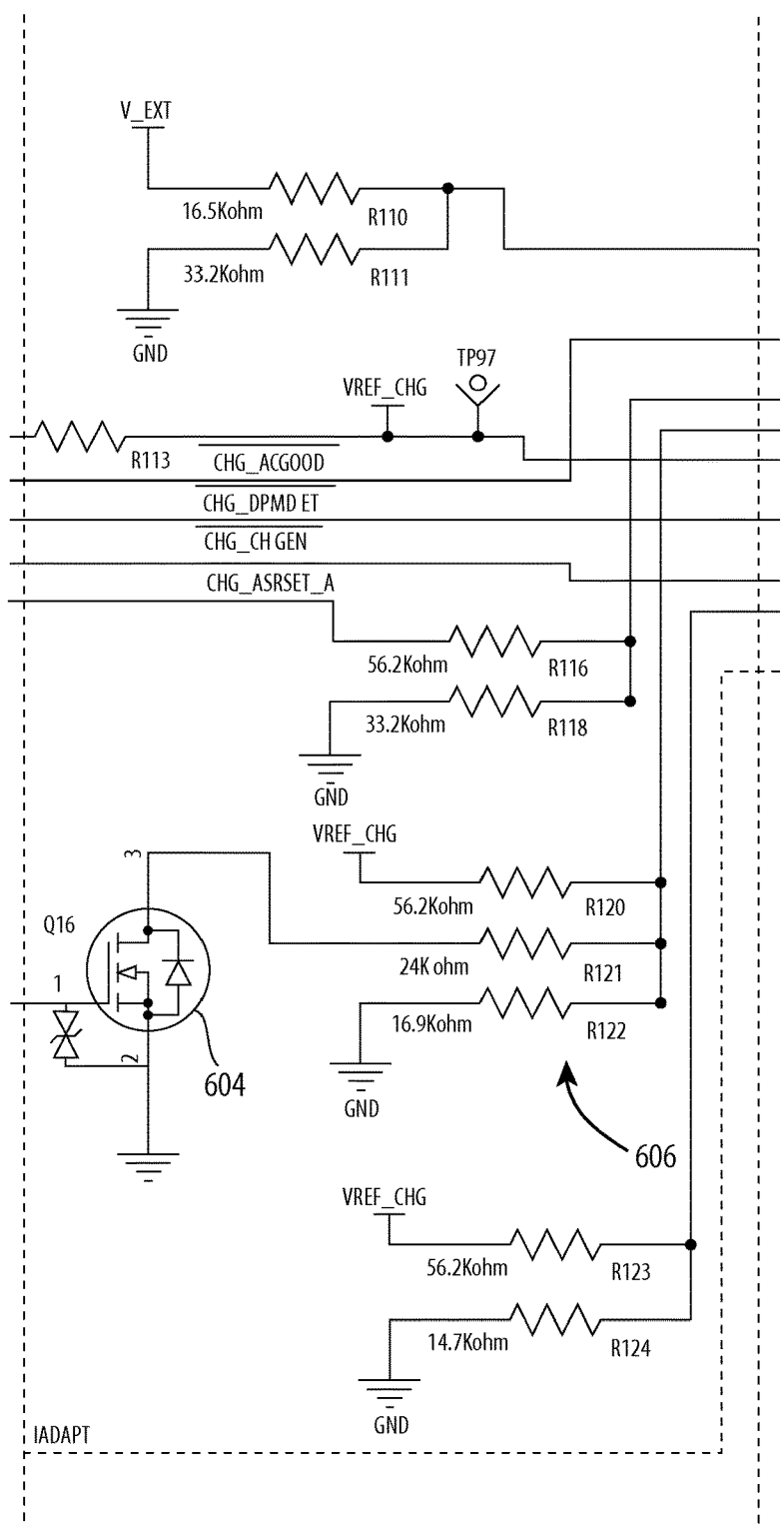
Figure 12C:
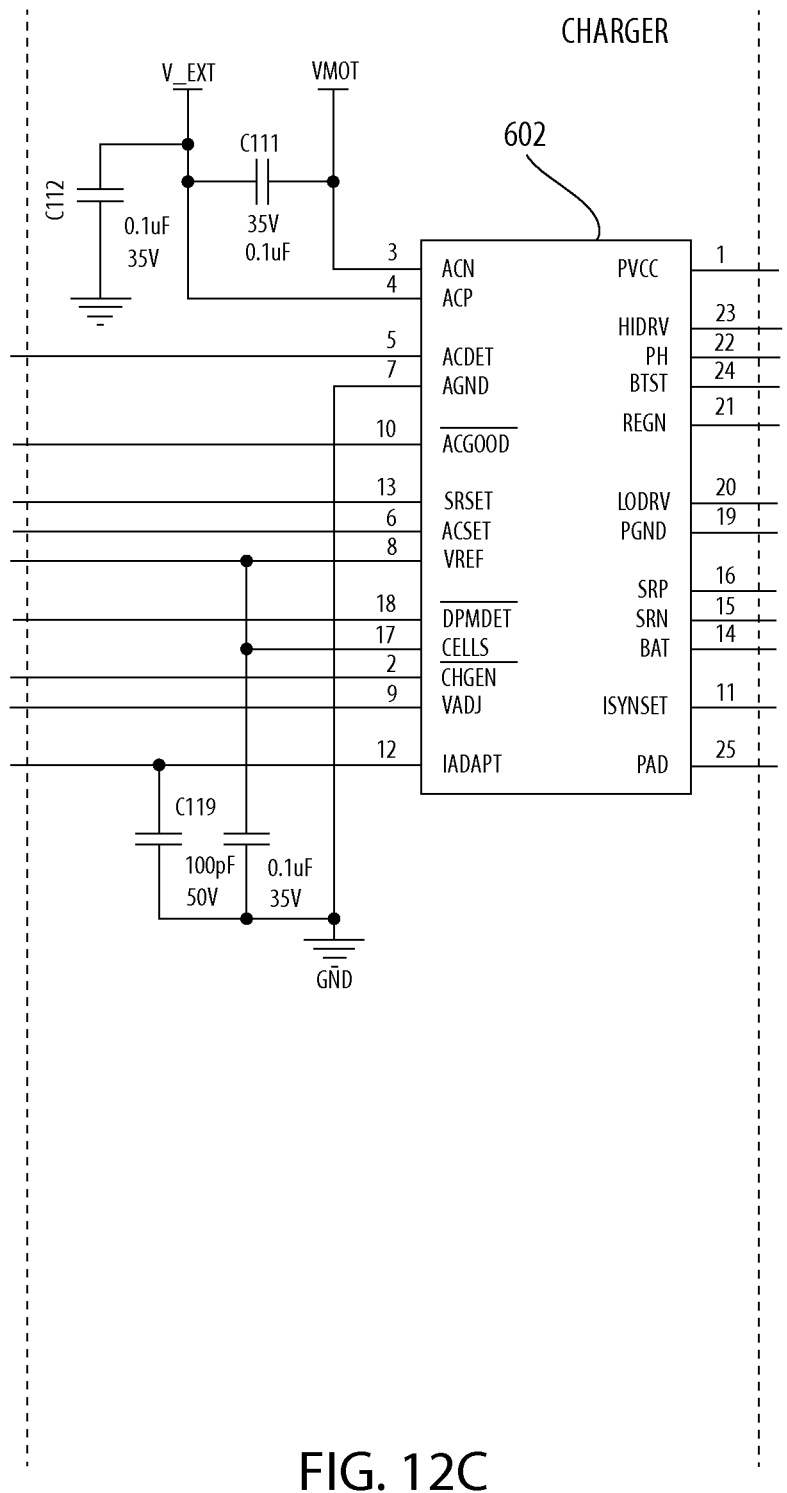
Figure 12D:
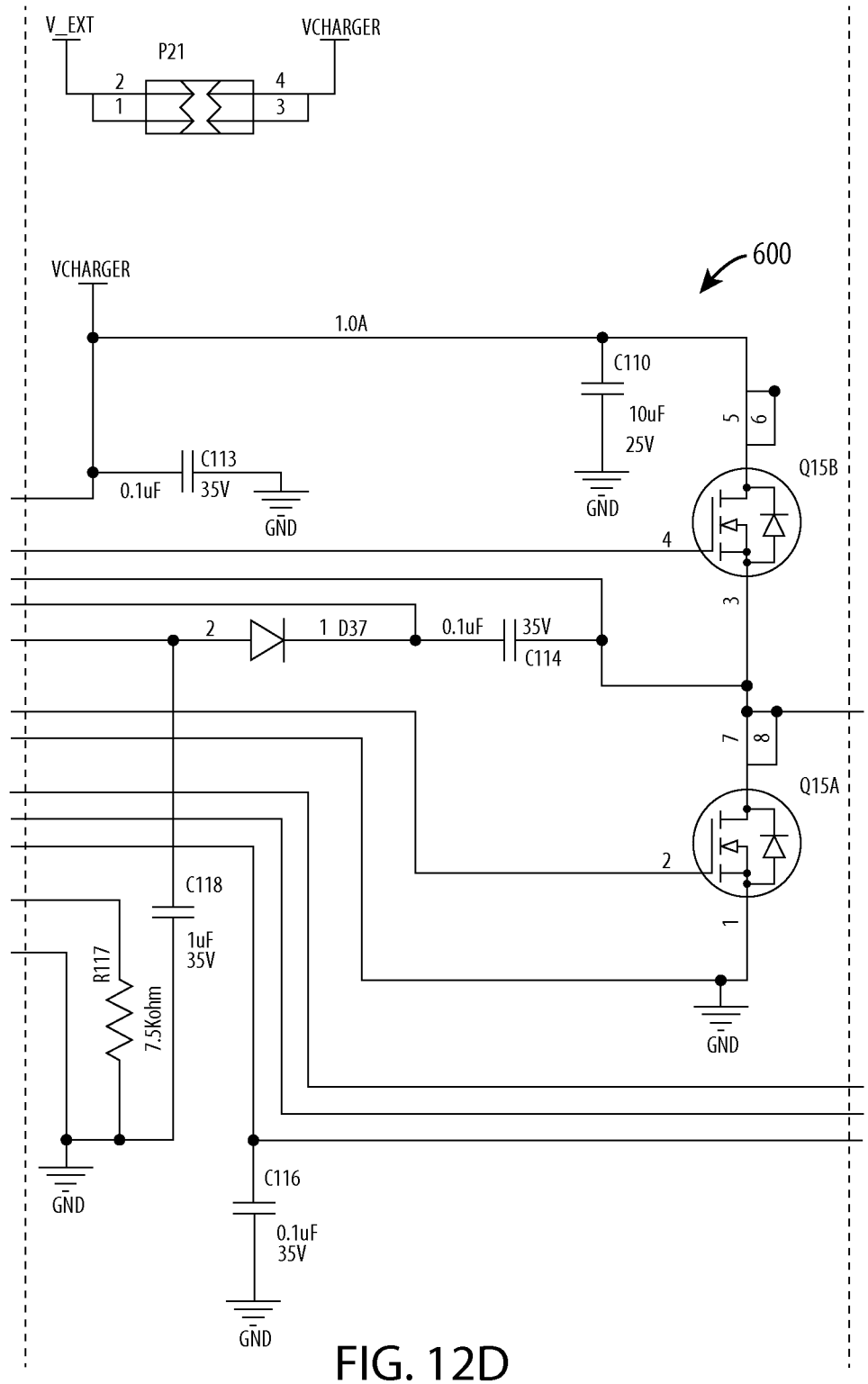
Figure 12E:
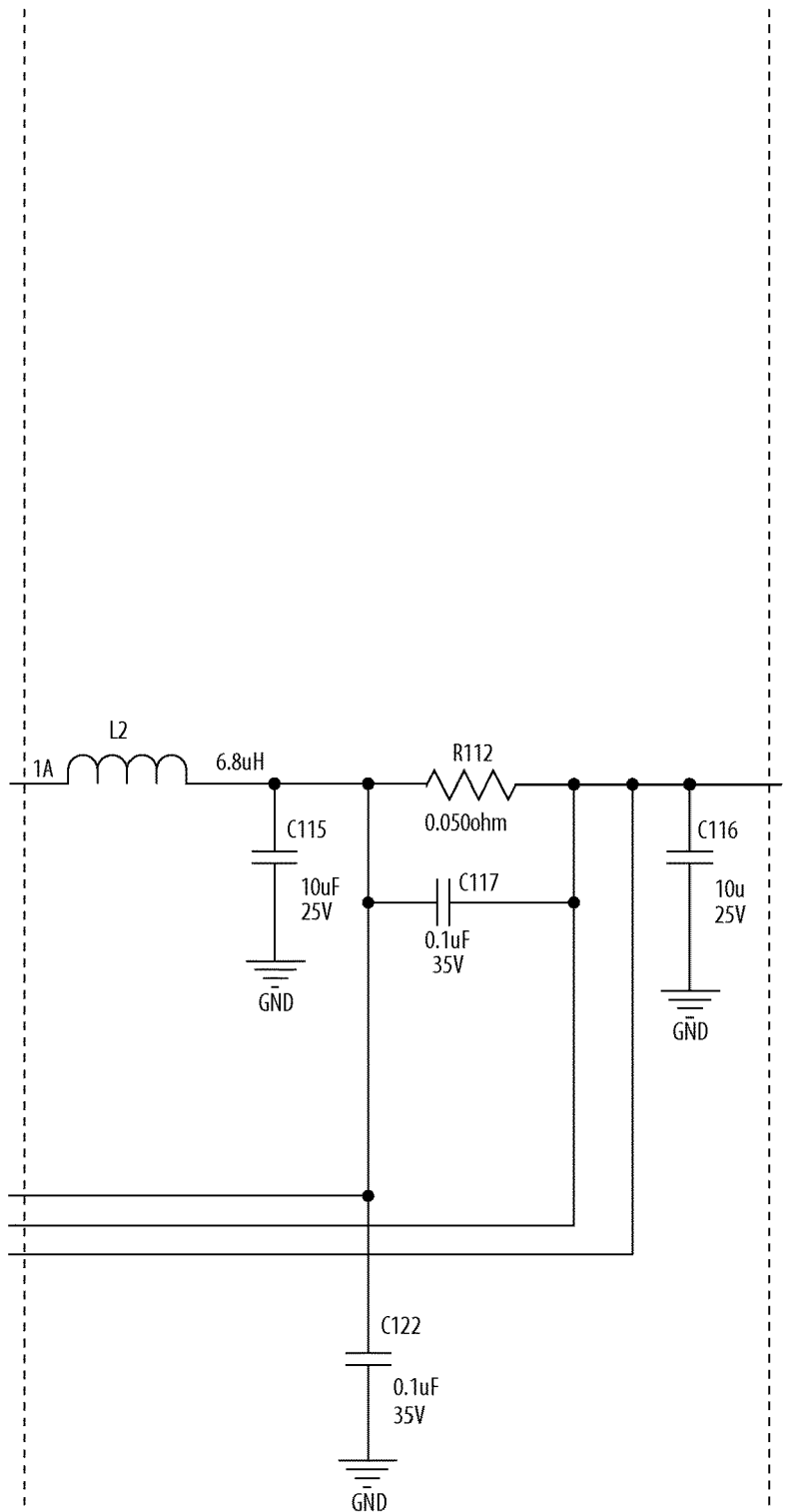
Figure 12F:
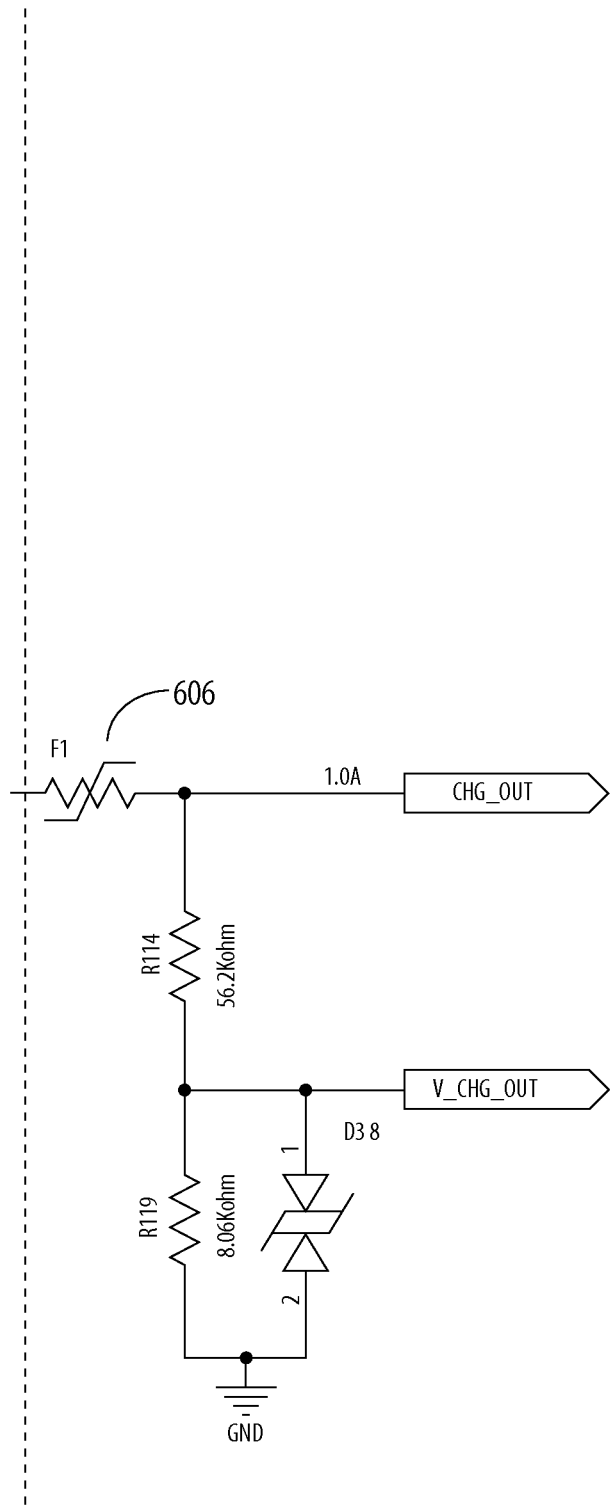

It should be noted that in order to save power, the second processor may be configured to shut off if no services are being provided. The second processor may periodically wake up, e.g., once every second, to verify that the first processor is working properly, thereby providing a cross-checking function. In some examples, the first processor may send a signal to the second processor, e.g., via a serial peripheral interface (SPI) bus, and receives a predictable response. FIG. 12 is a circuit diagram illustrating the circuitry of charger 142 (FIG. 5) in more detail. In FIG. 12, charger circuitry 600, via battery charger 602, provides dynamic power management, which provides less power to the battery if the system is requiring more power so that the system is not starved of power. Using the techniques of this disclosure, charger circuitry 600 may change the power system limit based on the battery from which the system is drawing power.

As mentioned above and as seen in FIG. 11, both external power sources, i.e., the adapter and the removable battery, are connected to sense resistor 516. Battery charger 602 measures how much power is coming in to the system and battery charger 602 knows how much power it is providing to the removable battery during charging. Using dynamic power management, charger circuitry 600 may change the power system limit based on the battery from which the system is drawing power in order to provide less power to the battery during charging so that the system is not deprived of power. The power system limit is how much power the system needs and, in accordance with this disclosure, is settable. In particular, charger circuitry 600 includes FET 604 and a resistor divider network, shown generally at 606. Based on whether the system needs more power or less power, the pump processor controls FET 604 to turn ON or OFF, thereby switching in or switching out a leg of resistor divider network 606. In some example implementations, the power system limit may be controlled via a digital-analog converter (DAC) output.

In addition, in accordance with this disclosure, sense resistor 516 (FIG. 11) is connected to the external power sources, namely the adapter and the removable battery, and not the internal battery. Sense resistor 516 need not be connected to the internal battery because, by design, the system does not charge from the internal battery.

Further, charger circuitry 600 includes resettable fuse 606 for safety. It should be noted that resettable fuse 606 may be included on the charger board in some example implementations.

Referring again to FIG. 11, charger switches circuitry 502 provides a fail-safe means to control whether the internal battery or the removable battery receives power from the charger, thereby allowing the system to use a single charger circuit. Charger switches circuitry 502 includes a combination of FETs and logic circuitry that allows the pump processor to select which battery is charging. The logic circuitry eliminates the possibility of a short between the internal and removable batteries.

In charger switches circuitry 502, the pump processor provides two control signals, namely internal battery switch signal 608 and removable battery switch signal 610, to exclusive-OR gate 612. The output of exclusive-OR gate 612 is fed into one input of each of the AND gates of a dual 2-input positive AND gate, shown generally at 614. The other two inputs of the AND gates of dual 2-input AND gate 614 are supplied by internal battery switch signal 608 and removable battery switch signal 610. In particular, internal battery switch signal 608 is supplied to an input of AND gate 616 and removable battery switch signal 610 is supplied to an input of AND gate 618. The output of AND gate 616 turns on FET 620, which causes the internal battery to begin charging through FETs 624 and 626. The output of AND gate 618 turns on FET 622, which causes the removable battery to begin charging through FETs 628 and 630.

In one example implementation, the removable battery begins charging if internal battery switch signal 608 is a logic level low and removable battery switch signal 610 is a logic level high, and the internal battery begins charging if internal battery switch signal 608 is a logic level high and removable battery switch signal 610 is a logic level low. If internal battery switch signal 608 and removable battery switch signal 610 are at the same logic level (low or high), then neither battery is charging.

FIGS. 13A and 13B are plan and elevation views, respectively, of removable battery 24 and battery release latch 700 for use with a control and power source module according to this disclosure, e.g. control and power source module 12 of FIGS. 2A-4B. Although only one battery release latch 700 is illustrated in the FIG. 13A, a second similarly configured battery release latch may be arranged on the opposite side of the control and power source module such that both latches may be engaged to release removable battery 24. In the example of FIGS. 13A and 13B, battery release latch 700 includes push button 702, catch 704, pivot 706, and spring return 708. Removable battery 24 includes stop 710 configured to engage catch 704 on battery release latch 700 to lock the battery in housing 22 of control and power source module 12.

In FIGS. 13A and 13B, push button 702 and catch 704 of battery release latch 700 are connected and pivot about pivot 706. Spring return 708 is arranged to abut and engage push button 702 to bias the battery lease latch 700 such that catch 704 pivots about pivot 706 to engage stop 710 on removable battery 24. To release removable battery 24, a user may push on push button 702, causing push button 702 and catch 704 to pivot about pivot 706 such that catch 704 moves out of engagement with stop 710 on removable battery 24. Removable battery 24 may be manually removed by the user after unlatching battery release latch 700 or control and power source module 12 may include automatic eject mechanism that ejects the battery at least partially out of housing 22 when the latch is no longer engaging the battery.

FIGS. 14A and 14B are broken plan and elevation views, respectively, of removable battery 24 and another type of battery release latch 800 for use with a control and power source module according to this disclosure, e.g. control and power source module 12 of FIGS. 2A-4B. FIGS. 14C and 14D are section views cut along section line A-A of FIG. 14A illustrating two different examples of battery release latch 800. Although only one battery release latch 800 is illustrated in the FIGS. 14A-14D, a second similarly configured battery release latch may be arranged on the opposite side of the control and power source module such that both latches may be engaged to release removable battery 24. In FIGS. 14A and 14B, battery release latch 800 is integral with removable battery 24 and configured with push buttons that may pivot about the X-axis (horizontal in the view of FIG. 14A) or the Y-axis (vertical in the view of FIGS. 14A and 14B). The examples illustrated in FIGS. 14C and 14D both include push buttons configured to pivot about axis Y.

However, in other examples, a battery release latch may be configured in accordance with the examples of FIGS. 14C and 14D with the push buttons pivoting about the X-axis.

In the example of FIG. 14C, battery release latch 800A integral with removable battery 24 includes push button 802, catch 804, and resilient tab 806. Housing 22 includes stop 808 configured to engage catch 804 on battery release latch 800A to lock the battery in housing 22 of the control and power source module. Push button 802 and catch 804 of battery release latch 800A are configured to rotate at resilient tab 806. Resilient tab 806 may, in one example, be formed from a resilient material that biases battery lease latch 800A such that catch 804 pivots about resilient tab 806 to engage stop 808 on housing 22. To release removable battery 24, a user may push on push button 80, causing resilient tab 806 to flex, which permits push button 802 and catch 804 to pivot about resilient tab 806 such that catch 804 moves out of engagement with stop 808 on housing 22. Removable battery 24 may be manually removed by the user after unlatching battery release latch 800A or the control and power source module may include an automatic eject mechanism that ejects the battery at least partially out of housing 22 when the latch is no longer engaging the battery.

In the example of FIG. 14D, battery release latch 800B integral with removable battery 24 includes push button 802, catch 804, pivot 810, and spring return 812. In this example, push button 802 and catch 804 of battery release latch 800A are configured to rotate about pivot 810. Spring return 812 is arranged to abut and engage push button 802 to bias the battery lease latch 800A such that catch 804 pivots about pivot 810 to engage stop 808 on housing 22. To release removable battery 24, a user may push on push button 80, compressing spring return 812 and causing push button 802 and catch 804 to pivot about pivot 810 such that catch 804 moves out of engagement with stop 808 on housing 22. Removable battery 24 may be manually removed by the user after unlatching battery release latch 800B or the control and power source module may include an automatic eject mechanism that ejects the battery at least partially out of housing 22 when the latch is no longer engaging the battery.

Wireless Power Transfer System

Figure 15:
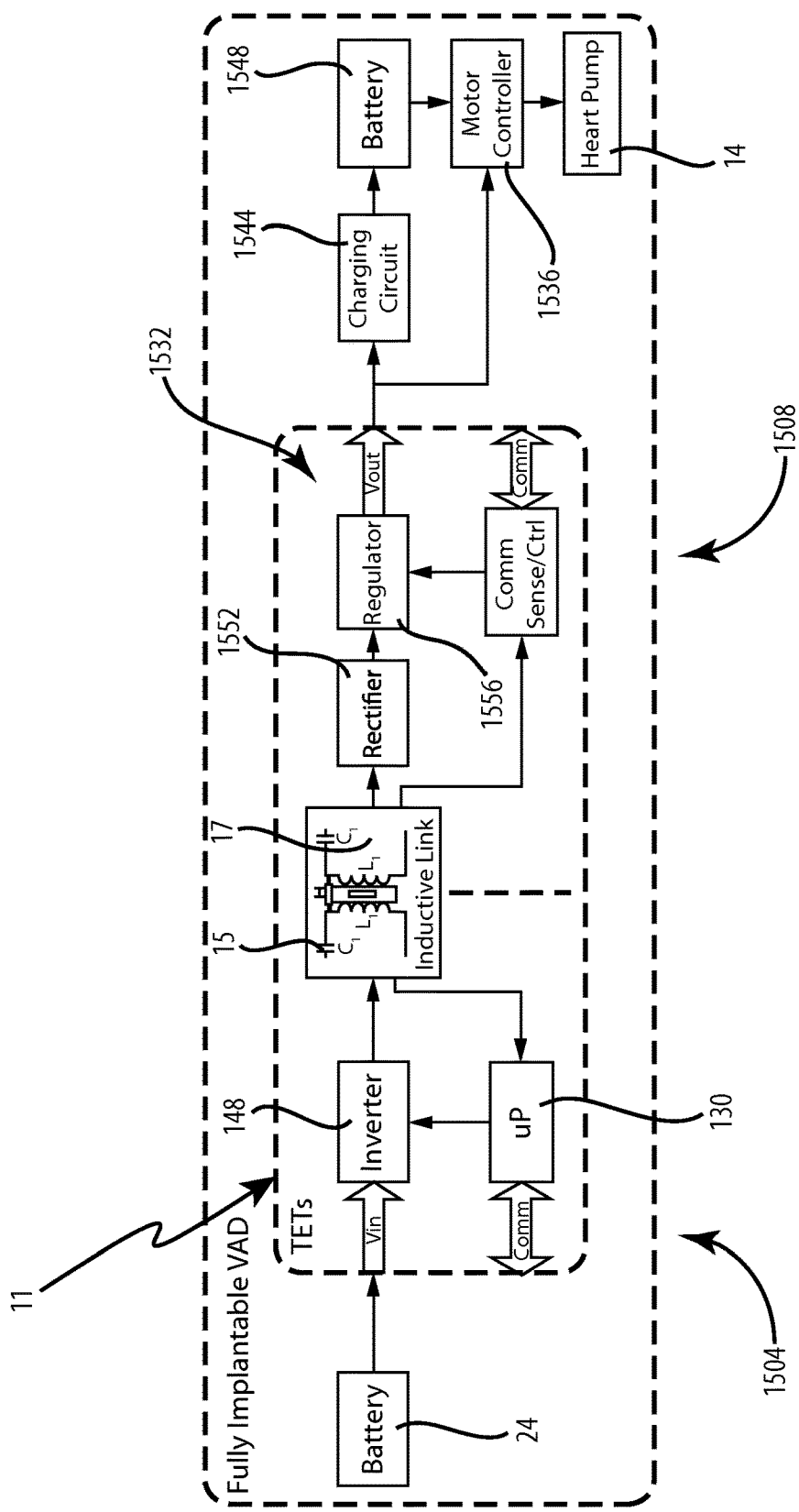
FIG. 15 is a block diagram of a wireless power transfer system in accordance with embodiments discussed herein.

FIG. 15 is a block diagram of the wireless power transfer system 11 shown in FIG. 1. The system 11 may be referred to as a transcutaneous energy transfer system (TETS) when applied to implantable electronic applications. The system 11 has an external assembly 1504 that is provided at an external location outside of a subject and an internal assembly 1508 that is implanted within the subject. The internal assembly includes an implantable medical device. The implantable medical device may be any medical device capable of being implanted in a subject, such as a heart pump, an artificial heart, a right ventricle assist device, a left ventricle assist device, a BIVAD, a minimally invasive circulatory support system, a cardiac pace maker, and so on. While the implanted device may be any implantable medical device, this disclosure describes the transcutaneous energy transfer system 11 in the context of a heart pump 14 by way of example and not limitation.

Figure 16:
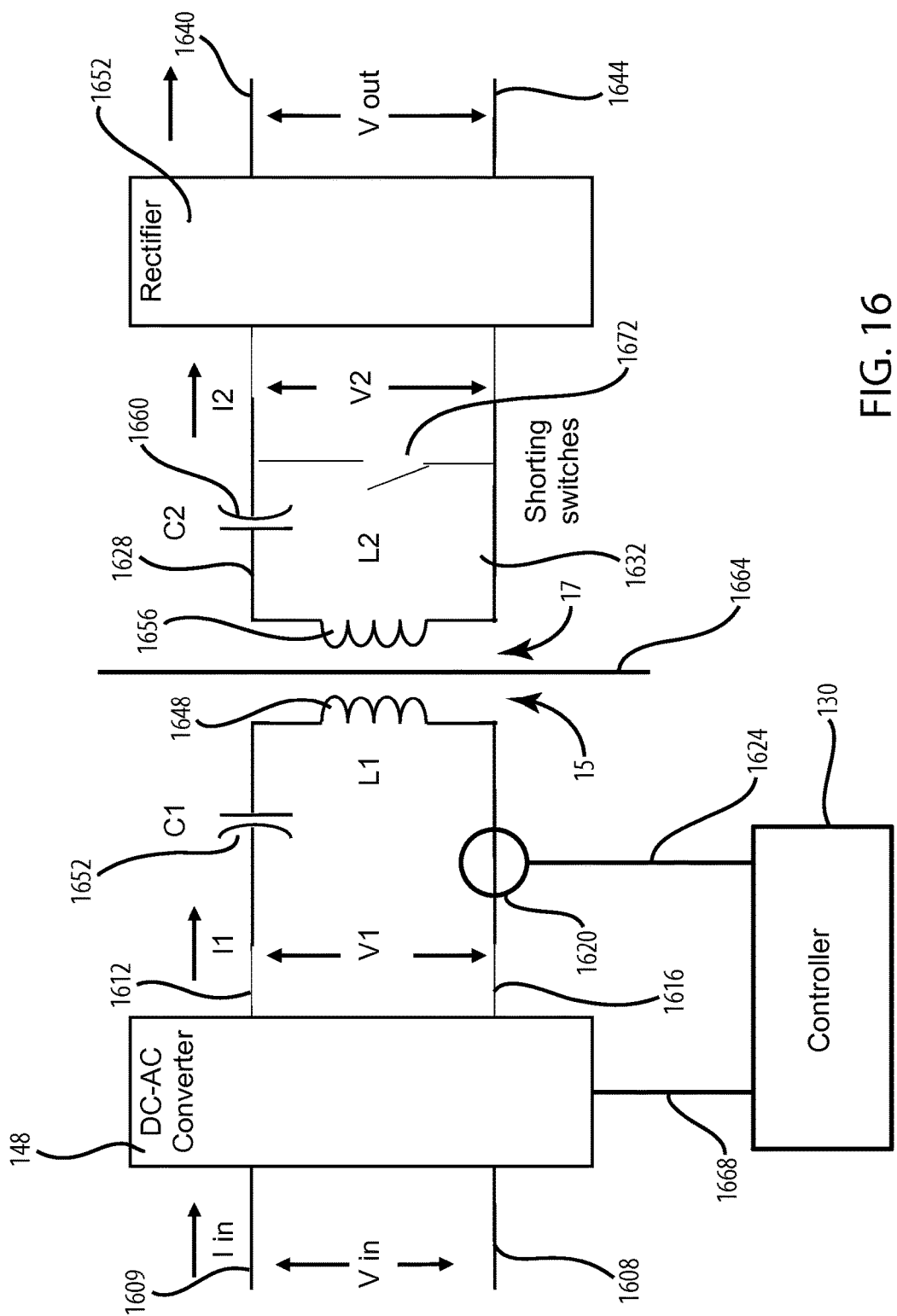
FIG. 16 is circuit diagram for certain components of the system shown in FIG. 15.

As shown in FIG. 15, the external assembly 1504 may include the external resonant network 15. Similarly, the internal assembly 1508 may include the internal resonant network 17. The external assembly 1504 and the internal assembly 1508 are also shown in FIG. 16, which is a circuit diagram that includes certain components of the transcutaneous energy transfer system 11. As shown in FIG. 16, the external resonant network 15 may include an external coupler in the form of an inductive coil 1648 and a capacitor 1652 connected in series. Similarly, the internal resonant network 17 may include an internal coupler in the form of an inductive coil 1656 and a capacitor 1660 connected in series. It should be appreciated that the series-series topology illustrated in FIG. 16 is shown by way of example and not limitation. Alternative embodiments may be used that employ different circuit topologies, such as series-parallel, parallel-series, parallel-parallel and so on.

Figure 17A:
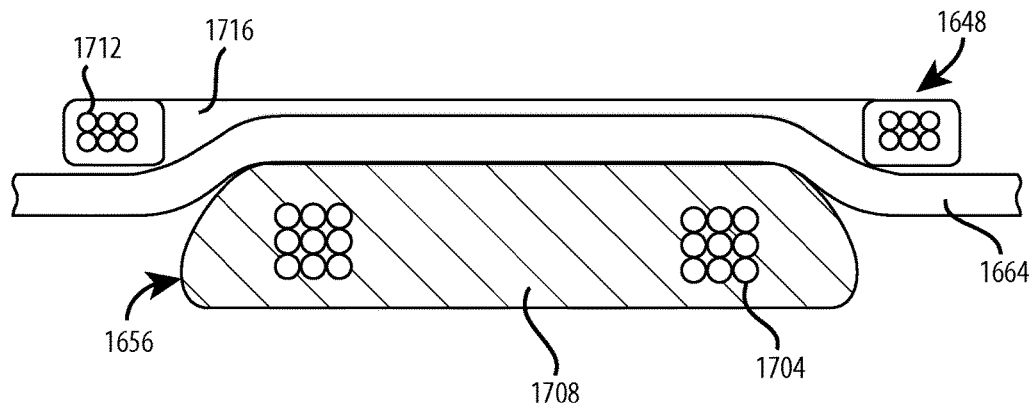
FIGS. 17A and 17B are schematic illustrations of the internal and external coils shown in FIG. 1.
Figure 17B:
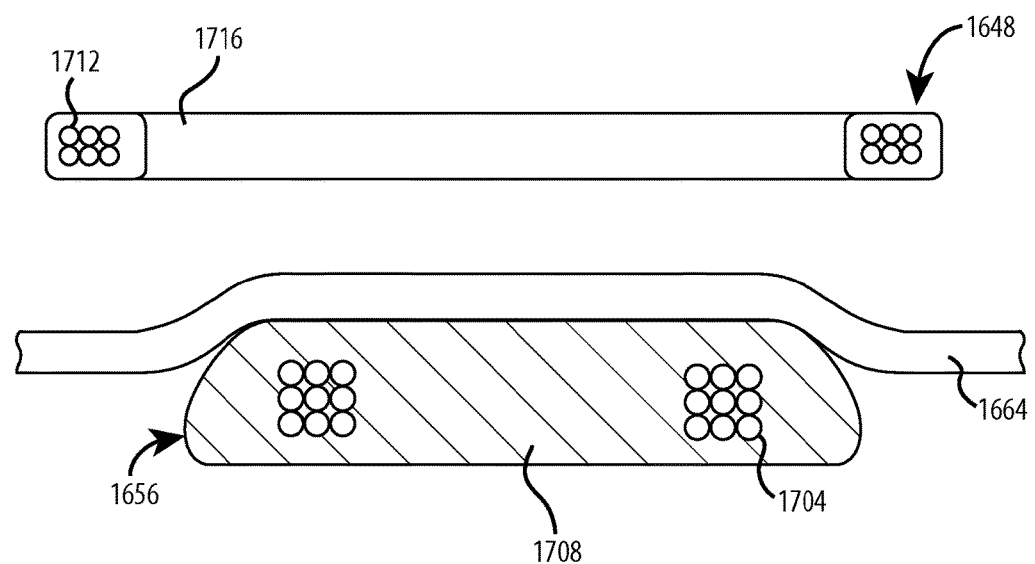

FIGS. 17A and 17B are schematic illustrations of the internal 1656 and external 1648 coils. In FIG. 17A, the internal coil 1656 is disposed beneath the skin 1664 of a subject, and the external coil 1648 is disposed generally adjacent the internal coil 1656. In FIG. 17B, the internal coil 1656 is disposed beneath the skin 1664 of a subject, and the external coil 1648 is disposed at some distance from the internal coil 1656. As shown in FIGS. 17A and 17B, the internal coil 1656 may have a plurality of conductive windings 1704 disposed in a circular insulating member 1708. Similarly, the external coil 1648 may have a plurality of conductive windings 1712 disposed in an insulating ring 1716. The inductance of each of the coils 1656, 1648 may be determined by the number, diameter and spacing of the windings 1704, 1712. The inductive or electromagnetic coupling between the coils 1648, 1656 is a function of their physical proximity, operating frequencies, coil sizes, and inductances. While the coils shown in FIGS. 17A and 17B have a generally circular shape, other shapes and structures may be used to implement the internal 1656 and external 1648 coils, depending on the implementation. For example, the coils 1648, 1656 may be shaped as a triangle, square, rectangle, pentagon, octagon, and so on. Generally, the coils 1648, 1656 may be shaped as polygons of any number of sides, which may be equal or unequal in length. The coils may be straight in certain portions and/or curved in certain portions. The coils 1648, 1656 may be arranged in a planar configuration. Alternatively, the coils 1648, 1656 may be arranged such that portions of the coils lie in different planes.

The coils 1648, 1656 together constitute a loosely coupled transformer, with the external coil 1648 acting as a primary winding and the internal coil 1656 acting as a secondary winding. The coils 1648, 1656 and the capacitors 1652, 1660 with which they may be connected may form a resonant circuit. The coils 1648, 1656 may be tuned to the same or different resonant frequencies. For example, the coils 1648, 1656 may be series tuned to a power transmission frequency of about 200 kHz. The external coil 1648 may induce an electric current in the internal coil 1656, which current generally behaves in accordance with the following equation:

$$\frac{V_1}{I_2} = \frac{V_2}{I_1} = \omega \cdot k \cdot \sqrt{L_1 \cdot L_2} \tag{1}$$

In Equation (1), $I_1$ is the current induced in the external resonant network 15. $I_2$ is the current induced in the internal coil network 17. $V_1$ is the voltage across the external resonant network 15. $V_2$ is the voltage across the internal resonant network 17. $\omega$ is the frequency of the voltage across the coils 1648, 1656, where the coil networks are tuned to the same frequency $\omega$. $L_1$ is the inductance of the external coil 1648. $L_2$ is the inductance of the internal coil 1656. k is the coupling coefficient.

The external assembly 1504 is located on the outside of the skin 1664 of the subject and includes the external coil network 15. The external assembly 1504 additionally includes the control and power source module 12, which is generally illustrated in FIG. 1. As shown in FIG. 5, the control and power source module 12 includes various components including the battery 24, the first processor 130, and the power inverter 148. These components each have a role in wireless power transfer system 11 and as such are again illustrated in FIGS. 15, 16 and 18. Other components of the control and power source module 12 portion of the external assembly 1504 are omitted from FIGS. 15, 16 and 18 for clarity.

Referring to both FIG. 15 and FIG. 16, the external assembly 1504 includes the power supply 24, which generally provides power in the form of a DC voltage. In some embodiments, the power supply 24 is a portable battery or battery pack providing a DC voltage of between 10 and 18 volts. The external assembly 1504 also includes the power inverter 148, which may be connected to the power junction 146 via a pair of conductive lines 1604, 1608. The power junction 146 supplies the DC power from a plurality of possible sources including batteries 24 or 80 or an external DC power supply to the power inverter 148, which converts the DC voltage into a high-frequency voltage. The high-frequency voltage is provided to the external resonant network 15 via a pair of conductors 1612, 1616. A current sensor 1620 may be used to sense the electric current flowing within the conductor 1616. The current sensor 1620 may be configured to sense either or both of the magnitude and phase of the electric current in the conductor 1616. The first processor 130 may be connected to the current sensor 1620 via a conductor 1624 and may be used to control the operation of the power bridge 148, based on one or more characteristics of the current sensed by the sensor 1620. The first processor 130 may also be configured to control the voltage $V_{in}$ that is provided by the power junction 146. The external coil network 15, which is disposed adjacent the skin 1664 of the subject, transfers electric power through the skin 1664 of the subject to the internal coil network 17 disposed beneath the skin 1664 of the subject.

The internal assembly 1508 is disposed beneath the skin 1664 of the subject and includes the internal coil network 17. The internal assembly 1508 additionally includes the internal controller module 21, which is generally illustrated in FIG. 1. As mentioned, the internal controller module 21 is generally configured to manage a power transfer that occurs across the external 15 and internal 17 resonant networks and to provide power to the implanted pump 14. The internal controller module 21 includes various components such as a power circuit and a rectifier that are illustrated in greater detail in FIGS. 15 and 16. Thus, as shown in FIG. 15, the internal coil network 17 is connected to a power circuit 1532 via a pair of conductors 1628, 1632. The power circuit 1532 includes a rectifier 1652 that performs full wave rectification of the sinusoidal AC current induced in the internal coil 1656 by the external coil 1648.

In one embodiment, the rectifier 1652 includes four switching elements, which may be provided in the form of diodes or Schottky diodes. During a first half of the AC power cycle, a first pair of diodes provides a conductive path up from ground, through the internal coil 1656, and out to conductor line 1628. During a second half of the AC power cycle, a second pair of diodes provides a conductive path up from ground, through the internal coil 1656, and out to conductor line 1628. In this way, the rectifier 1652 converts AC power provided by the internal coil network 17 into DC power that can be used by various components of the internal assembly 1508.

The power circuit 1532 additionally includes a regulator 1556 that regulates power supplied by the rectifier 1652. The regulator 1556 supplies electric power to a controller 1536 and other elements via a pair of conductors 1640, 1644. The controller 1536 may control the operation of the heart pump 14. The power conductors 1640, 1644 also supply electric power to a motor inverter that supplies power to the heart pump 14 through the controller 1536. The regulator 1556 may be a shunt type regulator that repeatedly charges and discharges a power supply capacitor. In other implementations, other types of regulators, such as a series regulator, may be used. In one embodiment, the power supply capacitor is a component of the charging circuit 1544. The voltage across the power capacitor is output via the lines 1640, 1644 to the controller 1536 and may be inverted to supply power to the implanted medical device such as heart pump 14.

During operation, the motor controller 1536 drives the heart pump 14 to pump blood through the artificial heart assembly, drawing electric current from the power supply capacitor associated with the charging circuit 1544. As current is drawn from the capacitor, the voltage across the capacitor decreases. To replenish the voltage on the capacitor, the power circuit 1532 periodically operates in a power supply mode in which electric current generated by the rectifier 1652 is provided to the capacitor via the lines 1640, 1644. When not operating in the power supply mode, the power circuit 1532 operates in an idle mode in which current is not supplied to the capacitor.

In the case of shunt type regulator 1556 shorting of the resonant secondary 17 may be accomplished by one or more shorting switches 1672 that operate to shift the power circuit 1532 between the power supply mode and the idle mode. In the power supply mode, the shorting switches 1672 open to allow current to flow from the internal resonant network 17, through the rectifier 1652, and out to the conductor line 1640/1644. In idle mode, the shorting switches 1672 close to short internal resonant network 17 so that current flows only within resonant network 228 rather than out to the conductor lines 1640/1644.

The magnitude of the output voltage across the power supply capacitor associated with regulator circuit 1556 may control whether the shorting switches 1672 are open or closed and thus whether the power circuit 1532 operates in the power supply mode or in the idle mode. For example, if the output voltage falls below a certain value, the shorting switches 1672 open and the power circuit 1532 operates in the power supply mode. When the output voltage rises to a certain value, the shorting switches 1672 close and the power supply circuit 1532 operates in the idle mode. By selectively supplying current to the power supply capacitor only during certain times (i.e. the power supply mode), the voltage across the capacitor is regulated, or maintained within a predetermined voltage range, such as between about 13 and about 14 volts, for example.

In one embodiment, the shorting switches 1672 are implemented as a pair of switching transistors, such as field-effect transistors, though any suitable structure may be used. For example, the shorting switches 1672 may be implemented using bipolar junction transistors, and so on. The switching transistors may be configured to short diodes associated with the rectifier 1652 in a conductive state and to not do so in a non-conductive state. A switching control circuit may control the conductive state of the switching transistors based on the output voltage across the power supply capacitor associated with the regulator circuit 1556. When the output voltage is above a certain value, the control circuit turns on the switching transistors to short diodes associated with the rectifier 1652. Here, current flows through the internal resonant network 17 and through the conductive transistors. When the output voltage is below a certain value, the control circuit turns off the switching transistors so that the diodes associated with the rectifier 1652 are not shorted. Here, current is allowed to flow from the internal resonant network 17, through the rectifier 1652, and out to the conductor line 1640/1644.

The external assembly 1504 may be responsive to the internal assembly shifting between the power supply mode and the idle mode. As mentioned above, the external assembly includes a first processor 130 that may be used to control the operation of the power inverter 148 based on one or more characteristics of the current sensed by the sensor 1620. In this regard, the power first processor 130 may change the frequency at which the power inverter 148 operates to conserve electric power during the idle mode. During the idle mode, when electric current is not being supplied to the capacitor associated with the charging circuit 1544, the power transmitted to the internal coil 1656 by the external coil 1648 is reduced in order to conserve power. This is accomplished by changing the frequency at which the power inverter 148 operates.

As noted above, the internal and external coils 1648, 1656 may be tuned to a power transmission frequency, such as about 200 kHz. Consequently, when it is desired to transmit power to the internal coil 1656, the power inverter 148 is operated at the power transmission frequency to which it is tuned. However, when it is not necessary to transmit a significant amount of power, such as during the idle mode above, the frequency of the power inverter 148 is changed. The frequency at which the power inverter 148 operates during the power-supply mode may be changed to an odd sub-harmonic of that frequency during the idle mode. For example, the idle mode frequency may be $\frac{1}{3}$, $\frac{1}{5}$, $\frac{1}{7}$, $\frac{1}{9}$ of the power supply mode frequency. The amount of power transmitted to the internal coil 1656 varies with the idle mode frequency, with less power being transmitted at the seventh subharmonic (i.e. $\frac{1}{7}$ of the power supply mode frequency, or 28.6 kHz if the power transmission frequency is 200 kHz) than at the third subharmonic (i.e. $\frac{1}{3}$ of the power supply mode frequency). Since odd subharmonics of a fundamental frequency still contain, in accordance with Fourier analysis, some components of the fundamental frequency, using an odd subharmonic of the power supply mode frequency during idle mode will still result in some power being transmitted to the internal coil 1656, which is generally desirable.

Figure 18:
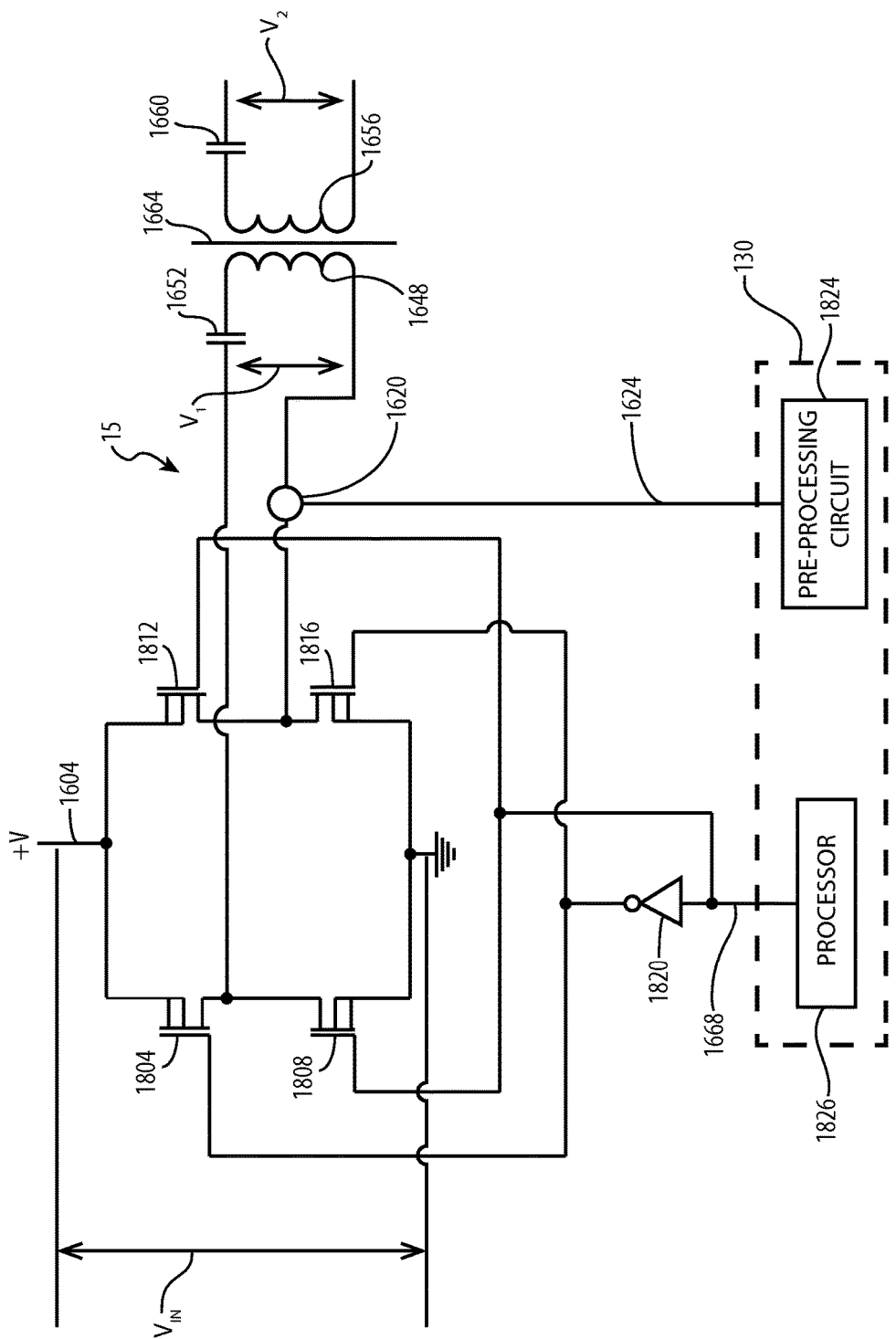
FIG. 18 is a circuit diagram that shows one implementation of the inverter shown in FIG. 15.

FIG. 18 is a circuit diagram that shows one implementation of the power inverter 148. As shown in FIG. 18, the power inverter 148 may comprise four transistors 1804, 1808, 1812, 1816, which may be metal oxide field-effect transistors (MOSFETs), connected in an H-bridge configuration. The four transistors 1804, 1808, 1812, 1816 may drive the external coil network 15 through the conductor 1612. Each of the transistors 1804, 1808, 1812, 1816, may be controlled by a respective high-frequency drive signal provided on the conductor 1668, with two of the drive signals being 180° out of phase, or complemented, with respect to the other two via an inverter 1820. The drive signals may be 50% duty cycle square waves provided at a frequency of about 200 kHz, for example. Although a particular type of DC-to-AC converter has been described above, any type of electronic switching network that generates a high-frequency voltage may be used. For example, as an alternative to the H-bridge configuration, the power inverter 148 may have transistors arranged in a voltage source half bridge configuration or in a current source configuration or in a class-DE amplifier voltage source configuration.

The power inverter 148 may be connected to the first processor 130 to control the operation of the power inverter 148 based on one or more characteristics of the current sensed by the sensor 1620. Referring to FIG. 16, the power inverter 148 may be connected to the first processor 130 through the conductor 1668. The first processor 130, in turn, may be connected to the current sensor 1620 via the line 1624. Referring to FIG. 18, first processor 130 may include certain pre-processing circuits 1824 that operate on the current signal and a processor 1826 that receives input generated by the pre-processing circuit 1824 based on the current signal. The pre-processing circuits 1824 may include circuits that accomplish such functions as current to voltage conversion, decoupling detection, interference detection, and shorting/un-shorting detection, and so on.

In one embodiment, the pre-processing circuit 1824 may be configured to generate a voltage that is indicative of the magnitude of the electric current flowing through the external coil 1648, where the current flowing through the external coil 1648 is proportional to the voltage across the internal coil 1656. During the idle mode, the shorting switches 1672 are closed, which causes the voltage across the internal coil network 17 to significantly decrease. That voltage decrease causes the current in the external coil 1648 to be significantly decreased, in accordance with Equation (1). Consequently, the voltage generated by the pre-processing circuit 1824 decreases significantly when the power circuit 1532 is in the idle mode.

The output of the first processor 130 may be configured to drive the power inverter 148 at different frequencies depending on the voltage received from the pre-processing circuit 1824. In one embodiment, the power management module 140 output may be provided by the processor 1826, which provides output responsive to input from the pre-processing circuit 1824. When the pre-processing circuit 1824 generates a voltage that is not decreased indicating that the power circuit 1532 is in power supply mode, the output of first processor 130 may drive the power inverter 148 at a first frequency, such as 200 kHz. When the pre-processing circuit 1824 generates a voltage that is decreased indicating that the power circuit 1532 is in idle mode, the output of the first processor 130 may drive the power bridge 148 at a second frequency that is an odd sub-harmonic of the frequency generated during the power supply mode.

System Monitoring

Embodiments discussed herein are directed to measuring and calculating various parameters associated with power transfer in the TETS system 11. The system 11 may be configured to derive various parameters based on current and/or voltages measurements made on the primary side. In accordance with various embodiments, current and/or voltages measurements made on the primary side may be used to calculate or estimate the coupling coefficient between the primary and the secondary, heat flux or temperature in the secondary, and heat flux or temperature in the primary. Primary side current and/or voltage measurements may also be used to determine if an external interference is present between the primary and the secondary. As described in greater detail below, the system 11 may use these calculations, estimations, and determinations to support control operations and/or to provide user alerts.

Coupling Calculations

Turing first to calculating the amount of coupling between the primary and secondary, reference is made to FIG. 16. In accordance with various embodiments, the system 11 may be configured to calculate the amount of coupling that exists between the external coil 1648 and the internal coil 1656. In Equation (1), the amount of coupling between the coils 1648, 1656 is represented by the coefficient k, which ranges from 0.0 to 1.0. Greater values for the coupling coefficient k indicate greater amounts of coupling between the coils 1648, 1656.

The coupling coefficient k is typically a function of the amount of separation between the coils 1648, 1656. This aspect of the coupling coefficient k can be illustrated with reference to FIG. 17A and FIG. 17B. In FIG. 17A, the external coil 1648 is placed against the subject's skin 1664, in close proximity to the implanted internal coil 1656. In FIG. 17B, the external coil 1648 is removed by a certain distance from the subject's skin 1660 and thus from the implanted internal coil 1656. This difference in the amount of separation between the coils 1648, 1656 in FIG. 17A and the coils 1648, 1656 in FIG. 17B will typically in result in these two coil placements having a different amount of coupling and thus different values for the coefficient k.

Over a certain range of coil separation distances, smaller distances between the coils 1648, 1656 correspond to greater amounts of coupling and thus k values that are closer to 1.0. Similarly, within this same range of coil separation distances, larger distances between the coils 1648, 1656 correspond to lesser amounts of coupling and thus k values that are closer to 0. Assuming that the coil placements shown in FIG. 17A and FIG. 17B fall within this range separation distances, the coil placement of FIG. 17A has a greater amount of coupling and thus a higher k value in comparison to the coil placement of FIG. 17B.

The system 11 may calculate the amount of coupling that exists between the external coil 1648 and the internal coil 1656 based on regulation timing parameters associated with the operation of the power circuit 1532. Regulation timing parameters used in coupling calculations include the power mode duty cycle $DC_{on}$ and the duration of the idle mode period $T_{off}$. $DC_{on}$ is the duration of the power mode $T_{on}$ over the duration of the regulation period $T_{reg}$, where the regulation period $T_{reg}$ equals the power mode period $T_{on}$ plus idle mode period $T_{off}$. As described in detail in connection with FIG. 19, one or more of these regulation timing parameters may be observable through measurements made on the primary side of the system 11. For a circuit having the series-series topology shown in FIG. 15, embodiments discussed herein make use of the following equation when estimating the amount of coupling between the external coil 1648 and the internal coil 1656:

$$k = \alpha \cdot T_{off} \cdot DC_{on} + \beta \cdot DC_{on} - \gamma \qquad (2)$$

For each unique design of coils there are a set of values for $\alpha$, $\beta$, and $\gamma$ that satisfy Equation (2), where K is the coupling coefficient between the external coil 1648 and the internal coil 1656. In operation, the system 11 can use Equation (2) to estimate the amount of coupling that exists between the external coil 1648 and the internal coil 1656 at any given time. Here, the system 11 can be programmed with values for $\alpha$, $\beta$, and $\gamma$ that correspond to the particular coil design being used. The regulation timing parameters $DC_{on}$ and $T_{off}$ can be derived from current or voltage measurement made on the primary side as power is transferred between the external assembly 1504 and the internal assembly 1508. In some implementations, the system 11 derives the regulation timing parameters from a current signal such as generated by the current sensor 1620, which measures the current present in the external coil 1648. The system 11 can also derive the regulation timing parameters from voltage signals generated by voltage sensors disposed a various locations on the primary side. For example, system 11 may derive the regulation timing parameters from voltage signals generated by voltage sensors arranged across either the coil 1648 or the capacitor 1652 of the external network 15.

Figure 19:
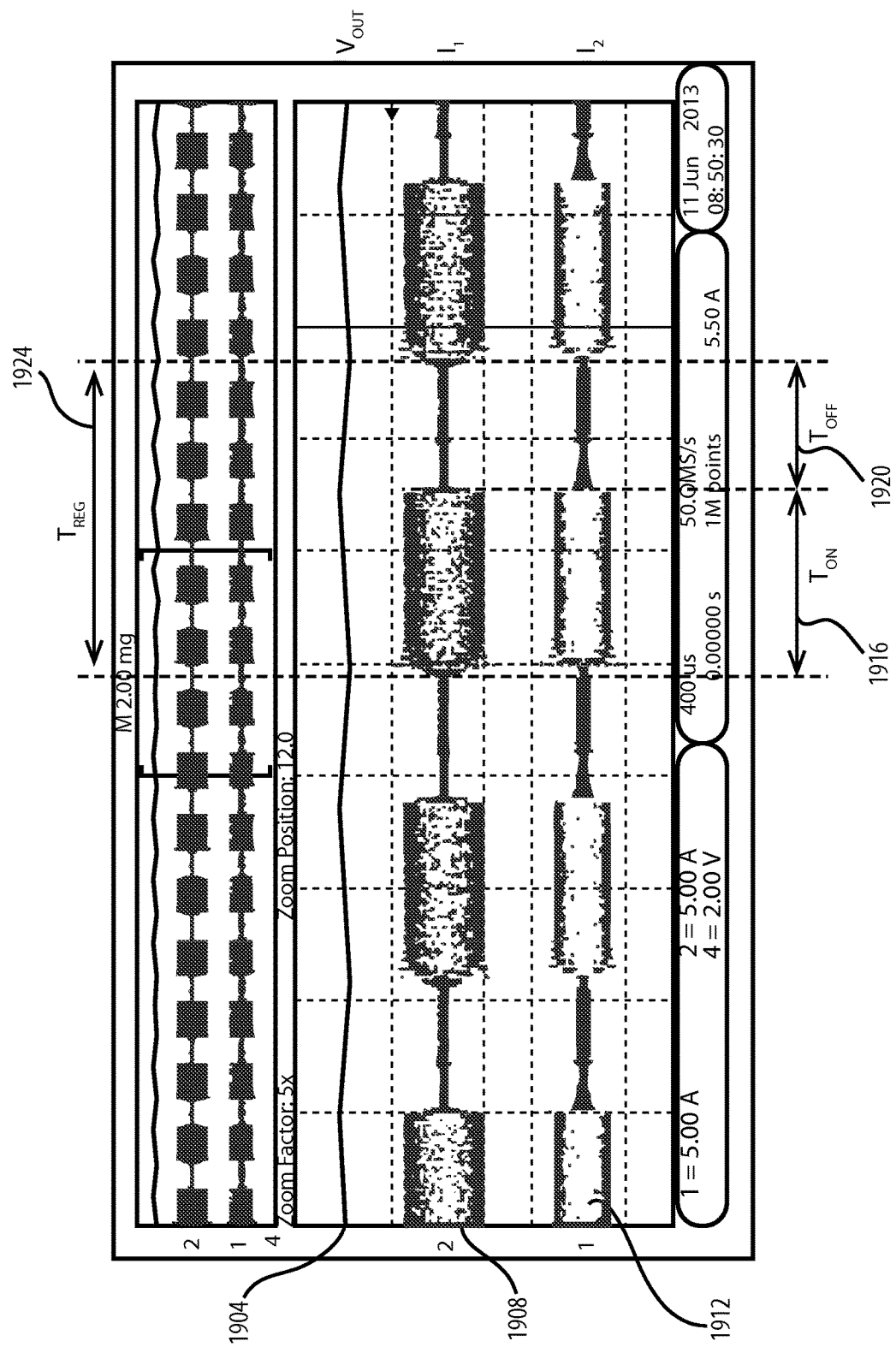
FIG. 19 is an illustration of waveform traces for signals that are present in the system of FIG. 15 as power is transferred between the external assembly and the internal assembly.
Figure 20:
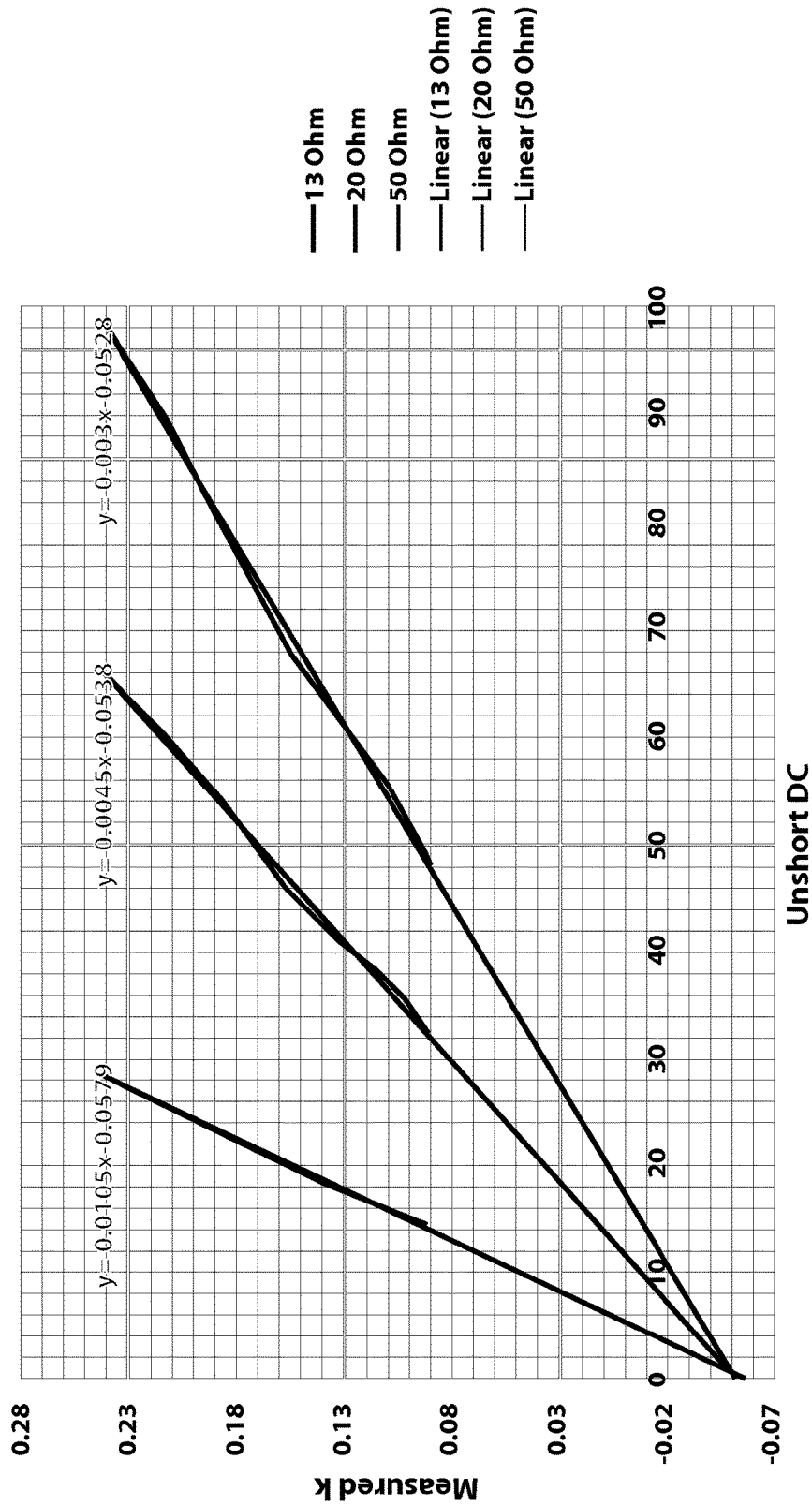
FIG. 20 is a collection of coupling coefficient data sets for the system shown in FIG. 15.

Referring to FIG. 19, aspects of system 11 that relate to deriving regulation timing parameters from primary side measurements are described in greater detail. FIG. 19 is an illustration of various waveform traces that represent signals that are present in the system 11 as power is transferred between the external assembly 1504 and the internal assembly 1508. FIG. 19 illustrates the magnitude of the voltage across the power supply capacitor associated with the regulator circuit 1544 as this signal changes over time. This voltage is labeled as $V_{OUT}$ and is referred to with reference number 1904. As can be seen in FIG. 19, $V_{OUT}$ gradually decreases as current is drawn from the capacitor associated with the regulator circuit 1544, and gradually increases when current is supplied to the capacitor from the rectifier 1652. The gradual decrease of $V_{OUT}$ corresponds to the power circuit 1532 being in the idle mode. Similarly, the gradual increase of $V_{OUT}$ corresponds to the power circuit 1532 being in the power supply mode.

FIG. 19 additionally illustrates a current signal that represents current present in the external coil 1648 as power is transferred between the external assembly 1504 and the internal assembly 1508. This current signal is labeled as and is referred to with reference number 1908. The current signal $I_1$ can be generated by the current sensor 1620 and is an example of a primary side signal that the system 11 may use to derive regulation timing parameters. FIG. 19 also illustrates a current signal that represents current present in the internal coil 1656 as power is transferred between the external assembly 1504 and the internal assembly 1508. This current signal is labeled as $I_2$ and is referred to with reference number 1912. As can be seen in FIG. 19, the amplitudes of both and $I_2$ are smaller when the power circuit 1532 is in the idle mode as compared to when the power circuit 1532 is in the power supply mode. $I_1$ is lower because $V_2$ drops to approximately zero in response to the shorting switches 1672 closing so as to short the internal resonant network 17. $I_2$ is lower because $V_1$ drops to a fraction of its power mode value in response to the power bridge 148 operating at a sub-harmonic frequency.

$T_{off}$ is defined as the duration of the short period and thus corresponds to the length of time that the shorting switches 1672 are closed so as to short the internal coil network 17. Stated another way, $T_{off}$ corresponds to the length of time that the power circuit 1532 is in the idle mode. $T_{off}$ can be derived from measurements of the current that is present in the external coil 1648 as power is transferred between the external assembly 1504 and the internal assembly 1508. Specifically, as can be seen in FIG. 19, $T_{off}$ can be measured by calculating the time that elapses between when transitions to a low amplitude and when transitions back to the high amplitude. Alternatively, $T_{off}$ can be calculated by subtracting the power mode period $T_{on}$ from the regulation period $T_{reg}$. An example time frame for a $T_{off}$ measurement is given in FIG. 19 and is generally identified with reference number 1916.

$T_{on}$ is defined as the duration of the un-shorted period and thus corresponds to length of time that the shorting switches 1672 are open so as to allow current to flow from the internal resonant network 17, through the rectifier 1652, and out to the conductor line 1640/1644. Stated another way, $T_{on}$ corresponds to the length of time that the power circuit 1532 is in the power supply mode. $T_{on}$ can be derived from measurements of the current that is present in the external coil 1648 as power is transferred between the external assembly 1504 and the internal assembly 1508. Specifically, as can be seen in FIG. 19, $T_{on}$ can be measured by calculating the time that elapses between when $I_1$ transitions to a high amplitude and when $I_1$ transitions back to the low amplitude. Alternatively, $T_{on}$ can be calculated by subtracting the idle mode period $T_{off}$ from the regulation period $T_{reg}$. An example time frame for a $T_{on}$ measurement is given in FIG. 19 and is generally identified with reference number 1920.

$T_{reg}$ is defined as the duration of the regulation period and thus corresponds to the length of time that the shorting switches are 1672 are open, plus the length of time that the shorting switches 1672 are closed. Stated another way, $T_{reg}$ corresponds to the length of time that the power circuit 1532 is in idle mode, plus the length of time that the power circuit is in power supply mode. $T_{reg}$ can be derived from measurements of the current that is present in the in the external coil 1648 as power is transferred between the external assembly 1504 and the internal assembly 1508. As can be seen in FIG. 19, $T_{reg}$ can be measured by calculating the time that elapses between when $I_1$ transitions to a high amplitude a first time and when $I_1$ transitions back to a high amplitude a second subsequent time. Alternatively, $T_{reg}$ can be calculated by adding the power mode period $T_{on}$ and the idle mode period $T_{off}$ together. An example time frame for a $T_{reg}$ measurement is given in FIG. 19 and is generally identified with reference number 1924.

$DC_{on}$ is the power mode duty cycle. $DC_{on}$ is defined as the duration of the power mode $T_{on}$ over the duration of the regulation period $T_{reg}$. Typically, current or voltage measurements are not taken that yield $DC_{on}$ directly. Rather, $DC_{on}$ is derived from other parameters, which themselves are derived from current measurements. Specifically, $DC_{on}$ can be derived by dividing the power mode period $T_{on}$ by the regulation period $T_{reg}$.

Because there are a set of values for $\alpha$, $\beta$, and $\gamma$ that satisfy Equation (2) for each unique design of coils, Equation (2) can be used to estimate the coupling coefficient k as power as is transferred between the external assembly 1504 and the internal assembly 1508. Specifically, in a particular implementation, the system 11 can be programmed with the values for $\alpha$, $\beta$, and $\gamma$ that correspond to the coil design used in that particular implementation. As the system transfers power between the external assembly 1504 and the internal assembly 1508, the power mode duty cycle $DC_{on}$ and the idle mode period $T_{off}$ can be derived from primary side measurements. As illustrated in FIG. 19, $DC_{on}$ and $T_{off}$ can be derived from the current signal $I_1$, which is generated the current sensor 1620 and which represents current present in the external coil 1648. In other examples, the system 11 can derive the regulation timing parameters from voltage signals generated by voltage sensors disposed a various locations on the primary side, such as across either the coil 1648 capacitor 1652 of the external network 15. Once $DC_{on}$ and $T_{off}$ are derived, Equation (2) can be used to calculate a value for the coupling coefficient k.

The approach to calculating the coupling coefficient k that is embodied in Equation (2) was verified on collected data from functional TETS systems 1500. Equation (2) was applied to collected short and duty cycle data. Several of these data samples are plotted in FIG. 20. It should be appreciated that Equation (2) applies to the series-series topology illustrated in FIG. 15. In accordance with alternative embodiments, other equations akin to Equation (2) can be derived for alternative topologies such as series-parallel, parallel-series, parallel-parallel and so on.

The system 11 may use coupling coefficient calculations to support control operations and/or to provide user alerts. For example, coupling calculations may be used in tracking of coil placement, executing control operations that mitigate excess heat flux or temperature, and/or providing alerts regarding excess heat flux or temperature. These control operations and user alerts are described in greater detail below in connection with FIG. 22 through FIG. 30.

Heat Flux and Temperature Calculations

The system 11 may additionally be configured to estimate the amount of the heat flux and/or temperature levels as power is transferred from the external assembly 1504 to the internal assembly 1508. Higher levels of heat flux or temperature in the system 11 can lead to tissue damage or otherwise injure the subject with whom the system 11 is used. Excessive heat flux or temperature can occur in either the primary or the secondary. Thus, in order to ensure safety of the subject, the system 11 may monitor heat flux and/or temperature levels in the either or both of the primary or the secondary.

The system 11 may monitor heat flux and/or temperature by monitoring the amount of current that is flowing in various parts of the system 11. Higher current levels generate $I^2R$ losses, which generate heat. In one respect, excessive heat flux can be generated when coupling between the primary and the secondary is non-optimal. Here, non-optimal coupling can lead to high currents, which generate due excess heat due to parasitic resistances that may be present in the inductors 1648, 1656 or other components of the internal or external networks 15, 17. When higher current levels are present in the system 11, heat flux tends to increase and temperatures tend to rise in a predictable manner. Higher current levels can be present in either or both of the primary or the secondary. Thus, the system 11 may monitor heat flux and/or temperature by monitoring currents present in either the primary and/or secondary. In one embodiment, current levels in the system are monitored through various measurements taken on the primary side of the system 11.

For current levels in the primary, the system 11 may make direct measurements using meters or probes that are attached to components in the external resonant network 15. In one example, the system 11 may measure the primary side current using the current sensor 1620, which measures the current present in the external coil 1648. The system 11 may also calculate the primary side current from based on voltage signals generated by voltage sensors disposed a various locations on the primary side, such as across either the coil 1648 or the capacitor 1652 of the external network 15. For example, the system 11 may calculate the primary side current using a known inductance value for the coil 1648 and a measured value for the voltage across the coil 1648. Alternatively, the system 11 may calculate the primary side current using a known capacitance value for the capacitor 1652 and a measured value for the voltage across the capacitor 1652.

For current levels in the secondary, the system 11 may measure certain regulation timing parameters on the primary side and estimate secondary current levels based on these primary side measurements. More specifically, the system 11 may first estimate the amount of coupling between the primary and the secondary based on regulation timing parameter measurements. The system 11 may then use the estimated coupling measurements made on the primary to estimate current levels in the secondary. Thus, in one respect, the system 11 may calculate the amount of coupling that exists between the external coil 1648 and the internal coil 1656 as part of estimating heat flux or temperature levels in the internal assembly 1508. Lower amounts of coupling generate heat because poor coupling results in higher currents being generated in the coils 1648, 1656. For a circuit having the series-series topology shown in FIG. 15, the inverse relationship between coupling and current in the secondary can be appreciated by rewriting Equation (1) in terms of $I_2$:

$$I_2 = \frac{V_p}{k * w * L_{eq}} \quad (3)$$

The coupling coefficient k appears in the denominator of Equation (3). Thus, decreases in the value of the coupling coefficient k correspond to increases in the value of the current in secondary.

As can be seen from Equation (3), the coupling coefficient k is one parameter needed to calculate the current $I_2$ that is present in the secondary. Another parameter needed for this calculation is $V_1$, the voltage across the external resonant network 15. $V_1$ is proportional to power supply DC voltage $V_{in}$. Typically, the power supply voltage $V_{in}$ does not change. Thus, with the exception that $V_1$ scales with frequency when the system shifts to a different subharmonic, $V_1$ is static. Thus, $V_1$ can be derived from system settings and is typically known without any measurements. For full-bridge inverter, the relationship between $V_{in}$ and $V_1$ is governed by the following equations:

$$V_1 = 4 * V_{in}/\pi. \quad (4)$$

Once values for k and $V_1$, are determined, Equation (3) can be used to calculate the current $I_2$ that is present in the secondary. As described above, the current $I_1$ that is present in the primary can be determined through direct measurements using meters or probes associated with the primary. Once values for $I_1$ and $I_2$ are determined, heat flux in the primary and/or the secondary can be determined. Heat flux in the primary is based on the current $I_1$ in the primary coil, the known parasitic resistance of primary coil, and the surface area of primary coil. Heat flux in the secondary is based on the current $I_2$ in the secondary coil, the known parasitic resistance of secondary coil, and the surface area of the secondary coil. The heat flux in either the primary or the secondary can be determined with the following equation:

$$\text{Heat Flux} = (I_{rms}^2 * R)/\text{Coil Surface Area}. \quad (5)$$

The temperature of the coils 1648, 1656 can be estimated based on the amount of heat flux that is determined to be present in either the primary or the secondary. Generally, the correlation between temperature and heat flux depends on the environment in which either the primary or the secondary operates. Thus, the system 11 may be programmed with an equation, a look-up table, or other data structure that correlates heat flux amounts to temperature changes in the primary and/or the secondary. The system 11 may be programmed with different equations, look-up tables, or other data structures for the primary and the secondary because these system components each are located in different environments.

The primary is located outside of the subject and thus the temperature of the primary can be estimated based on heat flux calculations and the predictable behavior of the primary as it operates in the open air. In one respect, temperature changes can be estimated based on heat flux level estimations made over a certain time interval. Temperature increases can be correlated with sustained elevated heat flux levels. Similarly, temperature decreases can be correlated with lower heat flux levels that are maintained over time. The system 11 may be programmed with an equation, a look-up table, or other data structure that quantifies these correlations and that may be accessed when determinations of the temperature in primary are made.

Figure 21:
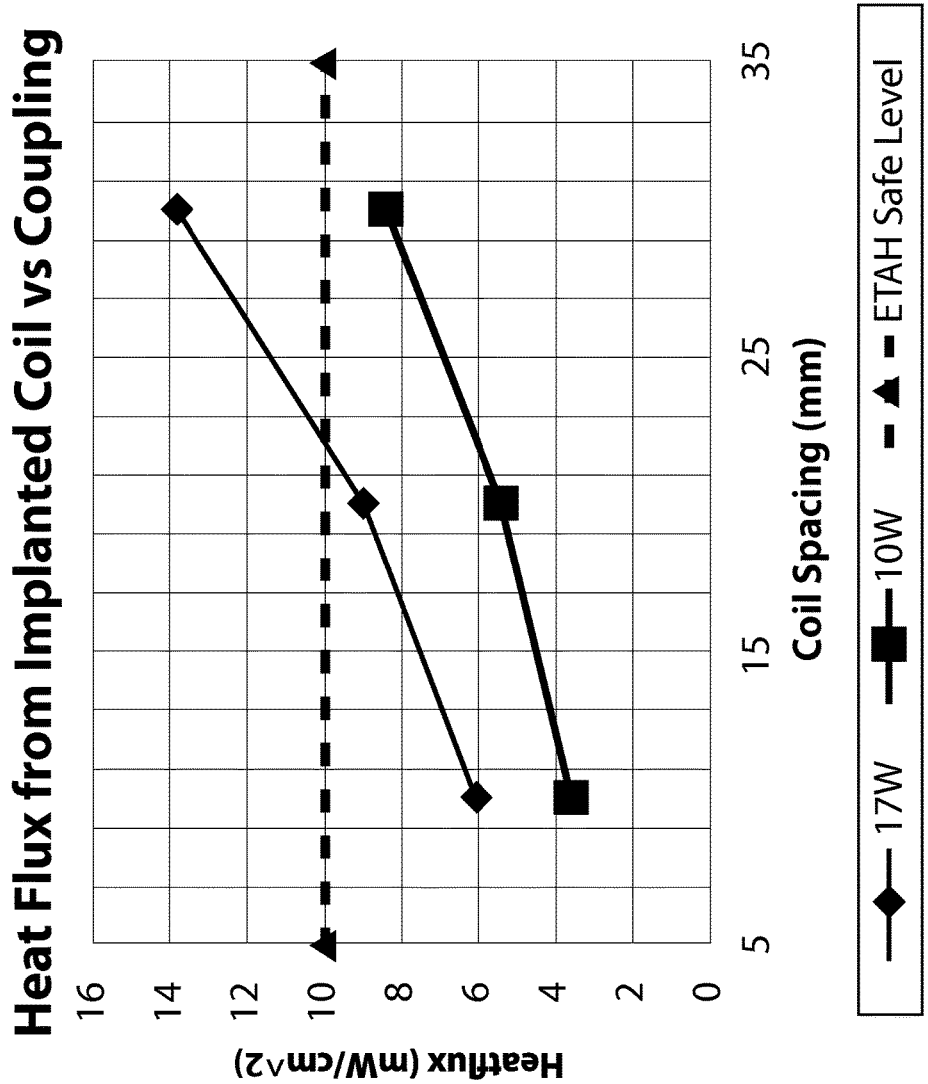
FIG. 21 is graphical illustration of safety level data acquired in an empirical study.

Depending on the location of the coil 1648 in the body there may be a specific relation between coil temperature and heat flux emanating from the coil 1648. For various current levels, animal studies can be used to estimate secondary heat flux amounts and safety levels. Results from one such animal study is shown in FIG. 21. Previous studies by Pennsylvania State University have found that 15 mW/cm$^2$ level is safe. The system 11 can be programmed based on the heat flux assessment shown in FIG. 21 or with other appropriate heat flux assessments. As was the case for the primary, temperature increases in the secondary can be correlated with sustained elevated heat flux levels; and temperature decreases can be correlated with lower heat flux levels that are maintained over time. The system 11 may be programmed with an equation, a look-up table, or other data structure that quantifies these correlations and heat assessments and that may be accessed when determinations of the temperature in secondary are made. The heat flux assessment of FIG. 21 is shown by way of example and limitation. It should be appreciated that the heat flux assessment shown in FIG. 21 can be adjusted based on future animal studies and that the heat flux to temperature correlations used by the system 11 can be based on animal studies which can be updated on an on-going basis.

Interference Calculations

The system 11 may additionally take measurements on the primary side so as to determine if any interference exists between the coils 1648, 1656. Interference can occur due to the presence of metal or a metallic object near one or both of the coils 1648, 1656. The presence of a metal or a metallic object can de-tune the coils 1648, 1656 by altering the amount and character of mutual inductance that exits between the coils 1648, 1656. The de-tuning can appear on the primary side as a phase shift between the voltage $V_1$ across the external resonant network 15 and the current $I_1$ through the external resonant network 15. Thus, the system 11 can determine if any interference exists between the coils 1648, 1656 by measuring this phase difference. Specifically, the system measures the voltage $V_1$ across the external resonant network 15 and the current $I_1$ through the external resonant network 15 over a predetermined time period using the techniques described above. These measurements are then compared to determine if any phase shift exists. If the system 11 detects a phase shift, the system 11 may determine that the coils 1648, 1656 have become detuned due to the presence of an interfering metal or metallic object.

The system 11 may take one or more corrective actions in response to determining that the coils 1648, 1656 have become detuned. In some cases, the system 11 may provide an alert that indicates to the user that an interfering metal or metallic object is present. The system 11 may then reject estimations made of the current $I_2$ in the secondary until the user removes the metal or metallic object. The system 11 may reject estimations made of the current $I_2$ because Equation (2) is based on the assumption that the voltage $V_1$ and the current are in phase. Specifically, Equation (2) is based on the assumption that resonant circuit operates at resonance and that there is specific relationship between the resonant circuit parameters, namely L1, C1, k, M, L2, C2. This relationship breaks down when metal is introduced. This, if the voltage $V_1$ and the current $I_1$ are out of phase, Equation (2) may cease to accurately characterize the behavior of the system 11. In other cases, the system 11 may compensate for the phase difference between the voltage $V_1$ and the current rather than wait for the user to remove the interfering metal or metallic object. Specifically, the system 11 may alter the manner in which the power bridge 148 operates. In one embodiment, the power management module 140 can change control frequency of the power bridge 148 to compensate for a shift in resonance that occurs due to the fact that metal objects change mutual and leakage inductance of the coil and as result change resonance point of the system.

Controller Operations

In accordance with present embodiments, first processor 130 may function to measure and calculate various parameters associated with power transfer in the TETS system 11. First processor 130 may then use these parameters to initiate control operations and/or provide alerts. For example, first processor 130 may initiate control operations and/or provide alerts responsive to potential decoupling between the coils 1648, 1656, estimated elevated heat flux levels in the primary or secondary, and/or estimated elevated temperature levels in the primary or secondary.

Figure 22:
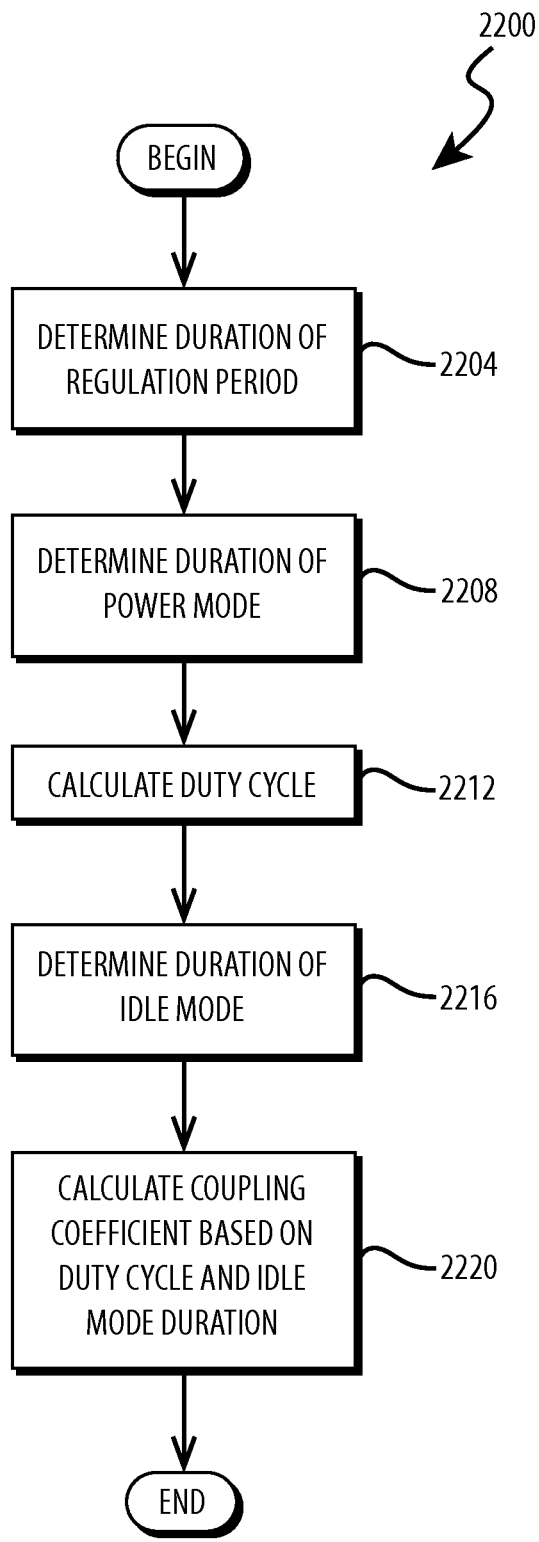
FIG. 22 is a flow chart that illustrates a method of calculating a coupling coefficient in accordance with embodiments discussed herein.

Turning first to first processor 130 operations that function to calculate a coupling coefficient k, reference is made to FIG. 22. FIG. 22 is a flow chart 2200 that illustrates a method of calculating a coupling coefficient k in accordance with embodiments discussed herein. The method illustrated by the flow chart 2200 includes operations executed by first processor 130 shown in FIG. 15. First processor 130 is external to the subject and so may be configured to receive input signals from various points on the primary side of the system 11. As set forth in flow chart 2200, the power management module 140 may calculate the coupling coefficient k between the external coil 1648 and the internal coil 1656 by performing various calculations based on the primary side input signals.

Initially, in operation 2200, the system 11 determines the duration of the regulation period $T_{reg}$. The regulation period $T_{reg}$ corresponds to the duration of the power supply period $T_{on}$, plus the duration of the idle period $T_{off}$. An example regulation period $T_{reg}$ 1924 is illustrated in connection with the example waveform traces shown in FIG. 19. The system 11 may determine the duration of the regulation period $T_{reg}$ based on measurements of the current in the external resonant network 15 that are made as power is transferred from the external assembly 1504 to the internal assembly 1508. Specifically, the current sensor 1620 may generate an output signal corresponding to the magnitude of the current flowing through the external coil 1648, which signal is passed as input to the first processor 130. First processor 130 may then monitor the current signal to determine when the power circuit 1532 transitions between the power mode and the idle mode by determining when the current signal transitions between a low amplitude and high amplitude. First processor 130 may register a regulation period $T_{reg}$ as occurring between the time when the current signal transitions to a high amplitude a first time and the time when the current signal transitions back to a high amplitude a second subsequent time.

In operation 2208, the system 11 determines the duration of the power mode. An example power mode period $T_{on}$ 1920 is illustrated in connection with the example waveform traces shown in FIG. 19. The system 11 may determine the duration of the power mode period $T_{on}$ based on measurements of the current in the external resonant network 15 that are made as power is transferred from the external assembly 1504 to the internal assembly 1508. Specifically, the current sensor 1620 may generate an output signal corresponding to the magnitude of the current flowing through the external coil 1648, which signal is passed as input to the power management module 140. first processor 130 may then monitor the current signal to determine when the power circuit 1532 transitions between the power mode and the idle mode by determining when the current signal transitions between a low amplitude and high amplitude. First processor 130 may register a power mode period $T_{on}$ as occurring between the time when the current signal transitions to a high amplitude and the time when the current signal transitions to a low amplitude.

In operation 2212, the system 11 calculates the power mode duty cycle $DC_{on}$. $DC_{on}$ is defined as the duration of the power mode $T_{on}$ over the duration of the regulation period $T_{reg}$. First processor 130 may determine the power mode duty cycle $DC_{on}$ by dividing the power mode period $T_{on}$ obtained in operation 2208 by the regulation period $T_{reg}$ obtained in operation 2204.

In operation 2216, the system 11 determines the duration of the idle mode. An example idle mode period $T_{off}$ 1916 is illustrated in connection with the example waveform traces shown in FIG. 19. The system 11 may determine the duration of the idle mode period $T_{off}$ based on measurements of the current in the external resonant network 15 that are made as power is transferred from the external assembly 1504 to the internal assembly 1508. Specifically, the current sensor 1620 may generate an output signal corresponding to the magnitude of the current flowing through the external coil 1648, which signal is passed as input to the first processor 130. First processor 130 may then monitor the current signal to determine when the power circuit 1532 transitions between the power mode and the idle mode by determining when the current signal transitions between a low amplitude and high amplitude. First processor 130 may register an idle mode period $T_{off}$ as occurring between the time when the current signal transitions to a low amplitude and the time when the current signal transitions to a high amplitude.

In operation 2220, the system 11 calculates the coupling coefficient k between the external coil 1648 and the internal coil 1656. The system 11 may determine the coupling coefficient k using Equation (2). Here, the first processor 130 may be programmed with values for α, β, and γ that correspond to the particular coil design being used. In calculating the coupling coefficient k, the first processor 130 may these pre-programmed values, as well as the value for the power mode duty cycle $DC_{on}$ obtained in operation 2212 and the value for the idle mode period $T_{off}$ obtained in operation 2216. Specifically, the first processor 130 may enter these programmed and measured values into Equation (2) and in so doing obtain an estimation for the coupling coefficient k between the external coil 1648 and the internal coil 1656.

Figure 23:
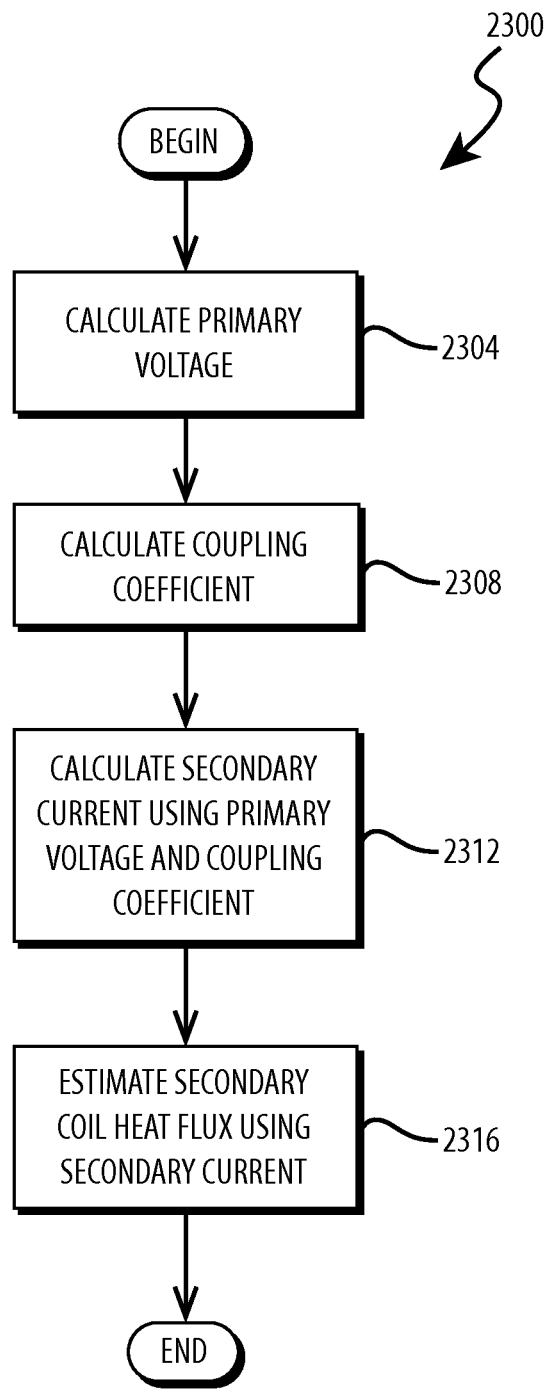
FIG. 23 is a flow chart that illustrates a method of estimating a secondary coil heat flux in accordance with embodiments discussed herein.

FIG. 23 is a flow chart 2300 that illustrates a method of estimating a secondary coil heat flux in accordance with embodiments discussed herein. The method illustrated by the flow chart 2300 includes operations executed by the power management module 140 shown in FIG. 15. The first processor 130 is external to the subject and so may be configured to receive input signals from various points on the primary side of the system 11. As set forth in flow chart 2300, the first processor 130 may calculate the secondary coil heat flux by performing various calculations based on the primary side input signals.

Initially, in operation 2304, the system 11 determines the voltage $V_1$ across the external resonant network 15. As mentioned, $V_1$ is proportional to the power supply DC voltage $V_{in}$, and thus does not typically change except for scaling when the system shifts to a different subharmonic. Thus, $V_1$ can be derived from system settings and is typically known without any measurements. In implementations that use a full-bridge inverter, first processor 130 can calculate $V_1$ using $V_{in}$ and Equation (4).

In operation 2308, the system 11 calculates the coupling coefficient k between the external coil 1648 and the internal coil 1656. As set forth in connection with FIG. 22, the system 11 may use Equation (2) to calculate the coupling coefficient k based on programmed values for α, β, and γ, and measured values for the power mode duty cycle $DC_{on}$ and the idle mode period $T_{off}$.

In operation 2312, the system 11 estimates the current $I_2$ present in the internal coil 1656 using the voltage $V_1$ across the external resonant network 15 and the coupling coefficient k between the external coil 1648 and the internal coil 1656. The system 11 may determine the current $I_2$ present in the internal coil 1656 using the value for the voltage $V_1$ obtained in operation 2304 and the value for the coupling coefficient k obtained in operation 2308. Specifically, the first processor 130 may enter these measured values into Equation (3) and in so doing obtain an estimation for the current $I_2$.

In operation 2316, the system 11 estimates secondary coil heat flux using current $I_2$. As mentioned, heat flux in the secondary is based on the current $I_2$ in the secondary coil, the known parasitic resistance of secondary coil, and the surface area of the secondary coil. Thus, the heat flux in the secondary can be calculated or otherwise estimated using the current $I_2$ present in the internal coil 1656 as determined in operation 2312. Here, the power management module 140 can calculate the heat flux in the secondary using Equation (5).

Figure 24:
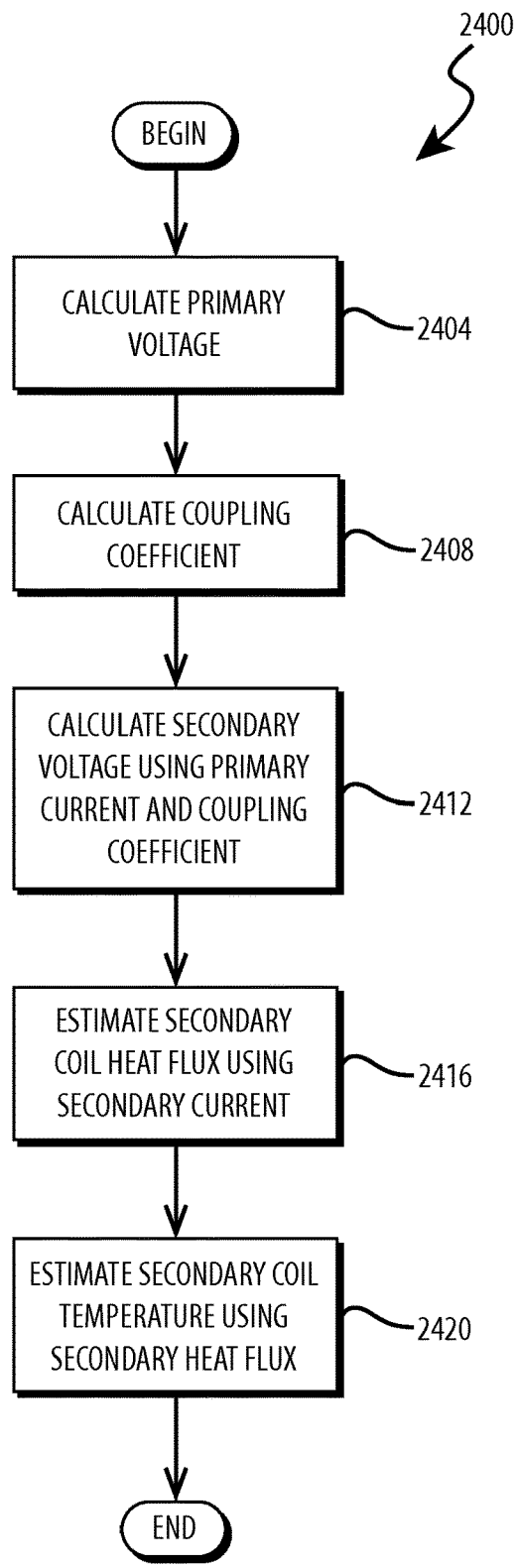
FIG. 24 is a flow chart that illustrates a method of estimating a secondary coil temperature in accordance with embodiments discussed herein.

FIG. 24 is a flow chart 2400 that illustrates a method of estimating a secondary coil temperature in accordance with embodiments discussed herein. The method illustrated by the flow chart 2400 includes operations executed by the first processor 130 shown in FIG. 15. The first processor 130 is external to the subject and so may be configured to receive input signals from various points on the primary side of the system 11. As set forth in flow chart 2400, the first processor 130 may calculate the secondary coil heat temperature by performing various calculations based on the primary side input signals.

Initially, in operation 2404, the system 11 determines the voltage $V_1$ across the external resonant network 15. As mentioned, $V_1$ is proportional to the power supply DC voltage $V_{in}$, and thus does not typically change except for scaling with frequency when the system shifts to a different subharmonic. Thus, $V_1$ can be derived from system settings and is typically known without any measurements. In implementations that use a full-bridge inverter, power management module 140 can calculate $V_1$ using $V_{in}$ and Equation (4).

In operation 2408, the system 11 calculates the coupling coefficient k between the external coil 1648 and the internal coil 1656. As set forth in connection with FIG. 22, the system 11 may use Equation (2) to calculate the coupling coefficient k based on programmed values for α, β, and γ, and measured values for the power mode duty cycle $DC_{on}$ and the idle mode period $T_{off}$.

In operation 2412, the system 11 estimates the current $I_2$ present in the internal coil 1656 using the voltage $V_1$ across the external resonant network 15 and the coupling coefficient k between the external coil 1648 and the internal coil 1656. The system 11 may determine the current $I_2$ present in the internal coil 1656 using the value for the voltage $V_1$ obtained in operation 2404 and the value for the coupling coefficient k obtained in operation 2408. Specifically, the first processor 130 may enter these measured values into Equation (3) and in so doing obtain an estimation for the current $I_2$.

In operation 2416, the system 11 estimates secondary coil heat flux using current $I_2$. As mentioned, heat flux in the secondary is based on the current $I_2$ in the secondary coil, the known parasitic resistance of secondary coil, and the surface area of the secondary coil. Thus, the heat flux in the secondary can be calculated or otherwise estimated using the current $I_2$ present in the internal coil 1656 as determined in operation 2412. Here, the first processor 130 can calculate the heat flux in the secondary using Equation (5).

In operation 2420, the system 11 estimates the secondary coil temperature using the secondary heat flux. In one implementation, the system 11 may estimate temperature changes based on heat flux levels estimations made over a certain time interval. Thus, the first processor 130 may measure and record a number of heat flux calculations as set forth in operation 2416 and make temperature estimations based on these heat flux calculations. The power management module 140 may correlate temperature increases with sustained elevated heat flux levels. Similarly, the first processor 130 may correlate temperature decreases with lower heat flux levels that are maintained over time. Heat flux to temperature correlations can be based on animal studies which can be updated on an on-going basis.

Figure 25:
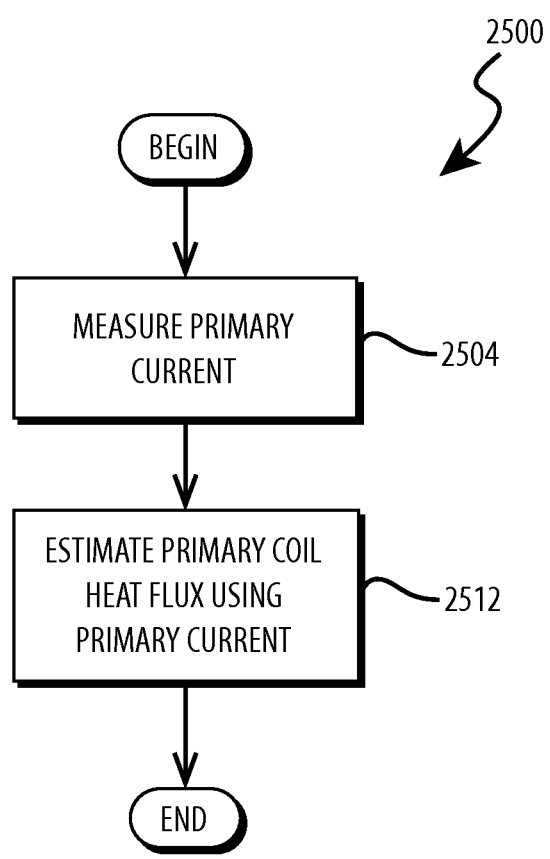
FIG. 25 is a flow chart that illustrates a method of estimating a primary coil heat flux in accordance with embodiments discussed herein.

FIG. 25 is a flow chart 2500 that illustrates a method of estimating a primary coil heat flux in accordance with embodiments discussed herein. The method illustrated by the flow chart 2500 includes operations executed by the power management module 140 shown in FIG. 15. The first processor 130 is external to the subject and so may be configured to receive input signals from various points on the primary side of the system 2900. As set forth in flow chart 2500, the first processor 130 may estimate the primary coil heat flux by performing various calculations based on the primary side input signals.

Initially, in operation 2504, the system 11 calculates the current that is present in the external coil 1648. An example primary current $I_1$ 1904 is illustrated in connection with the example waveform traces shown in FIG. 19. The system 11 may determine the current based on measurements made in the external resonant network 15 as power is transferred from the external assembly 1504 to the internal assembly 1508. Specifically, the current sensor 1620 may generate an output signal corresponding to the magnitude of the current flowing through the external coil 1648, which signal is passed as input to first processor 130. The first processor 130 may then sample this signal as needed to determine magnitude of the current that is present in the external coil 1648.

In operation 2512, the system 11 estimates the primary coil heat flux using the current $I_1$. As mentioned, heat flux in the primary is based on the current in the primary coil, the known parasitic resistance of primary coil, and the surface area of the primary coil. Thus, the heat flux in the primary can be calculated or otherwise estimated using the current present in the external coil 1648 as determined in operation 2504. Here, the first processor 130 can calculate the heat flux in the primary using Equation (5).

Figure 26:
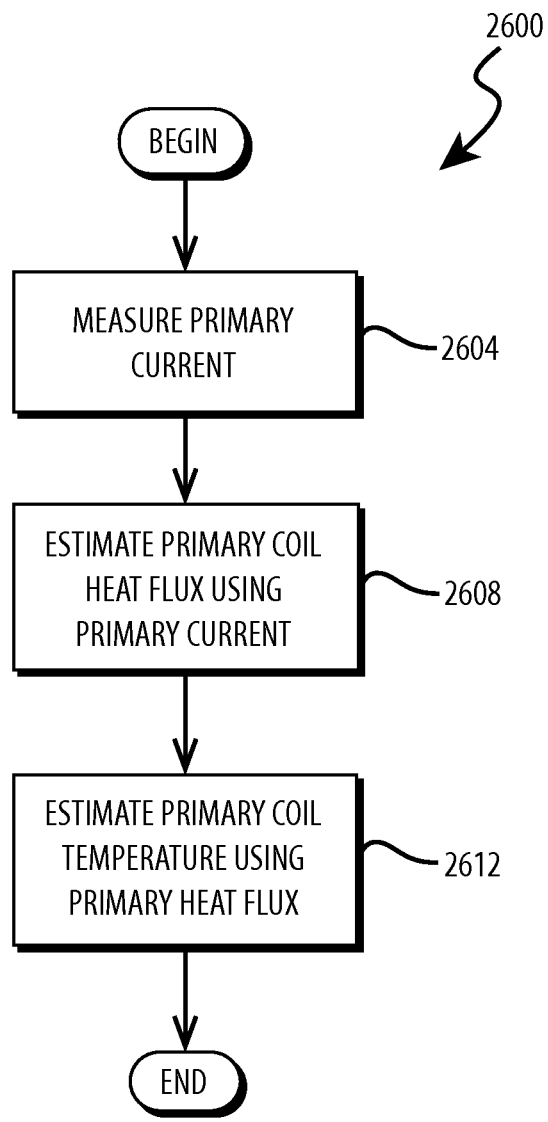
FIG. 26 is a flow chart that illustrates a method of estimating a primary coil heat temperature in accordance with embodiments discussed herein.

FIG. 26 is a flow chart 2600 that illustrates a method of estimating a primary coil temperature in accordance with embodiments discussed herein. The method illustrated by the flow chart 2600 includes operations executed by the power management module 140 shown in FIG. 15. first processor 130 is external to the subject and so may be configured to receive input signals from various points on the primary side of the system 11. As set forth in flow chart 2600, the first processor 130 may estimate the primary coil temperature by performing various calculations based on the primary side input signals.

Initially, in operation 2604, the system 11 calculates the current $I_1$ that is present in the external coil 1648. An example primary current $I_1$ 1904 is illustrated in connection with the example waveform traces shown in FIG. 19. The system 11 may determine the current $I_1$ based on measurements made in the external resonant network 15 as power is transferred from the external assembly 1504 to the internal assembly 1508. Specifically, the current sensor 1620 may generate an output signal corresponding to the magnitude of the current flowing through the external coil 1648, which signal is passed as input to the power management module 140. The first processor 130 may then sample this signal as needed to determine magnitude of the current that is present in the external coil 1648.

In operation 2612, the system 11 estimates primary coil heat flux using current $I_1$. As mentioned, heat flux in the primary is based on the current $I_1$ in the primary coil, the known parasitic resistance of the primary coil, and the surface area of the primary coil. Thus, the heat flux in the primary can be calculated or otherwise estimated using the current $I_1$ present in the external coil 1648 as determined in operation 2604. Here, the first processor 130 can calculate the heat flux in the primary using Equation (5).

In operation 2616, the system 11 estimates the primary coil temperature using the primary heat flux. In one implementation, the system 11 may estimate temperature changes based on heat flux levels estimations made over a certain time interval. Thus, the power management module 140 may measure and record a number of heat flux calculations as set forth in operation 2612 and make temperature estimations based on these heat flux calculations. The first processor 130 may correlate temperature increases with sustained elevated heat flux levels. Similarly, the first processor 130 may correlate temperature decreases with lower heat flux levels that are maintained over time.

Figure 27:
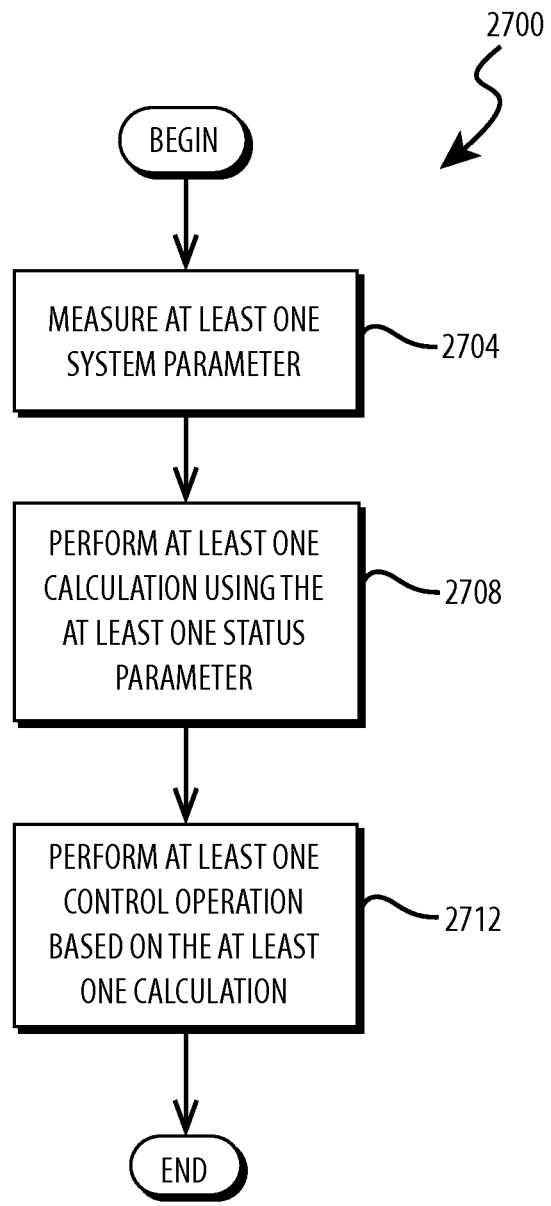
FIG. 27 is a flow chart that illustrates a method of performing at least one control operation in accordance with embodiments discussed herein.

FIG. 27 is a flow chart 2700 that illustrates a method of performing at least one control operation in accordance with embodiments discussed herein. The method illustrated by the flow chart 2700 includes operations executed by the power management module 140 shown in FIG. 15. The first processor 1300 is external to the subject and so may be configured to receive input signals from various points on the primary side of the system 11. Based on these input signals, the first processor 130 may initiate control operations on the primary side that affect the operation of the system 11 on either or both of the primary or secondary side.

Initially, in operation 2704, the system 11 measures at least one system parameter. Here, the first processor 130 may sample the current signal provided by the current sensor 1620 to measure voltage regulation timing parameters, such as the regulation period $T_{reg}$, the power mode duration $T_{on}$, the idle mode duration $T_{off}$, the power mode duty cycle $DC_{on}$, and so. The first processor 130 may also measure or otherwise determine other circuit parameters on the primary side such as the primary current, the primary voltage, the phase between primary current and primary voltage, the input voltage, and so on.

In operation 2708, the system 11 performs at least one calculation using the at least one status parameter measured in operation 2704. As set forth in connection with FIG. 22 through FIG. 26, the first processor 130 may calculate the coupling coefficient, secondary heat flux, secondary coil temperature, primary heat flux, primary coil temperature, and so on.

In operation 2712, the system 11 performs at least one control operation based on the at least one calculation performed in operation 2708. In one embodiment, the system 11 may execute a control operation to adjust or otherwise control power transferred based on the coupling coefficient k. Thus, in operation 2804, the power management module 140 measures the idle mode duration $T_{off}$ and the power mode duty cycle $DC_{on}$. In operation 2708, the first processor 130 calculates the coupling coefficient k as set forth in connection with FIG. 22. Finally, in operation 2712, the power management module 140 adjusts the power transferred from the primary to the secondary based on the coupling coefficient k calculated in operation 2708.

In some cases, the first processor 130 may adjust the power transferred by outputting a control signal that causes the power source to operate at a lower voltage V. Lowering the voltage $V_{in}$ output from the power source lowers the voltage $V_1$ across the internal resonant network. Lowering the voltage $V_1$ causes the current $I_2$ circulating in the internal resonant network 17 to decease per Equation (1). In other cases, the first processor 130 may lower the voltage $V_1$ and, as a consequence, the current $I_2$ circulating in the internal resonant network 17 by using phase shift control of the inverter, or using sub-harmonic frequencies. By lowering or otherwise adjusting the voltage $V_1$ to cause a lowering the current $I_2$ that circulates in the internal resonant network 17, the system 11 lowers the $I^2R$ losses that may occur as a result of the potential de-coupling detected in operation 2708.

The first processor 130 may also adjust the power transferred by switching to a different sub-harmonic. Here, first processor 130 may change the frequency at which the power bridge 148 operates so as to transmit power using a lower sub-harmonic. During this frequency shift, primary current remains same, but un-short $T_{on}$ period extends. This results in larger $I^2R$ losses in the primary. The result of this operation is heat transfer from secondary to primary in response to the potential de-coupling detected in operation 2708. Overall efficiency remains the same.

In another embodiment, the system 11 may execute a control operation to adjust or otherwise control secondary coil current $I_2$ to control secondary heat flux based on secondary coil heat flux calculations. Thus, in operation 2804, the first processor 130 measures the idle mode duration $T_{off}$ and the power mode duty cycle $DC_{on}$. Additionally, the first processor 130 may determine the primary voltage $V_1$ from system settings by which the primary voltage $V_1$ can be known or otherwise derived. In operation 2708, the controller calculates the secondary coil heat flux as set forth in connection with FIG. 23. Finally, in operation 2712, the power management module 140 adjusts the secondary coil current $I_2$ based on the secondary coil heat flux calculated in the operation 2708.

The system 11 may also execute a control operation to adjust or otherwise control secondary coil current $I_2$ to control secondary temperature based on secondary coil temperature calculation. Thus, in operation 2804, the power management module 140 measures the idle mode duration $T_{off}$, the power mode duty cycle $DC_{on}$, and the primary voltage $V_1$. In operation 2708, the controller calculates the secondary temperature as set forth in connection with FIG. 24. Finally, in operation 2712, the power management module 140 adjusts the secondary coil current $I_2$ based on the secondary temperature calculated in the operation 2708.

The system 11 may also execute a control operation to adjust or otherwise control primary coil current $I_1$ to control primary heat flux based on primary coil heat flux calculation. Thus, in operation 2804, the first processor 130 measures primary coil current $I_1$. In operation 2708, the controller calculates the primary heat flux as set forth in connection with FIG. 25. Finally, in operation 2712, the power management module 140 adjusts the primary coil current based on the primary heat flux calculated in the operation 2708.

The system 11 may also execute a control operation to adjust or otherwise control primary coil current $I_1$ to control primary temperature based on primary coil temperature calculation. Thus, in operation 2804, the first processor 130 measures primary coil current $I_1$. In operation 2708, the controller calculates the primary coil temperature as set forth in connection with FIG. 26. Finally, in operation 2712, the first processor 130 adjusts the primary coil current based on the primary coil temperature calculated in the operation 2708.

In connection with the various control operations discussed above, excess temperature can be reduced on primary side. Per Equation (1) if secondary voltage $V_2$ is reduced, the primary current $I_1$ will go down as well. Secondary voltage $V_2$ can be reduced by reducing input power beyond required power by the secondary. Reducing primary current reduces $I^2R$ losses in the primary, but does not affect the duration of un-short period $T_{on}$ of secondary coil 1656. Thus, secondary losses remain the same, and efficiency improves.

Figure 28:
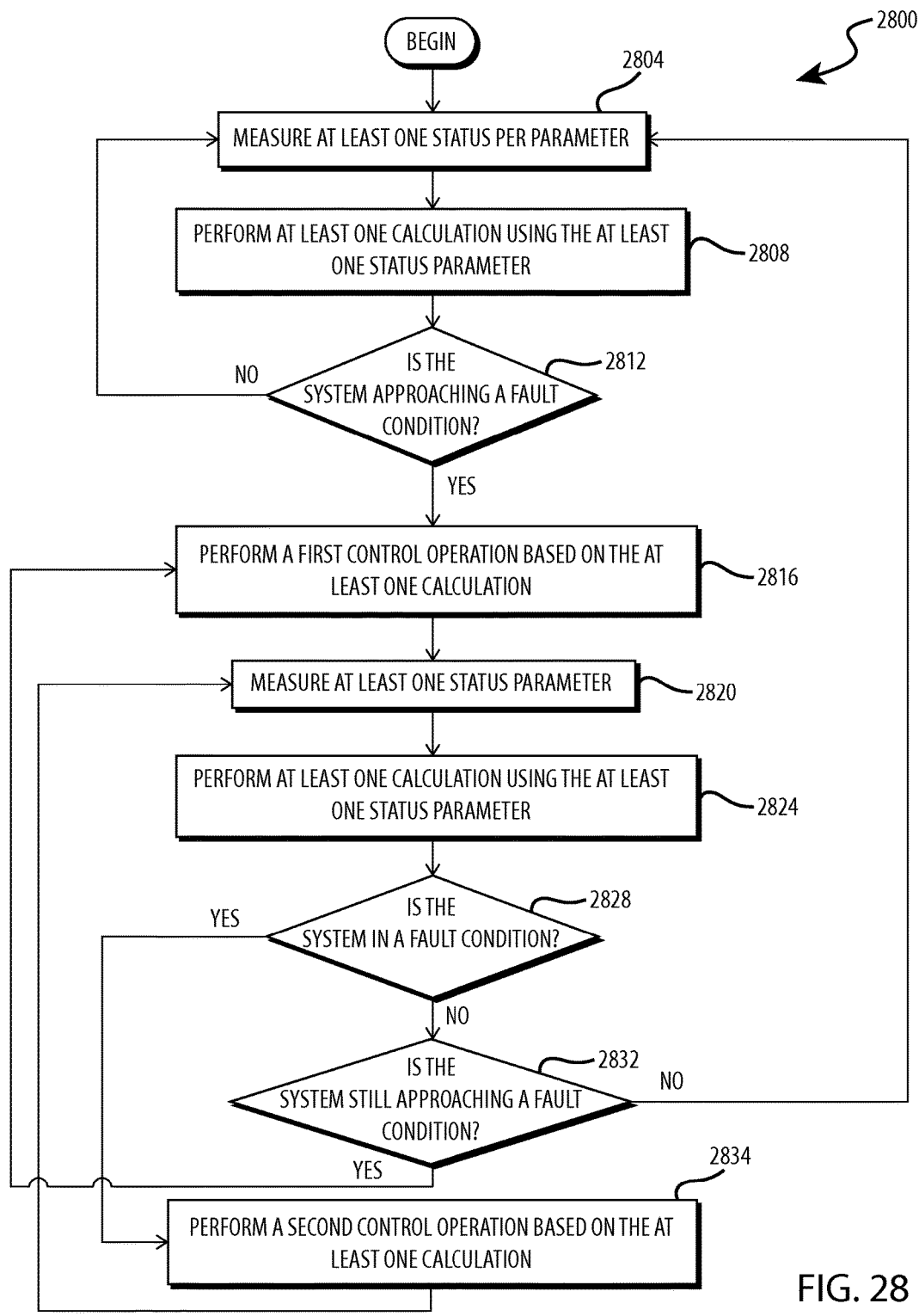
FIG. 28 is a flow chart that illustrates a method of performing control operations in accordance with embodiments discussed herein.

FIG. 28 is a flow chart 2800 that illustrates a method of performing at least two control operations in accordance with embodiments discussed herein. The method illustrated by the flow chart 2800 includes operations executed by the power management module 140 shown in FIG. 15. The first processor 130 is external to the subject and so may be configured to receive input signals from various points on the primary side of the system 11. Based on these input signals, the first processor 130 may execute operations on the primary side that affect the operation of the system 11 on either or both of the primary or secondary side.

Initially, in operation 2804, the system 11 measures at least one system parameter. Here, the first processor 130 may sample the current signal provided by the current sensor 1620 to measure voltage regulation timing parameters, such as the regulation period $T_{reg}$, the power mode duration $T_{on}$, the idle mode duration $T_{off}$, the power mode duty cycle $DC_{on}$, and so. The first processor 130 may also measure or otherwise determine other circuit parameters on the primary side such as the primary current, the primary voltage, the phase between primary current and primary voltage, the input voltage, and so on.

In operation 2808, the system 11 performs at least one calculation using the at least one status parameter measured in operation 2804. As set forth in connection with FIG. 22 through FIG. 26, the first processor 130 may calculate the coupling coefficient, secondary heat flux, secondary coil temperature, primary heat flux, primary coil temperature, and so on.

In operation 2812, the first processor 130 determines if the system 11 is approaching a fault condition. The fault condition may be a de-coupling of the coils, excess heat flux, excess temperature, insufficient available power, and so on. If the first processor 130 determines that the system 11 is not approaching a fault condition, operation 2804 may again be executed following operation 2812. If the determines that the system 11 is approaching a fault condition, operation 2816 may be executed following operation 2812.

In operation 2816, the first processor 130 performs a first control operation based on the at least one calculation performed in operation 2808. Here, the first processor 130 may execute a control operation to adjust the power transferred from the primary to the secondary, the secondary coil current, and/or the primary coil current as described above in connection with FIG. 27.

In operation 2820, the first processor 130 measures at least one status parameter. Here, the first processor 130 may sample the current signal provided by the current sensor 1620 to measure voltage regulation timing parameters, such as the regulation period $T_{reg}$, the power mode duration $T_{on}$, the idle mode duration $T_{off}$, the power mode duty cycle $DC_{on}$, and so. The power management module 140 may also measure or otherwise determine other circuit parameters on the primary side such as the primary current, the primary voltage, the phase between primary current and primary voltage, the input voltage, and so on.

In operation 2824, the system 11 performs at least one calculation using the at least one status parameter measured in operation 2820. As set forth in connection with FIG. 22 through FIG. 26, the first processor 130 may calculate the coupling coefficient, secondary heat flux, secondary coil temperature, primary heat flux, primary coil temperature, and so on.

In operation 2828, the power management module 140 determines if the system is in a fault condition. The fault condition may be a de-coupling of the coils, excess heat flux, excess temperature, insufficient available power, and so on. If the first processor 130 determines that the system 11 is in a fault condition, operation 2804 may be executed following operation 2828. If the power management module 140 determines that the system 11 is not in a fault condition, operation 2832 may be executed following operation 2828.

In operation 2832, the first processor 130 determines if the system is still approaching a fault condition. The fault condition may be a de-coupling of the coils, excess heat flux, excess temperature, insufficient available power, and so on. If the power management module 140 determines that the system 11 is not still approaching a fault condition, operation 2804 may again be executed following operation 2832. If the power management module 140 determines that the system 11 is still approaching a fault condition, operation 2816 may again be executed following operation 2832.

In operation 2836, the first processor 130 performs a second control operation based on the at least one calculation. Here, the first processor 130 may execute a control operation to adjust the power transferred from the primary to the secondary, the secondary coil current, and/or the primary coil current as described above in connection with FIG. 27. Operation 2820 may again be executed following operation 2836.

Figure 29:
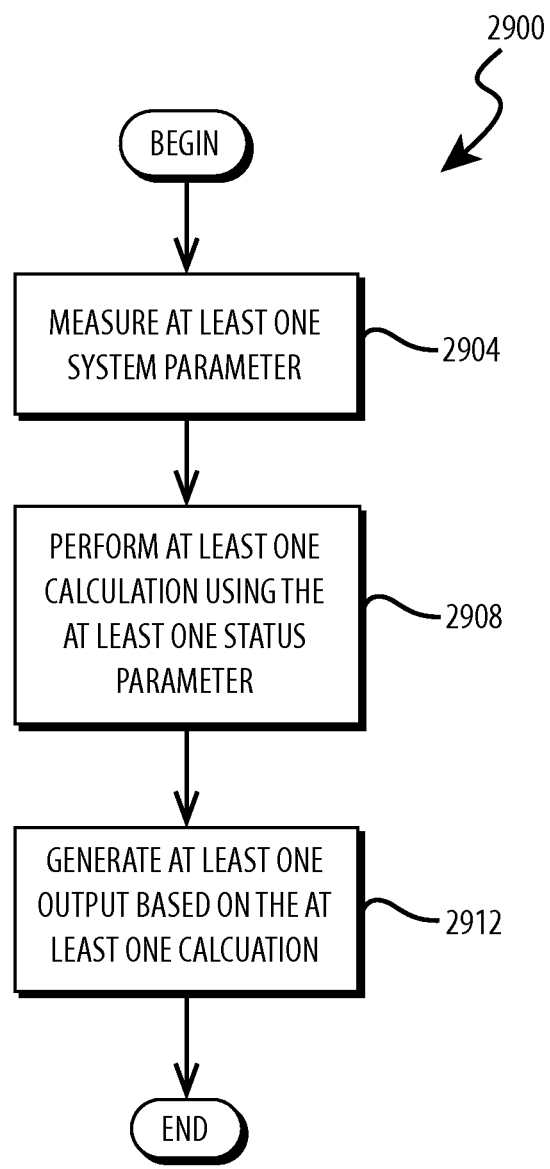
FIG. 29 is a flow chart that illustrates a method of providing at least one alert in accordance with embodiments discussed herein.

FIG. 29 is a flow chart 2900 that illustrates a method of providing at least one alert in accordance with embodiments discussed herein. The method illustrated by the flow chart 2900 includes operations executed by the first processor 130 shown in FIG. 15. The first processor 130 is external to the subject and so may be configured to receive input signals from various points on the primary side of the system 11. Based on these input signals, the first processor 130 may provide an alert on the primary side that is perceptible by a user who can then take action to affect the operation of the system 11 on either or both of the primary or secondary side.

Initially, in operation 2904, the system 11 measures at least one system parameter. Here, the first processor 130 may sample the current signal provided by the current sensor 1620 to measure voltage regulation timing parameters, such as the regulation period $T_{reg}$, the power mode duration $T_{on}$, the idle mode duration $T_{off}$, the power mode duty cycle $DC_{on}$, and so on. The first processor 130 may also measure or otherwise determine other circuit parameters on the primary side such as the primary current, the primary voltage, the phase between primary current and primary voltage, the input voltage, and so on.

In operation 2908, the system 11 performs at least one calculation using the at least one status parameter measured in operation 2904. As set forth in connection with FIG. 22 through FIG. 26, the first processor 130 may calculate the coupling coefficient, secondary heat flux, secondary coil temperature, primary heat flux, primary coil temperature, and so on.

In operation 2912, the system 11 generates at least one output based on the at least one calculation performed in operation 2908. In one embodiment, the system 11 provides output that includes assistance in placement and alignment of the external coil 1648 based on the calculated coupling coefficient. Thus, in operation 2904, the power management module 140 measures the idle mode duration $T_{off}$ and the power mode duty cycle $DC_{on}$. In operation 2908, the first processor 130 calculates the coupling coefficient as set forth in connection with FIG. 22. Finally, in operation 2912, the first processor 130 provides assistance in placement and alignment of the external coil 1648 based on the coupling coefficient calculated in the operation 2908.

The system 11 may also provide output that includes decoupling notifications based on the calculated coupling coefficient. Thus, in operation 2904, the first processor 130 measures the idle mode duration $T_{off}$ and the power mode duty cycle $DC_{on}$. In operation 2908, the first processor 130 calculates the coupling coefficient as set forth in connection with FIG. 22. Finally, in operation 2912, first processor 130 provides a decoupling notification based on the coupling coefficient calculated in operation 2908.

The system 11 may also provide output that includes heat flux notifications based on the calculated primary heat flux. Thus, in operation 2904, the first processor 130 measures the primary current $I_1$. In operation 2908, the first processor 130 calculates the primary heat flux as set forth in connection with FIG. 25. Finally, in operation 2912, the first processor 130 provides a heat flux notification based on the primary heat flux calculated in operation 2908.

The system 11 may also provide output that includes temperature notifications based on the calculated primary temperature. Thus, in operation 2904, the first processor 130 measures the primary current $I_1$. In operation 2908, the first processor 130 calculates the primary temperature as set forth in connection with FIG. 26. Finally, in operation 2912, the power management module 140 provides a temperature notification based on the primary heat flux calculated in operation 2908.

The system 11 may also provide output that includes heat flux notifications based on the calculated secondary heat flux. Thus, in operation 2904, the first processor 130 measures or otherwise determines the idle mode duration $T_{off}$, the power mode duty cycle $DC_{on}$, and the primary voltage $V_1$. In operation 2908, the power management module 140 calculates the secondary heat flux as set forth in connection with FIG. 23. Finally, in operation 2912, the first processor 130 provides a heat flux notification based on the secondary heat flux calculated in operation 2908.

The system 11 may also provide output that includes temperature notifications based on the calculated secondary temperature. Thus, in operation 2904, first processor 130 measures or otherwise determines the idle mode duration $T_{off}$, the power mode duty cycle $DC_{on}$, and the primary voltage $V_1$. In operation 2908, the first processor 130 calculates the secondary temperature as set forth in connection with FIG. 24. Finally, in operation 2912, the first processor 130 provides a secondary temperature notification based on the secondary temperature calculated in operation 2908.

Figure 30:
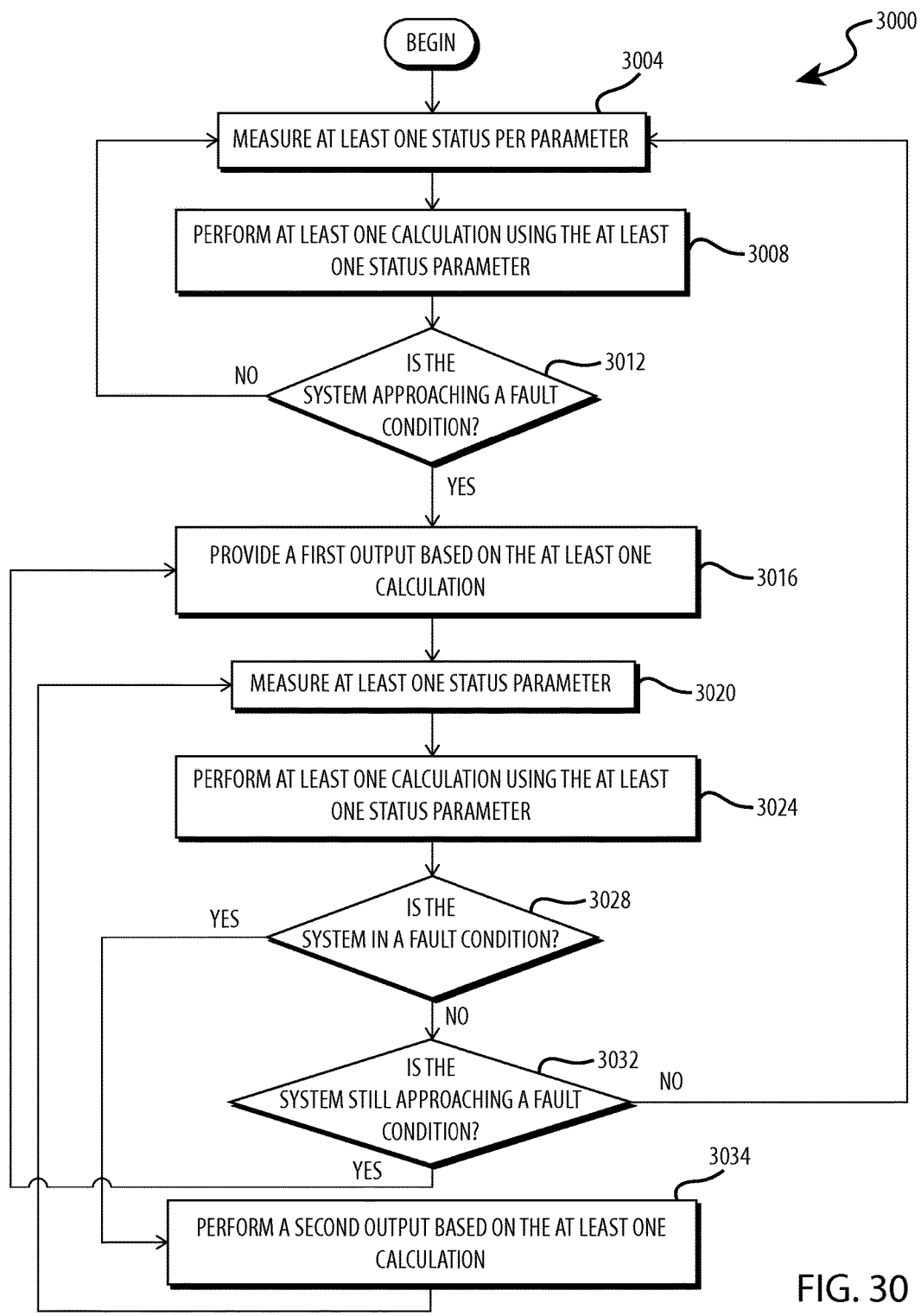
FIG. 30 is a flow chart that illustrates a method of providing alerts in accordance with embodiments discussed herein.

FIG. 30 is a flow chart 3000 that illustrates a method of providing at least two levels of alerts in accordance with embodiments discussed herein. The method illustrated by the flow chart 3000 includes operations executed by the first processor 130 shown in FIG. 29. The first processor 130 is external to the subject and so may be configured to receive input signals from various points on the primary side of the system 11. Based on these input signals, the first processor 130 may provide alerts on the primary side that are perceptible by a user who can then take action to affect the operation of the system 11 on either or both of the primary or secondary side.

Initially, in operation 3004, the system 11 measures at least one system parameter. Here, the first processor 130 may sample the current signal provided by the current sensor 3020 to measure voltage regulation timing parameters, such as the regulation period $T_{reg}$, the power mode duration $T_{on}$, the idle mode duration $T_{off}$, the power mode duty cycle $DC_{on}$, and so. The first processor 130 may also measure or otherwise determine other circuit parameters on the primary side such as the primary current, the primary voltage, the phase between primary current and primary voltage, the input voltage, and so on.

In operation 3008, the system 11 performs at least one calculation using the at least one status parameter measured in operation 3004. As set forth in connection with FIG. 22 through FIG. 26, the first processor 130 may calculate the coupling coefficient, secondary heat flux, secondary coil temperature, primary heat flux, primary coil temperature, and so on.

In operation 3012, the power management module 140 determines if the system is approaching a fault condition. The fault condition may be a de-coupling of the coils, excess heat flux, excess temperature, insufficient available power, and so on. If the first processor 130 determines that the system 11 is not approaching a fault condition, operation 3004 may again be executed following operation 3012. If the first processor 130 determines that the system 11 is approaching a fault condition, operation 3016 may be executed following operation 3012.

In operation 3016, the first processor 130 provides a first output based on the at least one calculation. Here, the first processor 130 may provide output that includes assistance in placement and alignment of the external coil, decoupling notifications, temperature notifications, and/or heat flux notifications as described above in connection with FIG. 29.

In operation 3020, the first processor 130 140 measures at least one status parameter. Here, the first processor 130 may sample the current signal provided by the current sensor 1620 to measure voltage regulation timing parameters, such as the regulation period $T_{reg}$, the power mode duration $T_{on}$, the idle mode duration $T_{off}$, the power mode duty cycle $DC_{on}$, and so on. The first processor 130 may also measure or otherwise determine other circuit parameters on the primary side such as the primary current, the primary voltage, the phase between primary current and primary voltage, the input voltage, and so on.

In operation 3024, the system 11 performs at least one calculation using the at least one status parameter measured in operation 3020. As set forth in connection with FIG. 22 through FIG. 26, the first processor 130 may calculate the coupling coefficient, secondary heat flux, secondary coil temperature, primary heat flux, primary coil temperature, and so on.

In operation 3028, the first processor 130 determines if the system is in a fault condition. The fault condition may be a de-coupling of the coils, excess heat flux, excess temperature, insufficient available power, and so on. If the first processor 130 determines that the system 11 is in a fault condition, operation 3036 may be executed following operation 3028. If the first processor 130 determines that the system 11 is not in a fault condition, operation 3032 may be executed following operation 3028.

In operation 3032, the power management module 140 determines if the system is still approaching a fault condition. The fault condition may be a de-coupling of the coils, excess heat flux, excess temperature, insufficient available power, and so on. If the first processor 130 determines that the system 11 is not still approaching a fault condition, operation 3004 may again be executed following operation 3032. If the first processor 130 determines that the system 11 is still approaching a fault condition, operation 3016 may again be executed following operation 3032.

In operation 3036, the first processor 130 provides a second output based on the at least one calculation. Here, first processor 130 may provide output that includes assistance in placement and alignment of the external coil, decoupling notifications, temperature notifications, and/or heat flux notifications as described above in connection with FIG. 29. Operation 3020 may again be executed following operation 3036.

Generally, as described throughout the disclosure, the system may execute one or any number of control operations. Similarly, the system may provide one or any number of levels of alerts or notifications. The alerts may discrete or continuous. A continuously increasing or decreasing alert may indicate multiple alert levels. For example, an audible tone or other sound may indicate multiple levels of alert by increasing or decreasing in volume, frequency, or the like. In another example, a light may indicate multiple levels of alert by increasing or decreasing in brightness, and so on.

The technology described herein may be implemented as logical operations and/or modules in one or more systems. The logical operations may be implemented as a sequence of processor-implemented steps executing in one or more computer systems and as interconnected machine or circuit modules within one or more computer systems. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the invention. One implementation of a computer program product provides a non-transitory computer program storage medium readable by a computer system and encoding a computer program. It should further be understood that the described technology may be employed in special purpose devices independent of a personal computer.

The invention claimed is:

1. A method of monitoring power transfer between a primary resonant network and secondary resonant network of a transcutaneous energy transfer system, comprising
measuring, at a primary power source module of the transcutaneous energy transfer system, at least one system status parameter associated with operation of the primary resonant network and the secondary resonant network, wherein the at least one system status parameter includes a regulation timing parameter;
performing calculations using the measured at least one of the at least one measured system status parameter, wherein performing calculations includes:
calculating a coupling coefficient between the primary resonant network and the secondary resonant network;
calculating the secondary coil current of the secondary resonant network;
calculating the secondary coil heat flux of the secondary resonant network; and
calculating the secondary coil temperature of the secondary resonant network; and
performing a control operation based on the calculations.

2. The method of claim 1, wherein measuring the regulation timing parameter includes measuring a primary current signal of the primary resonant network as an indication of timing of the voltage regulation in the secondary resonant network.

3. The method of claim 1, wherein measuring the regulation timing parameter includes measuring a primary coil voltage signal of the primary resonant network as an indication of timing of voltage regulation in the secondary resonant network.

4. The method of claim 1, wherein measuring the regulation timing parameter includes measuring a primary capacitor voltage signal of the primary resonant network as an indication of timing of voltage regulation in the secondary resonant network.

5. The method of claim 1, wherein the at least one system status parameter includes a primary current signal.

6. The method of claim 5, wherein measuring the primary current signal includes measuring a current in the primary through the operation of a current probe arranged in series with a primary coil.

7. The method of claim 5, wherein measuring the primary current signal includes measuring a voltage across a primary coil.

8. The method of claim 5, wherein measuring the primary current signal includes measuring a voltage across a primary capacitor.

9. The method of claim 1, wherein performing calculations using the measured at least one measured system status parameter comprises calculating a coupling coefficient.

10. The method of claim 9, wherein the control operation includes controlling input voltage to the primary resonant network based on the coupling coefficient.

11. The method of claim 5, wherein performing calculations using the measured system status parameters comprises
a first calculation of the primary heat flux; and
a second calculation of the primary coil temperature.

12. The method of claim 11, wherein the control operation includes control of primary coil current to control primary heat flux based on primary coil heat flux calculation.

13. The method of claim 11, wherein the control operation includes control of primary coil current to control primary temperature based on primary coil temperature calculation.

14. The method of claim 1, wherein the control operation includes control of secondary coil current of the secondary resonant network to control secondary heat flux of the secondary resonant network based on secondary coil heat flux calculation.

15. The method of claim 1, wherein the control operation includes control of secondary coil current of the secondary resonant network to control secondary temperature of the secondary resonant network based on secondary coil temperature calculation.

16. A method of monitoring power transfer between a primary resonant network and a secondary resonant network of a transcutaneous energy transfer system, comprising
measuring, at a primary power source module of the transcutaneous energy transfer system, at least one system status parameter associated with coupling between the primary resonant network and the secondary resonant network, wherein the at least one system status parameter includes a regulation timing parameter;
performing calculations using at least one of the at least one measured system status parameter, wherein performing calculations includes:
calculating a coupling coefficient between the primary resonant network and the secondary resonant network;
calculating the secondary coil current of the secondary resonant network;
calculating the secondary coil heat flux of the secondary resonant network; and
calculating the secondary coil temperature of the secondary resonant network; and
generating an output based on the calculations.

17. The method of claim 16, wherein the at least one system status parameter includes a primary current signal of the primary resonant network.

* * * * *